US006818611B1

(12) United States Patent
Altman

(10) Patent No.: US 6,818,611 B1
(45) Date of Patent: Nov. 16, 2004

(54) STABILIZED BIOACTIVE PEPTIDES AND METHODS OF IDENTIFICATION, SYNTHESIS AND USE

(75) Inventor: Elliot Altman, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 09/701,947

(22) PCT Filed: Oct. 12, 1999

(86) PCT No.: PCT/US99/23731

§ 371 (c)(1),
(2), (4) Date: Dec. 5, 2000

(87) PCT Pub. No.: WO00/22112

PCT Pub. Date: Apr. 20, 2000

Related U.S. Application Data
(60) Provisional application No. 60/112,150, filed on Dec. 14, 1998, and provisional application No. 60/104,013, filed on Oct. 13, 1998.

(51) Int. Cl.[7] .......................... A61K 38/46; A61K 38/00
(52) U.S. Cl. ...................... 514/2; 424/94.6; 424/192.1; 530/300; 435/68.1; 435/69.7
(58) Field of Search .......................... 514/2; 530/300; 424/94.6, 192.1; 435/68.1, 69.7

(56) References Cited

U.S. PATENT DOCUMENTS

| | | | |
|---|---|---|---|
| 5,212,083 A | 5/1993 | Haldenwang | |
| 5,270,181 A | 12/1993 | McCoy et al. | |
| 5,292,646 A | 3/1994 | McCoy et al. | |
| 5,380,712 A | 1/1995 | Ballance et al. | |
| 5,589,364 A | 12/1996 | Williams et al. | |
| 5,633,229 A | * 5/1997 | Kokryakov et al. | 514/12 |
| 5,646,016 A | 7/1997 | McCoy et al. | |
| 5,654,451 A | 8/1997 | Kari | |
| 5,741,646 A | 4/1998 | Sherley et al. | |
| 5,766,883 A | 6/1998 | Ballance et al. | |
| 5,792,831 A | 8/1998 | Maloy | |
| 5,804,553 A | * 9/1998 | Kokryakov et al. | 514/72 |
| 5,888,763 A | * 3/1999 | Hanafusa et al. | 435/69.1 |
| 6,143,524 A | 11/2000 | McCoy et al. | |
| 6,165,470 A | 12/2000 | Becquart et al. | |
| 6,329,209 B1 | * 12/2001 | Wagner et al. | 436/518 |
| 6,562,617 B1 | * 5/2003 | Anderson et al. | 435/325 |
| 6,566,498 B1 | * 5/2003 | Ni et al. | 530/350 |
| 6,630,197 B1 | * 10/2003 | Wood et al. | 427/154 |
| 2001/0056075 A1 | 12/2001 | Gyuris et al. | |

FOREIGN PATENT DOCUMENTS

| | | |
|---|---|---|
| WO | WO 90/07862 | 7/1990 |
| WO | WO 91/01743 | 2/1991 |
| WO | WO 92/07071 | 4/1992 |
| WO | WO 93/03156 | 2/1993 |
| WO | WO 96/40721 | 12/1996 |
| WO | WO 97/04110 | 2/1997 |
| WO | WO 98/22141 A2 A3 | 5/1998 |
| WO | WO 99/35494 | 7/1999 |
| WO | WO 99/36554 | 7/1999 |
| WO | WO 99/53079 | 10/1999 |
| WO | WO 01/45746 A2 | 6/2001 |
| WO | WO 01/77137 | 10/2001 |
| WO | WO 01/79258 | 10/2001 |
| WO | WO 01/79442 A2 | 10/2001 |
| WO | WO 01/79443 | 10/2001 |
| WO | WO 01/79444 | 10/2001 |
| WO | WO 01/79480 | 10/2001 |

OTHER PUBLICATIONS

Plaxco, K. W. (1998) Simplified proteins: minimalist solutions to the 'protein folding problem'. Curr. Opin. Struct Biol. vol. 8, pp. 80–85, Review.*

Sachdev, D. et al. (1998) Solubility of proteins isolated from inclusion bodies is enhanced by fusion to maltose–binding protein or thioredoxin. Protein Expr. Purif. vol. 12, pp. 122–132.*

Vanhoof, g. et al. (1995) Proline motifs in peptides and their biological processing. FASEB J. vol. 9, pp. 736–744.*

Shimizu, M. et al. (1998) Enhancement of antimicrobial activity of neuropeptide Y by N–terminal truncation. Antimicrob Agents Chemother. vol. 42, pp. 2745–2746.*

Nishida M. et al. (1998) Three–dimensional structure of *Escherichia coli* glutathione S–transferase complexed with glutathione sulfonate: catalytic roles of Cys 10 and His 106. J. Mol. Biol. vol. 281, pp. 135–147.*

Weiss S. et al. (1995) Overexpression of active Syrian golden hamster prion protein PrPc as a glutathione S–transferase fusion in heterologous systems. J. Virol. vol. 69, pp. 4776–483.*

Spurlino, J. et al. (1991) The 2.3–A resolution structure of the maltose– or maltodextrin–binding protein, a primary receptor of bacterial active transport and chemotaxis. J. Biol. Chem. vol. 266, pp. 5202–5219.*

Ast et al., "A rapid and sensitive bacterial assay to determine the inhibitory effect of 'interface' peptides on HIV–1 protease co–expressed in *Escherichia coli*," *J. Virological Methods*, 1998;71:77–85.

Roseman, "Hydrophilicity of polar amino acid side–chains is markedly reduced by flanking peptide bonds," *J Mol Biol.* Apr. 5, 1988;200(3):513–522.

(List continued on next page.)

Primary Examiner—Karen Cochrane Carlson
Assistant Examiner—Samuel Wei Liu
(74) Attorney, Agent, or Firm—Mueting Raasch & Gebhardt, P.A.

(57) ABSTRACT

An intracellular selection system allows concurrent screening for peptide bioactivity and stability. Randomized recombinant peptides are screened for bioactivity in a tightly regulated expression system, preferably derived from the wild-type lac operon. Bioactive peptides thus identified are inherently protease- and peptidase-resistant. Also provided are bioactive peptides stabilized by a stabilizing group at either the N-terminus, the C-terminus, or both. The stabilizing group can take the form of a small stable protein, such as the Rop protein, glutathione sulfotransferase, thioredoxin, maltose binding protein, or glutathione reductase, or one or more proline residues.

20 Claims, 9 Drawing Sheets

OTHER PUBLICATIONS

Agerberth et al., "Amino Acid Sequence of PR-39. Isolation from Pig Intestine of a New Member of the Family of Proline-arginine-rich Antibacterial Peptides," *Eur J Biochem.*, 202(3):819-854 (1991).

Banner et al., "Structure of the ColE1 Rop Protein at 1.7 Å Resolution," *J. Mol. Biol.*, 196:657-675 (1987).

Betz et al., "De Novo Design of Native Proteins: Characterization of Proteins Intended to Fold into Antiparallel, Rop-like, Four-Helix Bundles," *Biochemistry*, 36:2450-2458 (1997).

Cunningham et al., "Proline Specific Peptidases," *Biochi. Biophys. Acta*, 1343:160-186 (1997).

Frank et al., "Amino Acid Sequences of Two Proline-rich Bactenecins. Antimicrobial Peptides of Bovine Neutrophils." *J. Biol. Chem.*, 265(31):18871-18874 (1990).

Giza et al., "A Self-inducing Runaway-replication Plasmid Expression System Utilizing the Rop Protein," *Gene.* 78(1):73-84 (1989).

National Center for Biotechnology Information. National Library of Medicine, National Institutes of Health. GenBank Locus ECOLAC 7477 pb ds-DNA. Accession No. J01636, "*E. Coli* Lactose Operon with lacI, lacZ, lacY and lacA Genes." [online]. Bethesda. MD (Sep. 15, 1989). <URL: http://www.nchi.nlm.nih.gov/entrez/query.fcgi?cmd=Retrieve&db=Nucleotide&li st uids=146575&dopt=GenBank. (13 pgs).

National Center for Biotechnology Information, National Library of Medicine, National Institutes of Health, GenBank Locus SYNPBR322 4361 bp DNA circular SYN, Accession No. J01749, "Plasmid pBR322, Complete Genome," [online]. Bethesda, MD (May 20, 1991). <URL: http://www.ncbi.nlm.nih.gov/entrez./query.fcgi?cmd=Retrieve&db=Nucleotide&li st_uids=208958&dopt=GenBank, (13 pgs.).

National Center for Biotechnology Information, National Library of Medicine, National Institutes of Health, GenBank Locus SYNPUC8CV 2665 bp DNA circular SYN, Accession No. L09132, "pUC8c Cloning Vector (beta-galactosidase mRNA on Complementary Strand)," [online]. Bethesda, MD (Mar. 4, 1993). <URL.: http://www.ncbi.nlm.nih.gov/entrez/query.fcgi?cmd=Retrieve&db=Nucleotide&li st_uids=146575&dopt=GenBank, (18 pgs.).

Munson et al., "Speeding up Protein Folding: Mutations that Increase the Rate at Which Rop folds and Unfolds by Over Four Orders of Magnitude," *Folding & Design*, 2:77-87 (1997).

Plow et al., "Inhibition of Fibrinogen Binding to Human Platelets by the Tetrapeptide Glycyl-L-prolyl-L-arginyl-L-proline," *Proc. Natl. Acad. Sci. USA*, 79:3711-3715 (1982).

Soberon et al., "Construction and Characterization of New Cloning Vehicles. IV. Deletion Derivatives of pBR322 and pBR325," *Gene.* 9(3-4):287-305 (1980).

Steif et al., "Subunit Interactions Provide a Significant Contribution to the Stability of the Dimeric Four-α-I lelical-Bundle Protein ROP," *Biochemistry*, 32(15):3867-3875 (1993).

Vanhoof et al., "Proline Motifs in Peptides and Their Biological Processing," *FASEB J.*, 9:736-744 (1995).

Walter et al., "Proline Specific Endo- and Exopeptidases," *Mol. Cell. Bioch.*, 30(2):111-127 (1980).

Yansura et al., "Use of the *Escherichia coli* lac Repressor and Operator to Control Gene Expression in *Bacillus subtilis*," *Proc. Natl. Acad. Sci. USA*, 81:439-443 (1984).

Yaron et al., "Proline-Dependent Structural and Biological Properties of Peptides and Proteins," *Crit. Rev. Biochem. Mol. Biol.*, 28(1):31-81 (1993).

Barling et al., "Indirect [$^3$H] Methyl Exchange as a General Method for Labeling Methionine Residues: Application to Calcitonin." *Analytical Biochemistry.* 1985 Feb. 1; 144(2):542-552.

Bechinger et al., "Structure and orientation of the antibiotic peptide magainin in membranes by soild-state nuclear magnetic resonance spectroscopy." *Protein Science*, 1993; 2:2077-2084.

Bedarkar et al., "Polypeptide hormone-receptor interactions: the structure and receptor binding of insulin and glucagon," *Molecular Interactions and Activity in Proteins: Ciba Foundation Symposium*, Excerpta Medica, Amsterdam, 1978; 60:105-121.

Blane et al., "Examination of the Requirement for an Amphiphilic Helical Structure in β-Endorphin through the Design, Synthesis, and Study of Model Peptides," *J. Biol. Chem.*, Jul. 10, 1983; 258(13):8277-8284.

Cachia et al., "Calmodulin and Troponin C: A Comparative Study of the Interaction of Mastoparan and Troponin 1 Inhibitory Peptide [104-115]," *Biochemistry*, 1986: 25:3553-3562.

Carmona et al., "Conformational structure of bombesin as studied by virational and circular dichroism spectroscopy," *Biochim. Biophys. Acta*, 1995; 1246:128-134.

Colas et al., "Genetic selection of peptide aptamers that recognize and inhibit cyclin-dependent kinase 2," *Nature*, Apr. 11, 1996; 380:548-550.

Fabbrizio et al., "Inhibition of mammalian cell proliferation by genetically selected peptide aptamers that functionally antagonize E2F activity," *Oncogene*, 1999; 18:4357-4363.

Fezoui et al., "De movo design and structural characterization of an α-helical hairpin peptide: A model system for the study of protein folding intermediates," *Proc. Natl. Acad. Sci. USA*, Apr. 1994; 91:3675-3679.

Fong et al., "Necessity of the Disulfide Bond of Vasopressin for Antidiuretic Acitivity," *Biochem. Biophys. Res. Comm.*, 1964; 14(3):302-306.

Geyer et al., "Chapter 13: Selection of Genetic Agents from Random Peptide Aptamer Expression Libraries." *Methods in Enzymology.* 2000, Academic Press, 171-208.

Gronenborn et al., "A $^1$H-NMR study of the solution conformation of secretin," *FEBS Letters*, May 1987; 215(1):88-94.

Gyuris et al., "Cdil, a Human G1 and S Phase Protein Phosphatase That Associates with Cdk2," *Cell*, Nov. 19, 1993; 75:791-803.

Heitz et al., "$^1$H 2D NMR and Distance Geometry Study of the Folding of *Echallium elaterium* Trypsin Inhibitor, a Member of the Squash Inhibitors Family," 1989; 28:2392-2398.

Khan et al., "Sequence-Specific $^1$H NMR Assignments and Secondary Structure of Porcine Motilin," *Biochemistry*, 1990; 29:5743-5751.

LaVallie et al., "A Thioredoxin Gene Fusion Expression System That Circumvents Inclusion Body Formation in the *E. coli* Cytoplasm," *BioTechnology.* Feb. 1993.: 11(2):187-193.

Lechrer et al., "Neutrophils and Host Defense," *Ann. Intern. Med.* Jul. 15, 1988; 109(2):127-142.

Lu et al., "Expression of Thioredoxin Random Peptide Libraries on the *Escherichia coli* Cell Surface as Functional Fusions to Flagellin: A System Designed for Exploring Protein–Protein Interactions," *BioTechnology*, Apr. 1995.;13:366–372.

Makrides et al., "Extended in Vivo Half–Life of human soluble complement receptor type 1 fused to a serum albumin–binding receptor," *J. Pharmacology and Experimental Therapeutics*, 1996; 277(1):534–542.

Misono et al., "Rat Atrial Natriuretc Factor: Complete Amino Acid Sequence and Disulfide Linkage Essential for Biological Acitvity," *Biochem. Biophys. Res. Comm.*, Mar. 15, 1984: 119(2):524–529.

Mor et al., "Structure, Synthesis, and Activity of Dermaseptin b, a Novel Vertebrate Defensive Peptide from Frog Skin: Relationship with Adenoregulin," *Biochemistry*, 1994: 33:6642–6650.

Namboodiri et al., "Activation of Pineal Acetyl Coenzyme A Hydrolase by Disulfide Peptides," *J. Biol. Chem.*, 1982: 25:10030–10032.

Olivera et al., "Conotoxins." *J. Biol. Chem.*, Nov. 25, 1991; 266(33):22067–22070.

Reed et al., "Circular Dichroic Investigations of Secondary Structure in Synthetic Peptide Inhibitors of cAMP–Dependent Protein Kinase: A Model for Inhibitory Potential," *Biochemistry*, 1987:26:7641–7647.

Smith, "Filamentous Fusion Phage: Novel Expression Vectors that Display Cloned Antigens on the Virion Surface," *Science*, Jun. 14, 1985: 228:1315–1317.

Sugio et al., "Crystal structure of human serum albumin at 2.5 Å resolution," *Protein Engineering.* 1999; 12(6):439–446.

Terwilliger et al., "The Structure of Melittin," *J. Biol. Chem.*, Jun. 10, 1982; 257(11):6010–6015.

Urry et al., "Confirmational Studies on Neurohypophyseal Hormones: The Disulfide Bridge of Oxytocin," *Proc. Natl. Acad. Sci. USA.* 1968: 60:967–974.

Williams et al., "Secondary Structure of Substance P Bound to Liposomes in Organic Solvents and in Solution from Raman and CD Spectroscoopy," *J. Biol. Chem.*, Feb. 15, 1990; 265(5):2505–2513.

Xu et al., "Primary Structure and Anticandidal Acitvity of the Major Histatin from Parotid Secretion of the Subhuman Primate, *Macaca fascicularis,*" *J. Dent. Res.*, Nov. 1990.; 60(11):1717–1723.

Yeh et al., "Design of yeast–secreted albumin derivatives for human therapy: Biological and antiviral properties of a serum albumin–CD4 genetic conjugate," *Proc. Natl. Acad. Sci. USA.* Mar. 1992; 89:1904–1908.

Altman et al., "Characterization of Region in Mature LamB Protein That Interacts with a Component of the Export Machinery of *Escherichia coli*", *J. Biol. Chem.*, 265(3)):18148–18153 (1990).

Amann et al., "ATG vectors for regulated high–level expression of cloned genes in *Escherichia coli*", *Gene*, 40:183–190 (1985).

Amann et al., "Tightly regulated tac promoter vectors useful for the expression of unfused and fused proteins in *Escherichia coli*", *Gene*, 69:301–315 (1988).

Bai et al., "Structural Specificity of Mucosal–Cell Transport and Metabolism of Peptide Drugs: Implication for Oral Peptide Drug Delivery", *Pharmaccutical Res.*, 9(8):969–978 (1992).

Bai et al., "Targeting of Peptide and Protein Drugs to Specific Sites in the Oral Route", *Crit. Rev. Ther. Drug Carrier Systems*, 12(4):339–371 (1995).

Balbas et al., "Plasmid vector pBR322 and its special–purpose derivatives—a review", *Gene*, 50:3–40 (1986).

Beremand et al., "Synthesis, Cloning, and Expresion in *Escherichia coli* of a Spinach Acyl Carrier Protein–1 Gene", *Arch. Biochem. Biophys.*, 256(1):90–100 (1987).

Bolivar et al., "Construction and Characterization of New Cloning Vehicles", *Gene*, 2:95–113 (1977).

Brosius et al., "Regulation of ribosomal RNA promoters with a synthetic lac operator", *Proc. Nat'l. Acad. Sci. USA*, 81:6929–6933 (1984).

Brownlees et al., "Peptidases, Peptides, and the Mammalian Blood–Brain Barrier", *J. Neurochem.*, 60(3):793–803 (1993).

Casadaban et al., "Analysis of Gene Control Signals by DNA Fusion and Cloning in *Escherichia coli*", *J. Mol. Biol.*, 138:179–207 (1980).

Cesareni et al., "Control fo ColE1 DNA replication: The rop gene product negatively affects transcription from the replication primer promoter", *Proc. Nat'l. Acad. Sci. USA*, 79:6313–6317 (1982).

Chou et al., "Prediction of the Secondary Structure of Proteins from Their Amino Acid Sequence", *Adv. Enzymol.*, 47:45–148 (1978).

Chou, "Prediction of Protein Structural Classes from Amino Acid Compositions", in *Prediction of Protein Structure and the Principles of Protein Conformation*, Fasman, G.D. ed., Plenum Press, New York, N.Y., pp. 549–586 (1989).

Creighton, *Proteins—Structures and Molecular Properties*, W.II. Freeman and Company, N.Y., pp. 182–186 (1993).

Cwirla et al., "Peptides on phage: A vast library of peptides for indentifying ligans", *Proc. Nat'l. Acad. Sci. USA*, 87:6378–6382 (1990).

Devlin et al., "Random Peptide LIbraries: A Source of Specific Protein Binding Molecules", *Science*, 249:204–406 (1990).

Eberle et al., "Proton Nuclear Magnetic Resonance Assignments and Secondary Structure Determination of the ColE1 rop (rom) Protein", *Biochemistry*, 29:7402–7407 (1990).

Egleton et al., "Bioavailability and Transport of Peptides and Peptide Drugs into the Brain", *Peptides*, 18(9):1431–1439 (1997).

Eichler et al., "Peptide, Peptidomimetic, and Organic Synthetic Combinatorial Libraries", *Medicinal Reserach Reviews*, 15(6):481–496 (1995).

Eren et al., "Chemical Synthesis and Expression of a Synthetic Gene for the Flavodoxin from *Clostridium* MP", *J. Biol. Chem.*, 264(25):14874–14879 (1989).

Garnier et al., "Analysis of the Accuracy and Implications of Simple Methods for Predicting the Secondary Structure of Globular Proteins" *J. Mol. Biol.*, 120:97–120 (1978).

Ghosh et al., "cDNA Cloning, Expression, and Rapid Purification of a Kunitz–Type Winged Bean Chymotrypsin Inhibitor", *Protein Expression and Purification*, 10:100–106 (1997).

Godson, "An over–expression plasmid for *Escherichia coli* primase", *Gene*, 100:59–64 (1991).

Graña et al., "The Effects of Mutations in the ant Promoter of Phage P22 Depend on Context", *Genetics*, 120:319–327 (1988).

Grosjean et al., "Preferential codon usage in prokaryotic genes: the optimal codon–anticodon interaction energy and the selective codon usage in efficiently expressed genes", *Gene*, 18:199–209 (1982).

Guyer et al., Identification of a Sex–factor–affinity Site in *E. coli* as $\gamma o_3$ Cold Spring Harbor Symp. Quant. Biol., 45:135–140 (1980).

Ikemura, "Correlation between the Abundance of *Escherichia coli* Transfer RNAs and the Occurrence of the Respective Codons in its Protein Genes: A Proposal for a Synonymous Codon Choice that its Optimal for the *E. coli* Translational System", *J. Mol. Biol.*, 151:389–409 (1981).

Itakura et al., "Expression in *Escherichia coli* of a Chemically Synthesized Gene for the Hormone Somatostatin", *Science*, 198:1056–1063 (1977).

Klein et al., "The detection and classification of membrane–spanning proteins", *Biochim. Biophys. Acta.* 815:468–476 (1985).

Lam, "Application of combinatorial library methods in cancer research and drug discovery", *Anti–Cancer Drug Design*, 12:145–167 (1997).

Lebl et al., "Synthetic Peptide Libraries", in *Meth. Enzymol.*, 289:336–392 (1997).

Lin–Chao et al., "High copy number of the pUC plasmid results from a Rom/Rop–suppressible point mutation in RNA II", *Mol. Microbiol.*, 6(22):3385–3393 (1992).

Lowman, "Bacteriophage Display and Discovery of Peptide Leads For Drug Development", *Annu. Rev. Biophys. Biomol. Struct.*, 26:401–424 (1997).

Miller, "Experiments in Molecular Genetics", *Cold Spring Harbor Laboratory*, Cold Spring Harbor, N.Y., Title Page and Table of Contents (1972).

Miller et al., "An *E. coli* Gene Product Required for $\lambda$ Site–Specific Recombination" *Cell*, 20:711–719 (1980).

Miller et al., "Interior and Surface of Monomeric Proteins" *Mol. Biol.* 196:641–656 (1987).

Miller, "Protein Degradation and Proteolytic Modification", *Escherichia coli and Salmonella, Cellular and Molecular Biology*, 2nd Edition (Neidhardt, F.C. ed.), ASM Press, Washington, D.C., vol. 1:938–954 (1996).

Müller–Hill, "Lac Repressor and Lac Operator", *Prog. Biophys. Molec. Biol.*, 30(2/3):227–252 (1975).

Müller–Hill, *The lac Operon: A Short History of a Genetic Paradigm*, Walter de Gruyter, Berlin, New York, Title page and Table of Contents (1996).

O'Neil et al., "A Thermodynamic Scale for the Helix–Forming Tendencies of the Commonly Occurring Amino Acids", *Science*, 250:646–651 (1990).

Ooki et al., High level expression of rat $\gamma$–D–crystallin in *Escherischia coli*, *Biochemic*, 76(5):398–403 (1994).

Posfai et al., "Overproduction of the *Bacillus sphaericus* R modification methylase in *Escherichia coli* and its purification of homogenetiy", *Gene*, 50:63–67 (1986).

Raleigh et al. "McrA and McrB restriction phenotypes of some *E. coli* strains and implications for gene cloning". *Nucleic Acids Research*, 16:1563–1575 (1988).

Ranie et al., "Cloning of the triosephosphate isomerase gene of *Plasmodium faleiparum* and expression in *Escherichia coli*", *Molecular and Biochemical Parasitology*, 61:159–169 (1993).

Rawlings et al., "Evolutionary famiies of peptidases", *Biochem J.*, 290:205–218 (1993).

Sanders, "Drug delivery systems and routes of administration of peptide and protein drugs", *European Journal of Drug Metabolism and Pharmacokinetics*, 15(2):95–102 (1990).

Scott et al., "Searching for Peptide Ligands with an Epitope Library", *Science*, 249:386–390 (1990).

Scrutton et al., "Purification and characterization of glutathione reductase encoded by a cloned and over–expressed gene in *Escherichia coli*", *Biochem J.*, 245:875–880 (1987).

Sherman et al. "Methionine or Not Methionine at the Beginning of a Protein", BioEssays, 3(1):27–31 (1985).

Singer et al., "A Collection of Strains Containing Genetically LInked Alternating Antibiotic Resistance Elements for Genetic Mapping of *Escherichia coli*", *Microbiol. Rev.*, 53(1):1–24 (1989).

Smith et al., "[15] LIbraries of Peptides and Proteins Displayed on Filamentous Phage", *Meth. Enzymol.*, 217:228–257 (1993).

Studier et al., "Use of Bacteriophage T7 RNA Polymerase to Direct Selective High–level Expression of Cloned Genes", *J. Mol. Biol.*, 189:113–130 (1986).

Studier et al., "Use of T7 RNA Polymerase to Direct Expression of Cloned Genes", *Meth. Enzymol.*, 185:60–89 (1990).

Studier, "Use of Bacteriophage T7 Lysozyme to Improve an Inducible T7 Expression System", *J. Mol. Biol.*, 219:37–44 (1991).

Vieira et al., "The pUC plasmids, an M13mp7–derived system for insertion mutagenesis and sequencing with synthetic universal primers", *Gene*, 19:259–268 (1982).

Wearley, "Recent Progress in Protein and Peptide Delivery by Noninvasive Routes", *Crit. Rev. Ther. Drug Carrier Systems*, 8(4):331–394 (1991).

Weisemann et al., "Direct Selection of Mutations Reducing Transcription or Translation of the recA Gene of *Escherichia coli* with a recA–lacZ Protein Fusion", *J. Bacteriol.*, 163(2):748–755 (1985).

Wolfenden et al., "Affinities of Amino Acid Side Chains for Solvent Water", *Biochemistry*, 20:849–855 (1981).

Yanisch–Perron et al., "Improved M13 phage cloning vectors and host strains: nucleotide sequences of the M13mp18 and pUC19 vectors", *Gene*, 33:103–119 (1985).

Zukowski et al., Chromogenic identification of genetic regulatory signals in *Bacillus subtilis* based on expression of cloned *Pseudomonas* gene, *Proc. Nat'l. Acad. Sci. USA*, 80:1101–1105 (1983).

* cited by examiner

SEQ ID No: 1 lacI
stop
GGCAGTGAGCGCAACGCAATT AATGTGAGTTAGCTCACTCA TTAGGCACCCCAGGC TTTACA CTTTA
        O3                            CAP                                                −35

+1                                            lacZ
                                                                                   SD     start
TGCTTCCGGCTCG TATGTT GTGTGG AATTGTGAGCGGATAACAATTT CACAC AGGA AACAGCTATG
                    −10                          O1

FIG. 1 met glu⁻ asp⁻ glu⁻ asp⁻ xaa xaa xaa xaa xaa xaa xaa xaa
lys⁺ arg⁺ lys⁺ arg⁺ xaa xaa xaa xaa xaa xaa xaa xaa

FIG. 9

SEQUENCE LISTING

```
<160> NUMBER OF SEQ ID NOS: 110

<210> SEQ ID NO 1
<211> LENGTH: 133
<212> TYPE: DNA
<213> ORGANISM: Escherichia coli

<400> SEQUENCE: 1
ggcagtgagc gcaacgcaat taatgtgagt tagctcactc attaggcacc ccaggcttta      60
cactttatgc ttccggctcg tatgttgtgt ggaattgtga gcggataaca atttcacaca    120
ggaaacagct atg                                                        133

<210> SEQ ID NO 2
<211> LENGTH: 25
<212> TYPE: PRT
<213> ORGANISM: Artificial Sequence
<220> FEATURE:
<223> OTHER INFORMATION: Description of Artificial Sequence:  peptide
      having opposite charge ending motif
<221> NAME/KEY: SITE
<222> LOCATION: (6)..(21)
<223> OTHER INFORMATION: any amino acid

<400> SEQUENCE: 2

Met Glu Asp Glu Asp Xaa Xaa Xaa Xaa Xaa Xaa Xaa Xaa Xaa Xaa Xaa
 1               5                  10                  15

Xaa Xaa Xaa Xaa Xaa Arg Lys Arg Lys
            20                  25

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: stabilized
      angiotensin
```

```
<400> SEQUENCE: 3

Pro Pro Asp Arg Val Tyr Ile His Pro Phe His Ile Pro Pro
 1               5                  10

<210> SEQ ID NO 4
<211> LENGTH: 18
<212> TYPE: PRT
<213> ORGANISM: Artificial Sequence
<220> FEATURE:
<223> OTHER INFORMATION: Description of Artificial Sequence: stabilized
      angiotensin

<400> SEQUENCE: 4

Glu Asp Glu Asp Asp Arg Val Tyr Ile His Pro Phe His Ile Arg Lys
 1               5                  10                  15

Arg Lys

<210> SEQ ID NO 5
<211> LENGTH: 10
<212> TYPE: PRT
<213> ORGANISM: Homo sapiens

<400> SEQUENCE: 5

Asp Arg Val Tyr Ile His Pro Phe His Ile
 1               5                  10

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 6
gttgccattg ctgcaggcat                                              20

<210> SEQ ID NO 7
<211> LENGTH: 42
<212> TYPE: DNA
<213> ORGANISM: Artificial Sequence
<220> FEATURE:
<223> OTHER INFORMATION: Description of Artificial Sequence: primer

<400> SEQUENCE: 7
attgaattca taagatcttt cctgtgtgaa attgttatcc gc                     42

<210> SEQ ID NO 8
<211> LENGTH: 37
<212> TYPE: DNA
<213> ORGANISM: Artificial Sequence
<220> FEATURE:
<223> OTHER INFORMATION: Description of Artificial Sequence: primer

<400> SEQUENCE: 8
attgaattca ccatggacac catcgaatgg tgcaaaa                           37

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 9
```

-continued

```
gttgttgcca ttgctgcag                                                    19

<210> SEQ ID NO 10
<211> LENGTH: 43
<212> TYPE: DNA
<213> ORGANISM: Artificial Sequence
<220> FEATURE:
<223> OTHER INFORMATION: Description of Artificial Sequence: primer

<400> SEQUENCE: 10
tgtatgaatt cccgggtacc atggttgaag acgaaagggc ctc                         43

<210> SEQ ID NO 11
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 11
tactatagat ctatgaccat gattacggat tcactg                                 36

<210> SEQ ID NO 12
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 12
tacataaagc ttggcctgcc cggttattat tatttt                                 36

<210> SEQ ID NO 13
<211> LENGTH: 47
<212> TYPE: DNA
<213> ORGANISM: Artificial Sequence
<220> FEATURE:
<223> OTHER INFORMATION: Description of Artificial Sequence: primer

<400> SEQUENCE: 13
tatcatctgc agaggaaaca gctatgacca tgattacgga ttcactg                     47

<210> SEQ ID NO 14
<211> LENGTH: 47
<212> TYPE: DNA
<213> ORGANISM: Artificial Sequence
<220> FEATURE:
<223> OTHER INFORMATION: Description of Artificial Sequence: primer

<400> SEQUENCE: 14
tacatactcg agcaggaaag cttggcctgc ccggttatta ttatttt                     47

<210> SEQ ID NO 15
<211> LENGTH: 47
<212> TYPE: DNA
<213> ORGANISM: Artificial Sequence
<220> FEATURE:
<223> OTHER INFORMATION: Description of Artificial Sequence: primer

<400> SEQUENCE: 15
tatcatggat ccaggaaaca gctatgacca tgattacgga ttcactg                     47

<210> SEQ ID NO 16
<211> LENGTH: 36
<212> TYPE: DNA
<213> ORGANISM: Artificial Sequence
```

-continued

```
<220> FEATURE:
<223> OTHER INFORMATION: Description of Artificial Sequence: primer

<400> SEQUENCE: 16
tactatagat ctatggctat cgacgaaaac aaacag                                    36

<210> SEQ ID NO 17
<211> LENGTH: 40
<212> TYPE: DNA
<213> ORGANISM: Artificial Sequence
<220> FEATURE:
<223> OTHER INFORMATION: Description of Artificial Sequence: primer

<400> SEQUENCE: 17
atatataagc ttttaaaaat cttcgttagt ttctgctacg                                40

<210> SEQ ID NO 18
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 18
tactatagat ctatgaacaa aggtgtaatg cgacc                                     35

<210> SEQ ID NO 19
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 19
attagtgaat tcgcacaatc tctgcaataa gtcgt                                     35

<210> SEQ ID NO 20
<211> LENGTH: 15
<212> TYPE: DNA
<213> ORGANISM: Artificial Sequence
<220> FEATURE:
<223> OTHER INFORMATION: Description of Artificial Sequence: primer
      fragment

<400> SEQUENCE: 20
agatcttatg aattc                                                           15

<210> SEQ ID NO 21
<211> LENGTH: 15
<212> TYPE: DNA
<213> ORGANISM: Artificial Sequence
<220> FEATURE:
<223> OTHER INFORMATION: Description of Artificial Sequence: primer
      fragment

<400> SEQUENCE: 21
agatcttatg aattc                                                           15

<210> SEQ ID NO 22
<211> LENGTH: 15
<212> TYPE: DNA
<213> ORGANISM: Artificial Sequence
<220> FEATURE:
<223> OTHER INFORMATION: Description of Artificial Sequence: primer
      fragment

<400> SEQUENCE: 22
```

```
agatcttatg aattc                                                    15

<210> SEQ ID NO 23
<211> LENGTH: 93
<212> TYPE: DNA
<213> ORGANISM: Artificial Sequence
<220> FEATURE:
<223> OTHER INFORMATION: Description of Artificial Sequence: randomized
      oligonucleotide
<221> NAME/KEY: misc_feature
<222> LOCATION: (16)..(75)
<223> OTHER INFORMATION: a, g, c, or t

<400> SEQUENCE: 23
tactatagat ctatgnnnnn nnnnnnnnnn nnnnnnnnnn nnnnnnnnnn nnnnnnnnnn    60
nnnnnnnnnn nnnnntaata agaattctcg aca                                93

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 24
tgtcgagaat tcttatta                                                 18

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 25
tcattaatgc agctggcacg                                               20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 26
ttcatacacg gtgcctgact                                               20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 27
tagctcactc attaggcacc                                               20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 28
```

```
gatgacgatg agcgcattgt                                                    20
```

<210> SEQ ID NO 29
<211> LENGTH: 92
<212> TYPE: DNA
<213> ORGANISM: Artificial Sequence
<220> FEATURE:
<223> OTHER INFORMATION: Description of Artificial Sequence: antisense
      oligonucleotide

<400> SEQUENCE: 29

```
tactatagat ctacggtcac tgaattttgt ggcttgttgg accaactgcc ttagtaatag        60
tggaaggctg aaattaataa gaattctcga ca                                      92
```

<210> SEQ ID NO 30
<211> LENGTH: 91
<212> TYPE: DNA
<213> ORGANISM: Artificial Sequence
<220> FEATURE:
<223> OTHER INFORMATION: Description of Artificial Sequence: antisense
      oligonucleotide

<400> SEQUENCE: 30

```
tactatagat ctacgtggcg ggactcatgg attaaggta gggacgtggg gtttatgggt         60
taaaatagtt tgataataag aattctcgac a                                       91
```

<210> SEQ ID NO 31
<211> LENGTH: 92
<212> TYPE: DNA
<213> ORGANISM: Artificial Sequence
<220> FEATURE:
<223> OTHER INFORMATION: Description of Artificial Sequence: antisense
      oligonucleotide

<400> SEQUENCE: 31

```
tactatagat ctacgaacgg ccgaaccaaa cgaatccggg acccaccagc cgcctaaaca        60
gctaccagct gtggtaataa gaattctcga ca                                      92
```

<210> SEQ ID NO 32
<211> LENGTH: 93
<212> TYPE: DNA
<213> ORGANISM: Artificial Sequence
<220> FEATURE:
<223> OTHER INFORMATION: Description of Artificial Sequence: antisense
      oligonucleotide

<400> SEQUENCE: 32

```
tactatagat ctacggaccg tgaagtgatg tgtgcggcaa acaggaatg gaaggaacga         60 acgccatagg ccgcgtaata agaattctcg aca                                     93
```

<210> SEQ ID NO 33
<211> LENGTH: 93
<212> TYPE: DNA
<213> ORGANISM: Artificial Sequence
<220> FEATURE:
<223> OTHER INFORMATION: Description of Artificial Sequence: antisense
      oligonucleotide

<400> SEQUENCE: 33

```
tactatagat ctacgagggg cgccaactaa ggggggggga aggtatttgt cccgtgcata        60
atctcgggtg ttgtctaata agaattctcg aca                                     93
```

<210> SEQ ID NO 34

```
<211> LENGTH: 13
<212> TYPE: PRT
<213> ORGANISM: Artificial Sequence
<220> FEATURE:
<223> OTHER INFORMATION: Description of Artificial Sequence: stabilized
      peptide

<400> SEQUENCE: 34

Met Val Thr Glu Phe Cys Gly Leu Leu Asp Gln Leu Pro
 1               5                  10

<210> SEQ ID NO 35
<211> LENGTH: 86
<212> TYPE: DNA
<213> ORGANISM: Artificial Sequence
<220> FEATURE:
<223> OTHER INFORMATION: Description of Artificial Sequence: nucleic
      acid encoding stabilized peptide

<400> SEQUENCE: 35
caggaaagat ctatggtcac tgaattttgt ggcttgttgg accaactgcc ttagtaatag      60
tggaaggctg aaattaataa gaattc                                          86

<210> SEQ ID NO 36
<211> LENGTH: 16
<212> TYPE: PRT
<213> ORGANISM: Artificial Sequence
<220> FEATURE:
<223> OTHER INFORMATION: Description of Artificial Sequence: stabilized
      peptide

<400> SEQUENCE: 36

Met Trp Arg Asp Ser Trp Ile Lys Gly Arg Asp Val Gly Phe Met Gly
 1               5                  10                  15

<210> SEQ ID NO 37
<211> LENGTH: 85
<212> TYPE: DNA
<213> ORGANISM: Artificial Sequence
<220> FEATURE:
<223> OTHER INFORMATION: Description of Artificial Sequence: nucleic
      acid encoding stabilized peptide

<400> SEQUENCE: 37
caggaaagat ctatgtggcg ggactcatgg attaagggta gggacgtggg gtttatgggt      60
taaaatagtt tgataataag aattc                                           85

<210> SEQ ID NO 38
<211> LENGTH: 141
<212> TYPE: DNA
<213> ORGANISM: Artificial Sequence
<220> FEATURE:
<223> OTHER INFORMATION: Description of Artificial Sequence: nucleic
      acid encoding stabilized peptide

<400> SEQUENCE: 38
caggaaagat ctatgtcagg gggacatgtg acgagggagt gcaagtcggc gatgtccaat      60
cgttggatct acgtaataag aattctcatg tttgacagct tatcatcgat aagctttaat     120
gcggtagttt atcacagtta a                                               141

<210> SEQ ID NO 39
<211> LENGTH: 42
<212> TYPE: PRT
<213> ORGANISM: Artificial Sequence
<220> FEATURE:
```

<223> OTHER INFORMATION: Description of Artificial Sequence: stabilized
     peptide

<400> SEQUENCE: 39

Met Ser Gly Gly His Val Thr Arg Glu Cys Lys Ser Ala Met Ser Asn
1               5                   10                  15

Arg Trp Ile Tyr Val Ile Arg Ile Leu Met Phe Asp Ser Leu Ser Ser
            20                  25                  30

Ile Ser Phe Asn Ala Val Val Tyr His Ser
        35                  40

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: stabilized
     peptide

<400> SEQUENCE: 40

Met Tyr Leu Phe Ile Gly
1               5

<210> SEQ ID NO 41
<211> LENGTH: 75
<212> TYPE: DNA
<213> ORGANISM: Artificial Sequence
<220> FEATURE:
<223> OTHER INFORMATION: Description of Artificial Sequence: nucleic
     acid encoding stabilized peptide

<400> SEQUENCE: 41
caggaaagat ctatgtatttt gttcatcgga taatacttaa tggtccgctg gagaacttca     60
gtttaataag aattc                                                      75

<210> SEQ ID NO 42
<211> LENGTH: 87
<212> TYPE: DNA
<213> ORGANISM: Artificial Sequence
<220> FEATURE:
<223> OTHER INFORMATION: Description of Artificial Sequence: nucleic
     acid encoding stabilized peptide

<400> SEQUENCE: 42
caggaaagat ctatgcttct atttgggggg gactgcgggc agaaagccgg atactttact     60
gtgctaccgt caaggtaata agaattc                                         87

<210> SEQ ID NO 43
<211> LENGTH: 20
<212> TYPE: PRT
<213> ORGANISM: Artificial Sequence
<220> FEATURE:
<223> OTHER INFORMATION: Description of Artificial Sequence: stabilized
     peptide

<400> SEQUENCE: 43

Met Leu Leu Phe Gly Gly Asp Cys Gly Lys Ala Gly Tyr Phe Thr Val
1               5                   10                  15

Leu Pro Ser Arg
            20

<210> SEQ ID NO 44
<211> LENGTH: 75
<212> TYPE: DNA

<213> ORGANISM: Artificial Sequence
<220> FEATURE:
<223> OTHER INFORMATION: Description of Artificial Sequence: nucleic
      acid encoding stabilized peptide

<400> SEQUENCE: 44
caggaaagat ctatgattgg gggatcgttg agcttcgcct gggcaatagt ttgtaataag    60
aattctcatg tttga                                                    75

<210> SEQ ID NO 45
<211> LENGTH: 20
<212> TYPE: PRT
<213> ORGANISM: Artificial Sequence
<220> FEATURE:
<223> OTHER INFORMATION: Description of Artificial Sequence: stabilized
      peptide

<400> SEQUENCE: 45

Met Ile Gly Gly Ser Leu Ser Phe Ala Trp Ala Ile Val Cys Asn Lys
 1               5                  10                  15

Asn Ser His Val
            20

<210> SEQ ID NO 46
<211> LENGTH: 14
<212> TYPE: PRT
<213> ORGANISM: Artificial Sequence
<220> FEATURE:
<223> OTHER INFORMATION: Description of Artificial Sequence: stabilized
      peptide

<400> SEQUENCE: 46

Met Asn Gly Arg Thr Lys Arg Ile Arg Asp Pro Pro Ala Ala
 1               5                  10

<210> SEQ ID NO 47
<211> LENGTH: 86
<212> TYPE: DNA
<213> ORGANISM: Artificial Sequence
<220> FEATURE:
<223> OTHER INFORMATION: Description of Artificial Sequence: nucleic
      acid encoding stabilized peptide

<400> SEQUENCE: 47
caggaaagat ctatgaacgg ccgaaccaaa cgaatccggg acccaccagc cgcctaaaca    60
gctaccagct gtggtaataa gaattc                                        86

<210> SEQ ID NO 48
<211> LENGTH: 18
<212> TYPE: PRT
<213> ORGANISM: Artificial Sequence
<220> FEATURE:
<223> OTHER INFORMATION: Description of Artificial Sequence: stabilized
      peptide

<400> SEQUENCE: 48

Met Asp Arg Glu Val Met Cys Ala Ala Lys Gln Glu Trp Lys Glu Arg
 1               5                  10                  15

Thr Pro

<210> SEQ ID NO 49
<211> LENGTH: 87
<212> TYPE: DNA
<213> ORGANISM: Artificial Sequence
<220> FEATURE:

-continued

<223> OTHER INFORMATION: Description of Artificial Sequence: nucleic
      acid encoding stabilized peptide

<400> SEQUENCE: 49
caggaaagat ctatggaccg tgaagtgatg tgtgcggcaa acaggaatg gaaggaacga    60 acgccatagg ccgcgtaata agaattc                                      87

<210> SEQ ID NO 50
<211> LENGTH: 87
<212> TYPE: DNA
<213> ORGANISM: Artificial Sequence
<220> FEATURE:
<223> OTHER INFORMATION: Description of Artificial Sequence: nucleic
      acid encoding stabilized peptide

<400> SEQUENCE: 50
caggaaagat ctatgtagcc caatgcactg ggagcacgcg tgttaggtct agaagccacg    60
tacccattta atccataata agaattc                                       87

<210> SEQ ID NO 51
<211> LENGTH: 12
<212> TYPE: PRT
<213> ORGANISM: Artificial Sequence
<220> FEATURE:
<223> OTHER INFORMATION: Description of Artificial Sequence: stabilized
      peptide

<400> SEQUENCE: 51

Met Leu Gly Leu Glu Ala Thr Tyr Pro Phe Asn Pro
 1               5                  10

<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence: stabilized
      peptide

<400> SEQUENCE: 52

Met Arg Gly Ala Asn
 1               5

<210> SEQ ID NO 53
<211> LENGTH: 87
<212> TYPE: DNA
<213> ORGANISM: Artificial Sequence
<220> FEATURE:
<223> OTHER INFORMATION: Description of Artificial Sequence: nucleic
      acid encoding stabilized peptide

<400> SEQUENCE: 53
caggaaagat ctatgagggg cgccaactaa ggggggggga aggtatttgt cccgtgcata    60
atctcgggtg ttgtctaata agaattc                                       87

<210> SEQ ID NO 54
<211> LENGTH: 4
<212> TYPE: PRT
<213> ORGANISM: Artificial Sequence
<220> FEATURE:
<223> OTHER INFORMATION: Description of Artificial Sequence: N-terminal
      protective sequence
<221> NAME/KEY: SITE
<222> LOCATION: (1)
<223> OTHER INFORMATION: any amino acid
<221> NAME/KEY: SITE

```
<222> LOCATION: (4)
<223> OTHER INFORMATION: any amino acid

<400> SEQUENCE: 54

Xaa Pro Pro Xaa
  1

<210> SEQ ID NO 55
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 55
tactatagat ctatgaccaa acaggaaaaa accgcc                              36

<210> SEQ ID NO 56
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 56
tatacgtatt cagttgctca catgttcttt cctgcg                              36

<210> SEQ ID NO 57
<211> LENGTH: 41
<212> TYPE: DNA
<213> ORGANISM: Artificial Sequence
<220> FEATURE:
<223> OTHER INFORMATION: Description of Artificial Sequence: primer

<400> SEQUENCE: 57
aattcatact atagatctat gaccaaacag gaaaaaaccg c                        41

<210> SEQ ID NO 58
<211> LENGTH: 42
<212> TYPE: DNA
<213> ORGANISM: Artificial Sequence
<220> FEATURE:
<223> OTHER INFORMATION: Description of Artificial Sequence: primer

<400> SEQUENCE: 58
tatataatac atgtcagaat tcgaggtttt caccgtcatc ac                       42

<210> SEQ ID NO 59
<211> LENGTH: 96
<212> TYPE: DNA
<213> ORGANISM: Artificial Sequence
<220> FEATURE:
<223> OTHER INFORMATION: Description of Artificial Sequence: randomized
      oligonucloetide
<221> NAME/KEY: misc_feature
<222> LOCATION: (16)..(75)
<223> OTHER INFORMATION: a, g, c, or t

<400> SEQUENCE: 59
tactatagat ctatgnnnnn nnnnnnnnnn nnnnnnnnnn nnnnnnnnnn nnnnnnnnnn    60
nnnnnnnnnn nnnnncatag atctgcgtgc tgtgat                              96

<210> SEQ ID NO 60
<211> LENGTH: 21
<212> TYPE: DNA
<213> ORGANISM: Artificial Sequence
```

```
<220> FEATURE:
<223> OTHER INFORMATION: Description of Artificial Sequence: primer

<400> SEQUENCE: 60
atcacagcac gcagatctat g                                              21

<210> SEQ ID NO 61
<211> LENGTH: 36
<212> TYPE: DNA
<213> ORGANISM: Artificial Sequence
<220> FEATURE:
<223> OTHER INFORMATION: Description of Artificial Sequence: randomized
      oligonucleotide
<221> NAME/KEY: misc_feature
<222> LOCATION: (13)..(15)
<223> OTHER INFORMATION: a, g, c, or t

<400> SEQUENCE: 61
tactatgaat tcnnngaatt ctgccaccac tactat                              36

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 62
atagtagtgg tggcagaatt c                                              21

<210> SEQ ID NO 63
<211> LENGTH: 105
<212> TYPE: DNA
<213> ORGANISM: Artificial Sequence
<220> FEATURE:
<223> OTHER INFORMATION: Description of Artificial Sequence: randomized
      oligonucleotide
<221> NAME/KEY: misc_feature
<222> LOCATION: (22)..(81)
<223> OTHER INFORMATION: a, g, c, or t

<400> SEQUENCE: 63
tactatagat ctatgccgcc gnnnnnnnnn nnnnnnnnn nnnnnnnnnn nnnnnnnnn     60 nnnnnnnnnn nnnnnnnnnn nccgccgtaa taagaattcg tacat                   105

<210> SEQ ID NO 64
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 64
atgtacgaat tcttattacg gcgg                                           24

<210> SEQ ID NO 65
<211> LENGTH: 90
<212> TYPE: DNA
<213> ORGANISM: Artificial Sequence
<220> FEATURE:
<223> OTHER INFORMATION: Description of Artificial Sequence: randomized
      oligonucleotide
<221> NAME/KEY: misc_feature
<222> LOCATION: (18)
<223> OTHER INFORMATION: a, g, c, or t
<221> NAME/KEY: misc_feature
<222> LOCATION: (21)
<223> OTHER INFORMATION: a, g, c, or t
```

```
<221> NAME/KEY: misc_feature
<222> LOCATION: (24)
<223> OTHER INFORMATION: a, g, c, or t
<221> NAME/KEY: misc_feature
<222> LOCATION: (27)
<223> OTHER INFORMATION: a, g, c, or t
<221> NAME/KEY: misc_feature
<222> LOCATION: (30)
<223> OTHER INFORMATION: a, g, c, or t
<221> NAME/KEY: misc_feature
<222> LOCATION: (33)
<223> OTHER INFORMATION: a, g, c, or t
<221> NAME/KEY: misc_feature
<222> LOCATION: (36)
<223> OTHER INFORMATION: a, g, c, or t
<221> NAME/KEY: misc_feature
<222> LOCATION: (39)
<223> OTHER INFORMATION: a, g, c, or t
<221> NAME/KEY: misc_feature
<222> LOCATION: (42)
<223> OTHER INFORMATION: a, g, c, or t
<221> NAME/KEY: misc_feature
<222> LOCATION: (45)
<223> OTHER INFORMATION: a, g, c, or t
<221> NAME/KEY: misc_feature
<222> LOCATION: (48)
<223> OTHER INFORMATION: a, g, c, or t
<221> NAME/KEY: misc_feature
<222> LOCATION: (51)
<223> OTHER INFORMATION: a, g, c, or t
<221> NAME/KEY: misc_feature
<222> LOCATION: (54)
<223> OTHER INFORMATION: a, g, c, or t
<221> NAME/KEY: misc_feature
<222> LOCATION: (57)
<223> OTHER INFORMATION: a, g, c, or t
<221> NAME/KEY: misc_feature
<222> LOCATION: (60)
<223> OTHER INFORMATION: a, g, c, or t
<221> NAME/KEY: misc_feature
<222> LOCATION: (63)
<223> OTHER INFORMATION: a, g, c, or t
<221> NAME/KEY: misc_feature
<222> LOCATION: (66)
<223> OTHER INFORMATION: a, g, c, or t

<400> SEQUENCE: 65
tactatagat ctatgvanva nvanvanvan vanvanvanv anvanvanva nvanvanvan      60
vanvantaat aagaattctg ccagcactat                                      90

<210> SEQ ID NO 66
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 66
atagtgctgg cagaattctt atta                                            24

<210> SEQ ID NO 67
<211> LENGTH: 105
<212> TYPE: DNA
<213> ORGANISM: Artificial Sequence
<220> FEATURE:
<223> OTHER INFORMATION: Description of Artificial Sequence: randomized
      oligonucleotide
<221> NAME/KEY: misc_feature
<222> LOCATION: (28)..(75)
<223> OTHER INFORMATION: a, g, c, or t

<400> SEQUENCE: 67
tactatagat ctatggaaga cgaagacnnn nnnnnnnnnn nnnnnnnnnn nnnnnnnnnn      60
```

-continued nnnnnnnnnn nnnnncgtaa acgtaaataa taagaattcg tacat     105

<210> SEQ ID NO 68
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 68
atgtacgaat tcttattatt tacgtttacg     30

<210> SEQ ID NO 69
<211> LENGTH: 81
<212> TYPE: DNA
<213> ORGANISM: Artificial Sequence
<220> FEATURE:
<223> OTHER INFORMATION: Description of Artificial Sequence: nucleic
      acid encoding stabilized peptide

<400> SEQUENCE: 69
agatctatgc cgccgattct atggggcgaa gcgagaaagc gcttgtgggg tggggatcat     60
acaccgccgt aataagaatt c     81

<210> SEQ ID NO 70
<211> LENGTH: 21
<212> TYPE: PRT
<213> ORGANISM: Artificial Sequence
<220> FEATURE:
<223> OTHER INFORMATION: Description of Artificial Sequence: stabilized
      peptide

<400> SEQUENCE: 70

Met Pro Pro Ile Leu Trp Gly Glu Ala Arg Lys Arg Leu Trp Gly Gly
 1               5                  10                  15

Asp His Thr Pro Pro
            20

<210> SEQ ID NO 71
<211> LENGTH: 90
<212> TYPE: DNA
<213> ORGANISM: Artificial Sequence
<220> FEATURE:
<223> OTHER INFORMATION: Description of Artificial Sequence: nucleic
      acid encoding stabilized peptide

<400> SEQUENCE: 71
agatctatgc cgccgccgtt ggatattgtg tcgggtattg aggtaggggg gcatttgtgg     60
tgccgccgta ttaagaattc tcatgtttga     90

<210> SEQ ID NO 72
<211> LENGTH: 27
<212> TYPE: PRT
<213> ORGANISM: Artificial Sequence
<220> FEATURE:
<223> OTHER INFORMATION: Description of Artificial Sequence: stabilized
      peptide

<400> SEQUENCE: 72

Met Pro Pro Pro Leu Asp Ile Val Ser Gly Ile Glu Val Gly Gly His
 1               5                  10                  15

Leu Trp Cys Arg Arg Ile Lys Asn Ser His Val
            20                  25

<210> SEQ ID NO 73
<211> LENGTH: 81
<212> TYPE: DNA
<213> ORGANISM: Artificial Sequence
<220> FEATURE:
<223> OTHER INFORMATION: Description of Artificial Sequence: nucleic
      acid encoding stabilized peptide

<400> SEQUENCE: 73
agatctatgc cgccggacaa tccggtcctg tgatgaagcg gaggtcgacc aagggatat    60 cagccgccgt aataagaatt c                                             81

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence: stabilized
      peptide

<400> SEQUENCE: 74

Met Pro Pro Asp Asn Pro Val Leu
  1               5

<210> SEQ ID NO 75
<211> LENGTH: 81
<212> TYPE: DNA
<213> ORGANISM: Artificial Sequence
<220> FEATURE:
<223> OTHER INFORMATION: Description of Artificial Sequence: nucleic
      acid encoding stabilized peptide

<400> SEQUENCE: 75
agatctatgc cgccgctatt ggacggagat gacaaataga tatatgcgtg gttgtttttc    60
tgtccgccgt aataagaatt c                                             81

<210> SEQ ID NO 76
<211> LENGTH: 10
<212> TYPE: PRT
<213> ORGANISM: Artificial Sequence
<220> FEATURE:
<223> OTHER INFORMATION: Description of Artificial Sequence: stabilized
      peptide

<400> SEQUENCE: 76

Met Pro Pro Leu Leu Asp Gly Asp Asp Lys
  1               5                  10

<210> SEQ ID NO 77
<211> LENGTH: 79
<212> TYPE: DNA
<213> ORGANISM: Artificial Sequence
<220> FEATURE:
<223> OTHER INFORMATION: Description of Artificial Sequence: nucleic
      acid encoding stabilized peptide

<400> SEQUENCE: 77
agatctatgc cgccgaggtg gaagatgttg ataagacagt gacagatgcg ttccattact    60
cccgccgtaa taagaattc                                                79

<210> SEQ ID NO 78
<211> LENGTH: 11
<212> TYPE: PRT
<213> ORGANISM: Artificial Sequence
<220> FEATURE:

-continued

```
<223> OTHER INFORMATION: Description of Artificial Sequence: stabilized
      peptide

<400> SEQUENCE: 78

Met Pro Pro Arg Trp Lys Met Leu Ile Arg Gln
 1               5                  10

<210> SEQ ID NO 79
<211> LENGTH: 39
<212> TYPE: DNA
<213> ORGANISM: Artificial Sequence
<220> FEATURE:
<223> OTHER INFORMATION: Description of Artificial Sequence:  nucleic
      acid encoding stabilized peptide

<400> SEQUENCE: 79
agatctatga tgagagtagc gccgccgtaa taagaattc                               39

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: stabilized
      peptide

<400> SEQUENCE: 80

Met Met Arg Val Ala Pro Pro
 1               5

<210> SEQ ID NO 81
<211> LENGTH: 81
<212> TYPE: DNA
<213> ORGANISM: Artificial Sequence
<220> FEATURE:
<223> OTHER INFORMATION: Description of Artificial Sequence: nucleic
      acid encoding stabilized peptide

<400> SEQUENCE: 81
agatctatgc cgccgttgcg cggggcatgc gatgtatatg gggtaaattg aatgtcttgt        60
gggccgccgt aataagaatt c                                                  81

<210> SEQ ID NO 82
<211> LENGTH: 14
<212> TYPE: PRT
<213> ORGANISM: Artificial Sequence
<220> FEATURE:
<223> OTHER INFORMATION: Description of Artificial Sequence: stabilized
      peptide

<400> SEQUENCE: 82

Met Pro Pro Leu Arg Gly Ala Cys Asp Val Tyr Gly Val Asn
 1               5                  10

<210> SEQ ID NO 83
<211> LENGTH: 81
<212> TYPE: DNA
<213> ORGANISM: Artificial Sequence
<220> FEATURE:
<223> OTHER INFORMATION: Description of Artificial Sequence: nucleic
      acid encoding stabilized peptide

<400> SEQUENCE: 83
agatctatgc cgccggggag aggggaagcg gtgggagtga catgcttgag cgcgaacgtg        60
tacccgccgt aataagaatt c                                                  81
```

<210> SEQ ID NO 84
<211> LENGTH: 21
<212> TYPE: PRT
<213> ORGANISM: Artificial Sequence
<220> FEATURE:
<223> OTHER INFORMATION: Description of Artificial Sequence: stabilized
      peptide

<400> SEQUENCE: 84

Met Pro Pro Gly Arg Gly Glu Ala Val Gly Val Thr Cys Leu Ser Ala
 1               5                  10                  15

Asn Val Tyr Pro Pro
            20

<210> SEQ ID NO 85
<211> LENGTH: 81
<212> TYPE: DNA
<213> ORGANISM: Artificial Sequence
<220> FEATURE:
<223> OTHER INFORMATION: Description of Artificial Sequence: nucleic
      acid encoding stabilized peptide

<400> SEQUENCE: 85
agatctatgc cgccgggaag ggtagtgttc tttgtcgcta tctttgtttc cgcaatatgc      60
ctcccgccgt aataagaatt c                                               81

<210> SEQ ID NO 86
<211> LENGTH: 21
<212> TYPE: PRT
<213> ORGANISM: Artificial Sequence
<220> FEATURE:
<223> OTHER INFORMATION: Description of Artificial Sequence: stabilized
      peptide

<400> SEQUENCE: 86

Met Pro Pro Gly Arg Val Val Phe Phe Val Ala Ile Phe Val Ser Ala
 1               5                  10                  15

Ile Cys Leu Pro Pro
            20

<210> SEQ ID NO 87
<211> LENGTH: 81
<212> TYPE: DNA
<213> ORGANISM: Artificial Sequence
<220> FEATURE:
<223> OTHER INFORMATION: Description of Artificial Sequence: nucleic
      acid encoding stabilized peptide

<400> SEQUENCE: 87
agatctatgc cgccgaggtt cgctcatgag agtgttaaag ggctggggga cgttacaaaa      60
gctccgccgt aataagaatt c                                               81

<210> SEQ ID NO 88
<211> LENGTH: 21
<212> TYPE: PRT
<213> ORGANISM: Artificial Sequence
<220> FEATURE:
<223> OTHER INFORMATION: Description of Artificial Sequence: stabilized
      peptide

<400> SEQUENCE: 88

Met Pro Pro Arg Phe Ala His Glu Ser Val Lys Gly Leu Gly Asp Val
 1               5                  10                  15

Thr Lys Ala Pro Pro

```
<210> SEQ ID NO 89
<211> LENGTH: 72
<212> TYPE: DNA
<213> ORGANISM: Artificial Sequence
<220> FEATURE:
<223> OTHER INFORMATION: Description of Artificial Sequence: nucleic
      acid encoding stabilized peptide

<400> SEQUENCE: 89
agatctatgc atgacgaaca agaggaggag cacaataaaa aggataacga aaaagaacac    60
taataagaat tc                                                        72

<210> SEQ ID NO 90
<211> LENGTH: 18
<212> TYPE: PRT
<213> ORGANISM: Artificial Sequence
<220> FEATURE:
<223> OTHER INFORMATION: Description of Artificial Sequence: stabilized
      peptide

<400> SEQUENCE: 90

Met His Asp Glu Gln Glu Glu Glu His Asn Lys Lys Asp Asn Glu Lys
  1               5                  10                  15

Glu His

<210> SEQ ID NO 91
<211> LENGTH: 75
<212> TYPE: DNA
<213> ORGANISM: Artificial Sequence
<220> FEATURE:
<223> OTHER INFORMATION: Description of Artificial Sequence: nucleic
      acid encoding stabilized peptide

<400> SEQUENCE: 91
agatctatgc agcaggagca cgagcaaggc aggatgagca agaggatgaa gaataataag    60
aattctcatg tttga                                                     75

<210> SEQ ID NO 92
<211> LENGTH: 22
<212> TYPE: PRT
<213> ORGANISM: Artificial Sequence
<220> FEATURE:
<223> OTHER INFORMATION: Description of Artificial Sequence: stabilized
      peptide

<400> SEQUENCE: 92

Met Gln Gln Glu His Glu Gln Gly Arg Met Ser Lys Arg Met Lys Asn
  1               5                  10                  15

Asn Lys Asn Ser His Val
            20

<210> SEQ ID NO 93
<211> LENGTH: 75
<212> TYPE: DNA
<213> ORGANISM: Artificial Sequence
<220> FEATURE:
<223> OTHER INFORMATION: Description of Artificial Sequence: nucleic
      acid encoding stabilized peptide

<400> SEQUENCE: 93
agatctatga accatcataa tgaggccatg atcaacacaa tgaaaacgag gaataataag    60
aattctcatg tttga                                                     75
```

<210> SEQ ID NO 94
<211> LENGTH: 22
<212> TYPE: PRT
<213> ORGANISM: Artificial Sequence
<220> FEATURE:
<223> OTHER INFORMATION: Description of Artificial Sequence: stabilized
      peptide

<400> SEQUENCE: 94

Met Asn His His Asn Glu Ala Met Ile Asn Thr Met Lys Thr Arg Asn
 1               5                  10                  15

Asn Lys Asn Ser His Val
            20

<210> SEQ ID NO 95
<211> LENGTH: 72
<212> TYPE: DNA
<213> ORGANISM: Artificial Sequence
<220> FEATURE:
<223> OTHER INFORMATION: Description of Artificial Sequence: nucleic
      acid encoding stabilized peptide

<400> SEQUENCE: 95
agatctatga acgacgacaa tcagcaagag gataatcatg atcagcataa ggataacaaa      60
taataagaat tc                                                         72

<210> SEQ ID NO 96
<211> LENGTH: 18
<212> TYPE: PRT
<213> ORGANISM: Artificial Sequence
<220> FEATURE:
<223> OTHER INFORMATION: Description of Artificial Sequence: stabilized
      peptide

<400> SEQUENCE: 96

Met Asn Asp Asp Asn Gln Gln Glu Asp Asn His Asp Gln His Lys Asp
 1               5                  10                  15

Asn Lys

<210> SEQ ID NO 97
<211> LENGTH: 72
<212> TYPE: DNA
<213> ORGANISM: Artificial Sequence
<220> FEATURE:
<223> OTHER INFORMATION: Description of Artificial Sequence: nucleic
      acid encoding stabilized peptide

<400> SEQUENCE: 97
agatctatgc aagagcagga tcagcataat gataaccatc acgaggataa acataagaag      60
taataagaat tc                                                         72

<210> SEQ ID NO 98
<211> LENGTH: 18
<212> TYPE: PRT
<213> ORGANISM: Artificial Sequence
<220> FEATURE:
<223> OTHER INFORMATION: Description of Artificial Sequence: stabilized
      peptide

<400> SEQUENCE: 98

Met Gln Glu Gln Asp Gln His Asn Asp Asn His His Glu Asp Lys His
 1               5                  10                  15

Lys Lys

```
<210> SEQ ID NO 99
<211> LENGTH: 93
<212> TYPE: DNA
<213> ORGANISM: Artificial Sequence
<220> FEATURE:
<223> OTHER INFORMATION: Description of Artificial Sequence: nucleic
      acid encoding stabilized peptide

<400> SEQUENCE: 99
agatctatgg aagacgaaga cgagggtgcg tcagcgtggg gagcagaact tggtcgtgg    60 cagtcggtgc gtaaacgtaa ataataagaa ttc                               93

<210> SEQ ID NO 100
<211> LENGTH: 25
<212> TYPE: PRT
<213> ORGANISM: Artificial Sequence
<220> FEATURE:
<223> OTHER INFORMATION: Description of Artificial Sequence: stabilized
      peptide

<400> SEQUENCE: 100

Met Glu Asp Glu Asp Glu Gly Ala Ser Ala Trp Gly Ala Glu Leu Trp
 1               5                  10                  15

Ser Trp Gln Ser Val Arg Lys Arg Lys
             20                  25

<210> SEQ ID NO 101
<211> LENGTH: 93
<212> TYPE: DNA
<213> ORGANISM: Artificial Sequence
<220> FEATURE:
<223> OTHER INFORMATION: Description of Artificial Sequence: nucleic
      acid encoding stabilized peptide

<400> SEQUENCE: 101
agatctatgg aagacgaaga cggtctaggc atgggggtg ggttggtcag gctcacttta    60
ttattcttcc gtaaacgtaa ataataagaa ttc                               93

<210> SEQ ID NO 102
<211> LENGTH: 25
<212> TYPE: PRT
<213> ORGANISM: Artificial Sequence
<220> FEATURE:
<223> OTHER INFORMATION: Description of Artificial Sequence: stabilized
      peptide

<400> SEQUENCE: 102

Met Glu Asp Glu Asp Gly Leu Gly Met Gly Gly Gly Leu Val Arg Leu
 1               5                  10                  15

Thr Leu Leu Phe Phe Arg Lys Arg Lys
             20                  25

<210> SEQ ID NO 103
<211> LENGTH: 93
<212> TYPE: DNA
<213> ORGANISM: Artificial Sequence
<220> FEATURE:
<223> OTHER INFORMATION: Description of Artificial Sequence: nucleic
      acid encoding stabilized peptide

<400> SEQUENCE: 103
agatctatgg aagacgaaga cggggagagg atccagggg cccgctgtcc agtagcgctg    60
gtagatagac gtaaacgtaa ataataagaa ttc                               93
```

```
<210> SEQ ID NO 104
<211> LENGTH: 25
<212> TYPE: PRT
<213> ORGANISM: Artificial Sequence
<220> FEATURE:
<223> OTHER INFORMATION: Description of Artificial Sequence: stabilized
      peptide

<400> SEQUENCE: 104

Met Glu Asp Glu Asp Gly Glu Arg Ile Gln Gly Ala Arg Cys Pro Val
 1               5                  10                  15

Ala Leu Val Asp Arg Arg Lys Arg Lys
            20                  25

<210> SEQ ID NO 105
<211> LENGTH: 11
<212> TYPE: PRT
<213> ORGANISM: Artificial Sequence
<220> FEATURE:
<223> OTHER INFORMATION: Description of Artificial Sequence: stabilized
      peptide

<400> SEQUENCE: 105

Met Glu Asp Glu Asp Asp Arg Gly Arg Gly Arg
 1               5                  10

<210> SEQ ID NO 106
<211> LENGTH: 93
<212> TYPE: DNA
<213> ORGANISM: Artificial Sequence
<220> FEATURE:
<223> OTHER INFORMATION: Description of Artificial Sequence: nucleic
      acid encoding stabilized peptide

<400> SEQUENCE: 106
agatctatgg aagacgaaga cgacagggggg cgtgggcggt agctttaagt tgcgctaagt    60
tgcgagatac gtaaacgtaa ataataagaa ttc                                  93

<210> SEQ ID NO 107
<211> LENGTH: 93
<212> TYPE: DNA
<213> ORGANISM: Artificial Sequence
<220> FEATURE:
<223> OTHER INFORMATION: Description of Artificial Sequence: nucleic
      acid encoding stabilized peptide

<400> SEQUENCE: 107
agatctatgg aagacgaaga cggggggggcc gggaggaggg cctgtctttg ttccgcgctt    60
gttggggaac gtaaacgtaa ataataagaa ttc                                  93

<210> SEQ ID NO 108
<211> LENGTH: 25
<212> TYPE: PRT
<213> ORGANISM: Artificial Sequence
<220> FEATURE:
<223> OTHER INFORMATION: Description of Artificial Sequence: stabilized
      peptide

<400> SEQUENCE: 108

Met Glu Asp Glu Asp Gly Gly Ala Gly Arg Arg Ala Cys Leu Cys Ser
 1               5                  10                  15

Ala Leu Val Gly Glu Arg Lys Arg Lys
            20                  25
```

-continued

```
<210> SEQ ID NO 109
<211> LENGTH: 90
<212> TYPE: DNA
<213> ORGANISM: Artificial Sequence
<220> FEATURE:
<223> OTHER INFORMATION: Description of Artificial Sequence: nucleic
      acid encoding stabilized peptide

<400> SEQUENCE: 109
agatctatgg aagacgaaga caagcgtcgc gagaggagtg caaaagggcg tcatgtcggt      60
cggtcgatgc gtaaacgtaa ataagactgt                                      90

<210> SEQ ID NO 110
<211> LENGTH: 25
<212> TYPE: PRT
<213> ORGANISM: Artificial Sequence
<220> FEATURE:
<223> OTHER INFORMATION: Description of Artificial Sequence: stabilized
      peptide

<400> SEQUENCE: 110

Met Glu Asp Glu Asp Lys Arg Arg Glu Arg Ser Ala Lys Gly Arg His
  1               5                  10                  15

Val Gly Arg Ser Met Arg Lys Arg Lys
             20                  25
```

STABILIZED BIOACTIVE PEPTIDES AND METHODS OF IDENTIFICATION, SYNTHESIS AND USE

This parent application claims the benefit of U.S. Provisional Patent Applications Ser. Nos. 60/104,013, filed Oct. 13, 1998, and 60/112,150, filed Dec. 14, 1998.

BACKGROUND OF THE INVENTION

Bioactive peptides are small peptides that elicit a biological activity. Since the discovery of secretin in 1902, over 500 of these peptides which average 20 amino acids in size have been identified and characterized. They have been isolated from a variety of systems, exhibit a wide range of actions, and have been utilized as therapeutic agents in the field of medicine and as diagnostic tools in both basic and applied research. Tables 1 and 2 list some of the best known bioactive peptides.

TABLE 1

Bioactive peptides utilized in medicine

| Name | Isolated From | Size In Amino Acids | Therapeutic Use |
|---|---|---|---|
| Angiotensin II | Human Plasma | 8 | Vasoconstrictor |
| Bradykinin | Human Plasma | 9 | Vasodilator |
| Caerulein | Frog Skin | 10 | Choleretic Agent |
| Calcitonin | Human Parathyroid Gland | 32 | Calcium Regulator |
| Cholecystokinin | Porcine Intestine | 33 | Cholerectic Agent |
| Corticotropin | Porcine Pituitary Gland | 39 | Hormone |
| Eledoisin | Octoped Venom | 11 | Hypotensive Agent |
| Gastrin | Porcine Stomach | 17 | Gastric Activator |
| Glucagon | Porcine Pancreas | 29 | Antidiabetic Agent |
| Gramicidin D | *Bacillus brevis* Bacteria | 11 | Antibacterial Agent |
| Insulin | Canine Pancreas | | Antidiabetic Agent |
| Insulin A | | 21 | |
| Insulin B | | 30 | |
| Kallidin | Human Plasma | 10 | Vasodilator |
| Luteinizing Hormone-Releasing Factor | Bovine Hypothalamus | 10 | Hormone Stimulator |
| Melittin | Bee Venom | 26 | Antirheumatic Agent |
| Oxytocin | Bovine Pituitary Gland | 9 | Oxytocic Agent |
| Secretin | Canine Intestine | 27 | Hormone |
| Sermorelin | Human Pancreas | 29 | Hormone Stimulator |
| Somatostatin | Bovine Hypothalamus | 14 | Hormone Inhibitor |
| Vasopressin | Bovine Pituitary Gland | 9 | Antidiuretic Agent |

TABLE 2

Bioactive peptides utilized in applied research

| Name | Isolated From | Size In Amino Acids | Biological Activity |
|---|---|---|---|
| Atrial Natriuretic Peptide | Rat Atria | 28 | Natriuretic Agent |
| Bombesin | Frog Skin | 14 | Gastric Activator |
| Conamokin G | Snail Venom | 17 | Neurotransmitter |
| Conotoxin Gl | Snail Venom | 13 | Neuromuscular Inhibitor |
| Defensin HNP-1 | Human Neutrophils | 30 | Antimicrobal Agent |
| Delta Sleep-Inducing Peptide | Rabbit Brain | 9 | Neurological Affector |
| Dermaseptin | Frog Skin | 34 | Antimicrobial Agent |
| Dynorphin | Porcine Brain | 17 | Neurotransmitter |
| EET1 II | *Ecballium elaterium* seeds | 29 | Protease Inhibitor |
| Endorphin | Human Brain | 30 | Neurotransmitter |
| Enkephalin | Human Brain | 5 | Neurotransmitter |
| Histatin 5 | Human Saliva | 24 | Antibacterial Agent |
| Mastoparan | *Vespid* Wasps | 14 | Mast Cell Degranulator |
| Magainin 1 | Frog Skin | 23 | Antimicrobial Agent |
| Melanocyte Stimulating Hormone | Porcine Pituitary Gland | 13 | Hormone Stimulator |
| Motilin | Canine Intestine | 22 | Gastric Activator |
| Neurotensin | Bovine Brain | 13 | Neurotransmitter |
| Physalaemin | Frog Skin | 11 | Hypotensive Agent |
| Substance P | Horse Intestine | 11 | Vasodilator |
| Vasoactive Intestinal Peptide | Porcine Intestine | 28 | Hormone |

Where the mode of action of these peptides has been determined, it has been found to be due to the interaction of the bioactive peptide with a specific protein target. In most of the cases, the bioactive peptide acts by binding to and inactivating its protein target with extremely high specificities. Binding constants of these peptides for their protein targets typically have been determined to be in the nanomolar (nM, $10^{-9}$ M) range with binding constants as high as $10^{-12}$ M (picomolar range) having been reported. Table 3 shows target proteins inactivated by several different bioactive peptides as well as the binding constants associated with binding thereto.

TABLE 3

Binding constants of bioactive peptides

| Bioactive Peptide | Size in Amino Acids | Inhibited Protein | Binding Constant |
|---|---|---|---|
| α-Conotoxim GIA | 15 | Nicotinic Acetylcholine | $1.0 \times 10^{-9}$ M |
| EET1 II | 29 | Trypsin | $1.0 \times 10^{-12}$ M |
| H2 (7–15) | 8 | HSV Ribonucleotide Reductase | $3.6 \times 10^{-5}$ M |
| Histatin 5 | 24 | Bacteroides gingivalis Protease | $5.5 \times 10^{-8}$ M |
| Melittin | 26 | Calmodulin | $3.0 \times 10^{-9}$ M |
| Myotoxin (29–42) | 14 | ATPase | $1.9 \times 10^{-5}$ M |
| Neurotensin | 13 | Ni Regulatory Protein | $5.6 \times 10^{-11}$ M |
| Pituitary Adenylate Cyclase Activating Polypeptide | 38 | Calmodulin | $1.5 \times 10^{-8}$ M |
| PKI (5–24) | 20 | cAMP-Dependent Protein Calpain | $2.3 \times 10^{-9}$ M |
| SCP (153–180) | 27 | Protein Calpain | $3.0 \times 10^{-8}$ M |
| Secretin | 27 | HSR G Protein | $3.2 \times 10^{-9}$ M |
| Vasocactive Intestinal Peptide | 28 | GPRN1 G Protein | $1.5 \times 10^{-9}$ M |

Recently, there has been an increasing interest in employing synthetically derived bioactive peptides as novel pharmaceutical agents due to the impressive ability of the naturally occurring peptides to bind to and inhibit specific protein targets. Synthetically derived peptides could be useful in the development of new antibacterial, antiviral, and anticancer agents. Examples of synthetically derived antibacterial or antiviral peptide agents would be those capable of binding to and preventing bacterial or viral surface proteins from interacting with their host cell receptors, or preventing the action of specific toxin or protease proteins. Examples of anticancer agents would include synthetically derived peptides that could bind to and prevent the action of specific oncogenic proteins.

To date, novel bioactive peptides have been engineered through the use of two different in vitro approaches. The first approach produces candidate peptides by chemically synthesizing a randomized library of 6–10 amino acid peptides (J. Eichler et al., Med. Res. Rev. 15:481–496 (1995); K. Lam, Anticancer Drug Des. 12:145–167 (1996); M. Lebl et al., Methods Enzymol. 289:336–392 (1997)). In the second approach, candidate peptides are synthesized by cloning a randomized oligonucleotide library into a Ff filamentous phage gene, which allows peptides that are much larger in size to be expressed on the surface of the bacteriophage (H. Lowman, Ann. Rev. Biophys. Biomol. Struct. 26:401–424 (1997); G. Smith et al., et al. Meth. Enz. 217:228–257 (1993)). To date, randomized peptide libraries up to 38 amino acids in length have been made, and longer peptides are likely achievable using this system. The peptide libraries that are produced using either of these strategies are then typically mixed with a preselected matrix-bound protein target. Peptides that bind are eluted, and their sequences are determined. From this information new peptides are synthesized and their inhibitory properties are determined. This is a tedious process that only screens for one biological activity at a time.

Although these in vitro approaches show promise, the use of synthetically derived peptides has not yet become a mainstay in the pharmaceutical industry. The primary obstacle remaining is that of peptide instability within the biological system of interest as evidenced by the unwanted degradation of potential peptide drugs by proteases and/or peptidases in the host cells. There are three major classes of peptidases which can degrade larger peptides: amino and carboxy exopeptidases which act at either the amino or the carboxy terminal end of the peptide, respectively, and endopeptidases which act on an internal portion of the peptide. Aminopeptidases, carboxypeptidases, and endopeptidases have been identified in both prokaryotic and eukaryotic cells. Many of those that have been extensively characterized were found to function similarly in both cell types. Interestingly, in both prokaryotic and eukaryotic systems, many more arninopeptidases than carboxypeptidases have been identified to date.

Approaches used to address the problem of peptide degradation have included the use of D-amino acids or modified amino acids as opposed to the naturally occurring L-amino acids (e.g., J. Eichler et al., Med Res Rev. 15:481–496 (1995); L. Sanders, Eur. J. Drug Metabol. Pharmacokinetics 15: 95–102 (1990)), the use of cyclized peptides (e.g., R. Egleton, et al., Peptides 18: 1431–1439 (1997)), and the development of enhanced delivery systems that prevent degradation of a peptide before it reaches its target in a patient (e.g., L. Wearley, Crit. Rev. Ther. Drug Carrier Syst. 8: 331–394 (1991); L. Sanders, Eur. J. Drug Metabol. Pharmacokinetics 15: 95–102 (1990)). Although these approaches for stabilizing peptides and thereby preventing their unwanted degradation in the biosystem of choice (e.g., a patient) are promising, there remains no way to routinely and reliably stabilize peptide drugs and drug candidates. Moreover, many of the existing stabilization and delivery methods cannot be directly utilized in the screening and development of novel useful bioactive peptides. A biological approach that would serve as both a method of stabilizing peptides and a method for identifying novel bioactive peptides would represent a much needed advance in the field of peptide drug development.

SUMMARY OF THE INVENTION

The present invention provides an intracellular screening method for identifying novel bioactive peptides. A host cell is transformed with an expression vector comprising a tightly regulable control region operably linked to a nucleic acid sequence encoding a peptide. The transformed host cell is first grown under conditions that repress expression of the peptide and then, subsequently, expression of the peptide is induced. Phenotypic changes in the host cell upon expression of the peptide are indicative of bioactivity, and are evaluated. If, for example, expression of the peptide is accompanied by inhibition of host cell growth, the expressed peptide constitutes a bioactive peptide, in that it functions as an inhibitory peptide.

Intracellular identification of bioactive peptides can be advantageously carried out in a pathogenic microbial host cell. Bioactive peptides having antimicrobial activity are readily identified in a microbial host cell system. Further, the method can be carried out in a host cell that has not been modified to reduce or eliminate the expression of naturally expressed proteases or peptidases. When carried out in a host cell comprising proteases and peptides, the selection process of the invention is biased in favor of bioactive peptides that are protease- and peptidase-resistant.

The tightly regulable control region of the expression vector used to transform the host cell according to the invention is preferably derived from the wild-type *Escherichia coli lac* operon, and the transformed host preferably comprises an amount of Lac repressor protein effective to repress expression of the peptide during host cell growth under repressed conditions. To insure a sufficient amount of Lac repressor protein, the host cell can be transformed with a second vector that overproduces Lac repressor protein.

Optionally, the expression vector used to transform the host cell can be genetically engineered to encode a stabilized peptide that is resistant to peptidases and proteases. For example, the coding sequence can be designed to encode a stabilizing group at either or both of the peptide's N-terminus or C-terminus. As another example, the coding sequence can be designed to encode a stabilizing motif such as an α-helix motif or an opposite charge ending motif, as described below. The presence of a stabilizing group at a peptide terminus or a stabilizing motif can slow down the rate of intracellular degradation of the peptide.

The invention further provides a bioactive peptide having a first stabilizing group comprising the N-terminus and a second stabilizing group comprising the C-terminus. Preferably, the first stabilizing group is selected from the group consisting of a small stable protein. Pro-, Pro-Pro-, Xaa-Pro- and Xaa-Pro-Pro-; and the second stabilizing group is selected from the group consisting of a small stable protein, -Pro, -Pro-Pro, -Pro-Xaa and -Pro-Pro-Xaa. Suitable small stable proteins include Rop protein, glutathione sulfotransferase, thioredoxin, maltose binding protein, and glutathione reductase. In addition, the invention provides a bioactive peptide stabilized by an opposite charge ending motif, as described below. The bioactive peptide is preferably an antimicrobial peptide or a therapeutic peptide drug.

Also provided by the invention is a polyeptide that can be cleaved to yield a bioactive peptide having a stabilizing group at either or both of its N- and C-termini. The cleavable polypeptide accordingly comprises a chemical or enzymatic cleavage site either immediately preceding the N-terminus of the bioactive peptide or immediately following the C-terminus of the bioactive peptide.

The invention further provides a fusion protein comprising a four-helix bundle protein, preferably the Rop protein, and a polypeptide. The four-helix bundle protein is positioned at either the N-terminus or the C-terminus of the fusion protein, and accordingly can be fused to either the N-terminus or the C-terminus of the polypeptide.

The present invention also provides a method for using an antimicrobial peptide. An antimicrobial peptide is stabilized by linking a first stabilizing group to the N-terminus of an antimicrobial peptide, and, optionally, a second stabilizing group to the C-terminus of the antimicrobial peptide. Alternatively, the antimicrobial peptide is stabilized by flanking the peptide sequence with an opposite charge ending motif, as described below. The resulting stabilized antimicrobial peptide is brought into contact with a microbe, preferably a pathogenic microbe, for example to inhibit the growth or toxicity of the microbe.

The invention also provides a method for treating a patient having a condition treatable with a peptide drug, comprising administering to the patient a stabilized peptide drug having at least one of a first stabilizing group comprising the N-terminus of the stabilized peptide drug and a second stabilizing groupj comprising the C-terminus of the stabilized peptide drug. Optionally, prior to administration of the stabilized peptide drug, the first stabilizing group is covalently linked to the N-terminus of a peptide drug, and the second stabilizing group is covalently linked to the C-terminus of the peptide administering to the patient a peptide drug that has been stabilized by flanking the peptide sequence with an opposite charge ending motif, as described below.

BRIEF DESCRIPTION OF THE DRAWINGS

FIG. 1 shows the control region (SEQ ID NO:1) of the wild-type lac operon from the auxiliary operator O3 through the translational start of the lacZ gene. DNA binding sites include the operators O3 and O1 (both underlined), catabolite gene activator proteion (CAP) (boxed), the −35 site (boxed), and the −10 site (boxed), while important RNA and protein sites include the LacI translation stop site (TGA), the +1 lacZ transcription start site, the Shine Dalgarno (SD) ribosome binding site for lacZ, and the LacZ translation start site (ATG).

FIG. 9 illustrates a peptide (SEQ ID NO:2) having the opposite charge ending motif, wherein the amino and carboxy termini of the peptide are stabilized by the interactions of the opposite charge ending amino acids.

DETAILED DESCRIPTION

Figure 2:
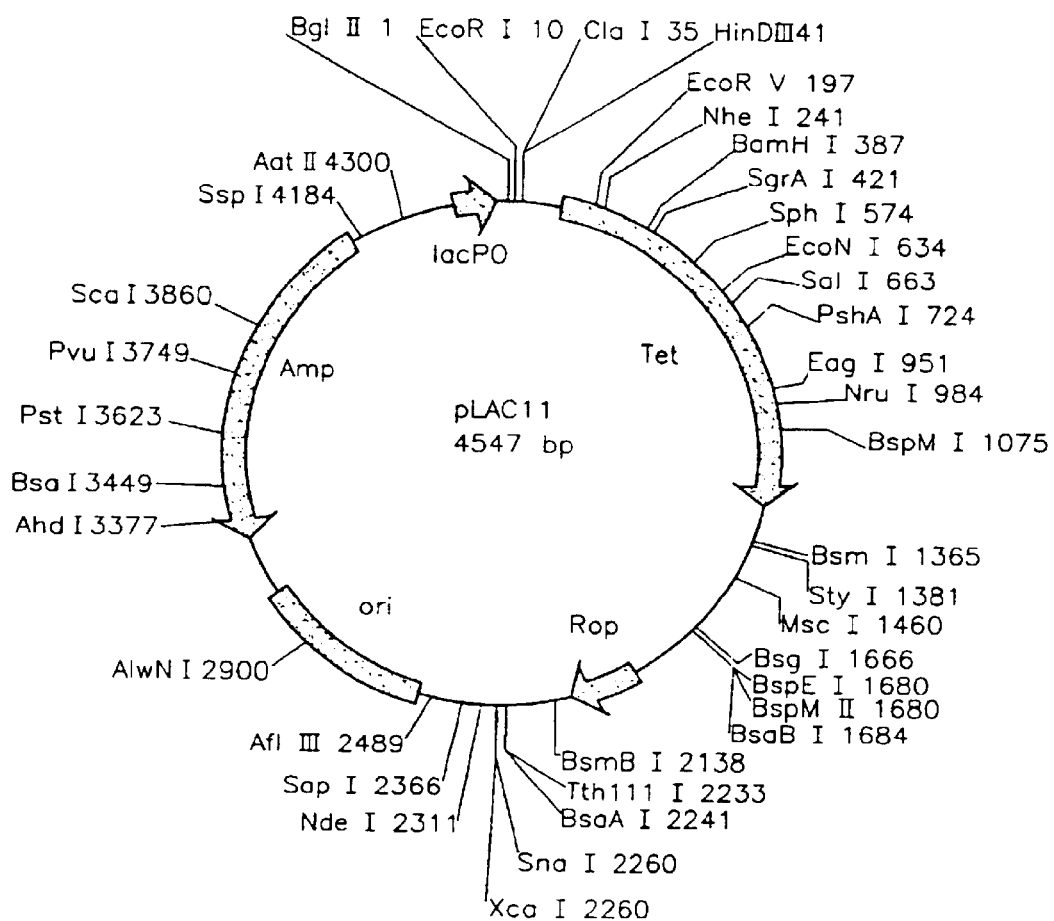
FIG. 2 is a map of plasmid pLAC11. The unique restriction sites and the base pair at which they cut are indicated. Other sites of interest are also shown, including Tet (98-1288), Rop (1931-2122), origin of replication (ori) (2551-3138), Amp (3309-4169), and lacPO (4424-4536).

The present invention represents a significant advance in the art of peptide drug development by allowing concurrent screening for peptide bioactivity and stability. Randomized recombinant peptides are screened for bioactivity in a tightly regulated inducible expression system, preferably derived from the wild-type lac operon, that permits essentially complete repression of peptide expression in the host cell. Subsequent induction of peptide expression can then be used to identify peptides that inhibit host cell growth or possess other bioactivities.

Intracellular screening of randomized peptides has many advantages over existing methods. Bioactivity is readily apparent, many diverse bioactivities can be screened for simultaneously, very large numbers of peptides can be screened using easily generated peptide libraries, and the host cell, if desired, can be genetically manipulated to identify an affected protein target. Advantageously, randomized peptides can be screened in a host cell that is identical to or closely resembles the eventual target cell for antimicrobial applications. An additional and very important feature of this system is that selection is naturally biased in favor of peptides that are stable in an intracellular environment, i.e., that are resistant to proteases and peptidases. Fortuitously, bacterial peptidases are very similar to eukaryotic peptidases. Peptides that are stable in a bacterial host are thus likely to be stable in a eukaryotic cell as well, allowing bacterial cells to be used in initial screens to identify drugs that may eventually prove useful as human or animal therapeutics.

The invention is directed to the identification and use of bioactive peptides. A bioactive peptide is a peptide having a biological activity. The term "bioactivity" as used herein includes, but is not limited to, any type of interaction with another biomolecule, such as a protein, glycoprotein, carbohydrate, for example an oligosaccharide or polysaccharide, nucleotide, polynucleotide, fatty acid, hormone, enzyme, cofactor or the like, whether the interactions involve covalent or noncovalent binding. Bioactivity further includes interactions of any type with other cellular components or constituents including salts, ions, metals, nutrients, foreign or exogenous agents present in a cell such as viruses, phage and the like, for example binding, sequestration or transport-related interactions. Bioactivity of a peptide can be detected, for example, by observing phenotypic effects in a host cell in which it is expressed, or by performing an in vitro assay for a particular bioactivity, such as affinity binding to a target molecule, alteration of an enzymatic activity, or the like. Examples of bioactive peptides include antimicrobial peptides and peptide drugs. Antimicrobial peptides are peptides that adversely affect a microbe such as a bacterium, virus, protozoan, or the like. Antimicrobial peptides include, for example, inhibitory peptides that slow the growth of a microbe, microbiocidal peptides that are effective to kill a microbe (e.g., bacteriocidal and virocidal peptide drugs, sterilants, and disinfectants), and peptides effective to interfere with microbial reproduction, host toxicity, or the like. Peptide drugs for therapeutic use in humans or other animals include, for example, antimicrobial peptides that are not prohibitively toxic to the patient, peptides designed to elicit, speed up, slow down, or prevent various metabolic processes in the host such as insulin, oxytocin, calcitonin, gastrin, somatostatin, anticancer peptides, and the like.

The term "peptide" as used herein refers to a plurality of amino acids joined together in a linear chain via peptide bonds. Accordingly, the term "peptide" as used herein includes a dipeptide, tripeptide, oligopeptide and polypeptide. A dipeptide contains two amino acids; a tripeptide contains three amino acids; and the term oligopeptide is typically used to describe peptides having between 2 and about 50 or more amino acids. Peptides larger than about 50 are often referred to as polypeptides or proteins. For purposes of the present invention, a "peptide" is not limited to any particular number of amino acids. Preferably, however, the peptide contains about 2 to about 50 amino acids, more preferably about 5 to about 40 amino acids, most preferably about 5 to about 20 amino acids.

The library used to transform the host cell is formed by cloning a randomized, peptide-encoding oligonucleotide into a nucleic acid construct having a tightly regulable expression control region. An expression control region can be readily evaluated to determine whether it is "tightly regulable," as the term is used herein, by bioassay in a host cell engineered to contain a mutant nonfunctional gene "X." Transforming the engineered host cell with an expression vector containing a tightly regulable expression control region operably linked to a cloned wild-type gene "X" will preserve the phenotype of the engineered host cell under repressed conditions. Under induced conditions, however, the expression vector containing the tightly regulable expression control region that is operably linked to the cloned wild-type gene "X" will complement the mutant nonfunctional gene X to yield the wild-type phenotype. In other words, a host cell containing a null mutation which is transformed with a tightly regulable expression vector capable of expressing the chromosomally inactivated gene will exhibit the null phenotype under repressed conditions; but when expression is induced, the cell will exhibit a phenotype indistinguishable from the wild-type cell. It should be understood that the expression control region in a tightly regulable expression vector of the present invention can be readily modified to produce higher levels of an encoded biopeptide, if desired (see, e.g., Example 1, below). Such modification may unavoidably introduce some "leakiness" into expression control, resulting in a low level of peptide expression under repressed conditions.

In a preferred embodiment, the expression control region of the inducible expression vector is derived from the wild-type E. coli lac promoter operator region. In a particularly preferred form, the expression vector contains a regulatory region that includes the auxiliary operator O3, the CAP binding region, the −35 promoter site, the −10 promoter site, the operator O1, the Shine-Dalgarno sequence for lacZ, and a spacer region between the end of the Shine-Dalgarno sequence and the ATG start of the lacZ coding sequence (see FIG. 1).

It is to be understood that variations in the wild-type nucleic acid sequence of the lac promoter/operator region can be tolerated in the expression control region of the preferred expression vector and are encompassed by the invention, provided that the expression control region remains tightly regulable as defined herein. For example, the −10 site of the wild-type lac operon (TATGTT) is weak compared to the bacterial consensus −10 site sequence TATAAT, sharing four out of six positions. It is contemplated that other comparably weak promoters are equally effective at the −10 site in the expression control region; a strong promoter is to be avoided in order to insure complete repression in the uninduced state. With respect to the −35 region, the sequence of the wild-type lac operon, TTTACA, is one base removed from the consensus −35 sequence TTGACA. It is contemplated that a tightly regulable lac operon-derived expression control region could be constructed using a weaker −35 sequence (i.e., one having less identity with the consensus −35 sequence) and a wild-type −10 sequence (TATAAT), yielding a weak promoter that needs the assistance of the CAP activator protein. Similarly, it is to be understood that the nucleic acid sequence of the CAP binding region can be altered as long as the CAP protein binds to it with essentially the same affinity. The spacer region between the end of the Shine-Dalgarno sequence and the ATG start of the lacZ coding sequence is typically between about 5 and about 10 nucleotides in length, preferably about 5 to about 8 nucleotides in length, more preferably about 7–9 nucleotides in length. The most preferred composition and length of the spacer region depends on the composition and length of Shine-Dalgarno sequence with which it is operably linked as well as the translation start codon employed (i.e., AUG, GUG, or UUG), and can be determined accordingly by one of skill in the art. Preferably the nucleotide composition of the spacer region is "AT rich"; that is, it contains more A's and T's than it does G's and C's.

In a preferred embodiment of the method of the invention, the expression vector has the identifying characteristics of pLAC11 (ATCC No. 207108). More preferably, the expression vector is pLAC11 (ATCC No. 207108).

As used in the present invention, the term "vector" is to be broadly interpreted as including a plasmid, including an episome, a viral vector, a cosmid, or the like. A vector can be circular or linear, single-stranded or double-stranded, and can comprise RNA, DNA, or modifications and combinations thereof. Selection of a vector or plasmid backbone depends upon a variety of characteristics desired in the resulting construct, such as selection marker(s), plasmid copy number, and the like. A nucleic acid sequence is "operably linked" to an expression control sequence in the regulatory region of a vector, such as a promoter, when the expression control sequence controls or regulates the transcription and/or the translation of that nucleic acid sequence. A nucleic acid that is "operably linked" to an expression control sequence includes, for example, an appropriate start signal (e.g., ATG) at the beginning of the nucleic acid sequence to be expressed and a reading frame that permits expression of the nucleic acid sequence under control of the expression control sequence to yield production of the encoded peptide. The regulatory region of the expression vector optionally includes a termination sequence, such as a codon for which there is no corresponding aminoacetyl-tRNA, thus ending peptide synthesis. Typically, when the ribosome reaches a termination sequence or codon during translation of the mRNA, the polypeptide is released and the ribosome-mRNA-tRNA complex dissociates.

An expression vector optionally includes one or more selection or marker sequences, which typically encode an enzyme capable of inactivating a compound in the growth medium. The inclusion of a marker sequence can, for example, render the host cell resistant to an antibiotic, or it can confer a compound-specific metabolic advantage on the host cell. Cells can be transformed with the expression vector using any convenient method known in the art, including chemical transformation, e.g., whereby cells are made competent by treatment with reagents such as $CaCl_2$; electroporation and other electrical techniques; microinjection and the like.

In embodiments of the method that make use of a tightly regulable expression system derived from the lac operon, the host cell is or has been genetically engineered or otherwise altered to contain a source of Lac repressor protein in excess of the amount produced in wild-type *E. coli*. A host cell that contains an excess source of Lac repressor protein is one that expresses an amount of Lac repressor protein sufficient to repress expression of the peptide under repressed conditions, i.e., in the absence of an inducing agent, such as isopropyl β-D-thiogalactoside (IPTG). Preferably, expression of Lac repressor protein is constitutive. For example, the host cell can be transformed with a second vector comprising a gene encoding Lac repressor protein, preferably lacI, more preferably $lacI^q$, to provide an excess source of Lac repressor protein in trans, i.e., extraneous to the tightly regulable expression vector. An episome can also serve as a trans source of Lac repressor. Another option for providing a trans source of Lac repressor protein is the host chromosome itself, which can be genetically engineered to express excess Lac repressor protein. Alternatively, a gene encoding Lac repressor protein can be included on the tightly regulable expression vector that contains the peptide-encoding oligonucleotide so that Lac repressor protein is provided in cis. The gene encoding the Lac repressor protein is preferably under the control of a constitutive promoter.

The invention is not intended to be limited in any way by the type of host cell used for screening. The host cell can be a prokaryotic or a eukaryotic cell. Preferred mammalian cells include human cells, of any tissue type, and can include cancer cells or hybridomas, without limitation. Preferred bacterial host cells include gram negative bacteria, such as *E. coli* and various Staphylococcus, Streptococcus and Enterococcus. Protozoan cells are also suitable host cells. In clear contrast to conventional recombinant protein expression systems, it is preferable that the host cell contains proteases and/or peptidases, since the selection will, as a result, be advantageously biased in favor of peptides that are protease- and peptidase-resistant. More preferably, the host cell has not been modified, genetically or otherwise, to reduce or eliminate the expression of any naturally expressed proteases or peptidases. The host cell can be selected with a particular purpose in mind. For example, if it is desired to obtain peptide drugs specific to inhibit Staphylococcus, peptides can be advantageously expressed and screened in Staphylococcus.

There is, accordingly, tremendous potential for the application of this technology in the development of new antibacterial peptides useful to treat various pathogenic bacteria. Of particular interest are pathogenic Staphylococci, Streptococci, and Enterococci, which are the primary causes of nosocomial infections. Many of these strains are becoming increasingly drug-resistant at an alarming rate. The technology of the present invention can be practiced in a pathogenic host cell to isolate inhibitor peptides that specifically target the pathogenic strain of choice. Inhibitory peptides identified using pathogenic microbial host cells in accordance with the invention may have direct therapeutic utility; based on what is known about peptide import, it is very likely that small peptides are rapidly taken up by Staphylococci, Streptococci, and Enterococci. Once internalized, the inhibitory peptides identified according to the invention would be expected to inhibit the growth of the bacteria in question. It is therefore contemplated that novel inhibitor peptides so identified can be used in medical treatments and therapies directed against microbial infection. It is further contemplated that these novel inhibitor peptides can be used, in turn, to identify additional novel antibacterial peptides using a synthetic approach. The coding sequence of the inhibitory peptides is determined, and peptides are then chemically synthesized and tested in the host cell for their inhibitory properties.

Novel inhibitor peptides identified in a pathogenic microbial host cell according to the invention can also be used to elucidate potential new drug targets. The protein target that the inhibitor peptide inactivated is identified using reverse genetics by isolating mutants that are no longer inhibited by the peptide. These mutants are then mapped in order to precisely determine the protein target that is inhibited. New antibacterial drugs can then be developed using various known or yet to be discovered pharmaceutical strategies.

Following transformation of the host cell, the transformed host cell is initially grown under conditions that repress expression of the peptide. Expression of the peptide is then induced. For example, when a lac promoter/operator system is used for expression, IPTG is added to the culture medium. A determination is subsequently made as to whether the peptide is inhibitory to host cell growth, wherein inhibition of host cell growth under induced but not repressed conditions is indicative of the expression of a bioactive peptide.

Notably, the bioactive peptides identified according to the method of the invention are, by reason of the method ifself, stable in the intracellular environment of the host cell. The method of the invention thus preferably identifies bioactive peptides that are resistant to protease and peptidases. Resistance to proteases and peptidases can be evaluated by measuring peptide degradation when in contact with appropriate cell extracts or purified peptidases and/or proteases, employing methods well-known in the art. A protease- or peptidase-resistant peptide is evidenced by a longer half-life in the presence of proteases or peptidases compared to a control peptide.

Randomized peptides used in the screening method of the invention can be optionally engineered according to the method of the invention in a biased synthesis to increase their stability by making one or both of the N-terminal or C-terminal ends more resistant to proteases and peptidases, and/or by engineering into the peptides a stabilizing motif.

In one embodiment of the screening method of the invention, the putative bioactive peptide is stabilized by adding a stabilizing group to the N-terminus, the C-terminus, or to both termini. To this end, the nucleic acid sequence that encodes the randomized peptide in the expression vector or the expression vector itself is preferably modified to encode a first stabilizing group comprising the N-terminus of the peptide, and a second stabilizing group comprising the C-terminus of the peptide.

The stabilizing group is a stable protein, preferably a small stable protein such as thioredoxin, glutathione sulfotransferase, maltose binding protein, glutathione reductase, or a four-helix bundle protein such as Rop protein, although no specific size limitation on the protein anchor is intended. Proteins suitable for use as stabilizing groups can be either naturally occurring or non-naturally occurring. They can be isolated from an endogenous source, chemically or enzymatically synthesized, or produced using recombinant DNA technology. Proteins that are particularly well-suited for use as stabilizing groups are those that are relatively short in length and form very stable structures in solution. Proteins having molecular weights of less than about 70 kD are preferred for use as a stabilizing groups; more preferably the molecular weight of the small stable protein is less than about 25 kD, most preferably less than about 12 kD. For example, E. coli thioredoxin has a molecular weight about 11.7 kD; E. coli glutathione sulfotransferase has a molecular weight of about 22.9 kD, and Rop from the ColE1 replicon has a molecular weight of about 7.2 kD; and maltose binding protein (without its signal sequence) is about 40.7 kD. The small size of the Rop protein makes it especially useful as a stabilizing group, fusion partner, or peptide anchor, in that it is less likely than larger proteins to interfere with the accessibility of the linked peptide, thus preserving its bioactivity. Rop's highly ordered anti-parallel four-helix bundle topology (after dimerization), slow unfolding kinetics (see, e.g., Betz et al, Biochemistry 36, 2450–2458 (1997)) also contribute to its usefulness as a peptide anchor according to the invention. Other proteins with similar folding kinetics and/or thermodynamic stability (e.g., Rop has a midpoint temperature of denaturation, $T_m$, of about 71° C., Steif et al., Biochemistry 32, 3867–3876 (1993)) are also preferred peptide anchors. Peptides or proteins having highly stable tertiary motifs, such as a four-helix bundle topology, are particularly preferred. etail below.

Alternatively, the stabilizing group can constitute one or more proline (Pro). Preferably, a proline dipeptide (Pro-Pro) is used as a stabilizing group, however although additional prolines may be included. The encoded proline(s) are typically naturally occurring amino acids. However, if and to the extent a proline derivative, for example a hydroxyproline or a methyl- or ethyl-proline derivative, can be encoded or otherwise incorporated into the peptide, those proline derivatives are also useful as stabilizing groups.

At the N-terminus of the peptide, the stabilizing group also can alternatively include an oligopeptide having the sequence Xaa-$Pro_m$-, wherein Xaa is any amino acid and m is greater than 0. Preferably, m can be about 1 to about 5 (e.g., m can be 2 or 3). Likewise, at the C-terminus of the peptide, the stabilizing group can alternative include an oligopeptide having the sequence -$Pro_m$-Xaa, wherein Xaa is any amino acid, and m is greater than 0. Preferably, n is about 1 to about 5; preferably n=2 or 3, more preferably, m=2. In a particularly preferred embodiment of the method of the invention, the nucleic acid sequence that encodes the randomized peptide in the expression vector is modified to encode each of a first stabilizing group comprising the N-terminus of the peptide, the first stabilizing group being selected from the group consisting of small stable protein, Pro-, Pro-Pro-, Xaa-Pro-, and Xaa-Pro-Pro-, and a second stabilizing group linked to the C-terminus of the peptide, the second stabilizing group being selected from the group consisting of a small stable protein, -Pro, -Pro-Pro, Pro-Xaa and Pro-Pro-Xaa. The resulting peptide has enhanced stability in the intracellular environment relative to a peptide lacking the terminal stabilizing groups.

In another preferred embodiment of the screening method of the invention, the expression vector encodes a four-helix bundle protein fused, at either the C-terminus or the N-terminus, to the randomized peptide. Preferably, the four-helix bundle protein is E. coli Rop protein or a homolog thereof. The non-fused terminus of the randomized peptide can, but need not, comprise a stabilizing group. The resulting fusion protein is predicted to be more stable than the randomized peptide itself in the host intracellular environment. Where the four-helix bundle protein is fused to the N-terminus, the randomized peptide can optionally be further stabilized by engineering one or more prolines, with or without a following undefined amino acid (e.g., -Pro, -Pro-Pro, -Pro-Xaa, -Pro-Pro-Xaa, etc.). at the C-terminus of the peptide sequence; likewise, when the four-helix bundle protein is fused to the C-terminus, the randomized peptide can be further stabilized by engineering one or more prolines, with or without a preceding undefined amino acid (e.g. Pro-, Pro-Pro-, Xaa-Pro, Xaa-Pro-Pro-, etc.) at the N-terminus of the peptide sequence.

In yet another embodiment of the screening method of the invention, the putative bioactive peptide is stabilized by engineering into the peptide a stabilizing motif such as an α-helix motif or an opposite charge ending motif. Chemical synthesis of an oligonucleotide according to the scheme [(CAG)A(TCAG)] yields an oligonucleotide encoding a peptide consisting of a random mixture of the hydrophilic amino acids His, Gln, Asn, Lys, Asp, and Glu (see Table 14). Except for Asp, these amino acids are most often associated with α-helical secondary structural motifs; the resulting oligonucleotides are thus biased in favor of oligonucleotides that encode peptides that are likely to form α-helices in solution. Alternatively, the putative bioactive peptide is stagilized by flanking a randomized region with a region of uniform charge (e.g., positive charge) on one end and a region of opposite charge (e.g., negative) on the other end, to form an opposite charge ending motif. To this end, the nucleic acid sequence that encodes the randomized peptide in the expression vector or the expression vector itself is preferably modified to encode a plurality of sequential uniformly charged amino acids comprising the N-terminus of the peptide, and a plurality of sequential oppositely charged amino acids comprising the C-terminus of the peptide. The positive charges are supplied by a plurality of positively charged amino acids consisting of lysine, histidine, arginine or a combination thereof; and the negative charges are supplied by a plurality of negatively charged amino acids consisting of aspartate, glutamate or a combination thereof. It is expected that such a peptide will be stabilized by the ionic interaction of the two oppositely charges ends. Preferably, the putative bioactive peptide contains at least three charged amino acids at each end. More preferably, it contains at least four charged amino acids at each end. In a particularly preferred embodiment, the larger acidic amion acid glutamate is paired with the smaller basic amino acid lysine, and the smaller acidic amino acid aspartate is paired with the larger basic amino acid arginine.

It is to be understood that novel bioactive peptide identified using the method for identification of bioactive peptides described herein are also included in the present invention.

The present invention further provides a bioactive peptide containing one or more structural features or motifs selected to enhance the stability of the bioactive peptide in an intracellular environment. During development and testing of the intracellular screening method of the present invention, it was surprisingly discovered that several bioactive peptides identified from the randomized peptide library shared particular structural features. For example, a disproportionately high number of bioactive peptides identified using the intracellular screening method contained one or more proline residues at or near a peptide terminus. A disproportionate number also contained sequences predicted, using structure prediction algorithms well-known in the art, to form secondary structures such as α helices or β sheets; or a hydrophobic membrane spanning domain. Bioactive fusion proteins comprising the randomized peptide sequence fused to the Rop protein, due to a deletion event in the expression vector, were also identified.

According, the invention provides a bioactive peptide having a stabilizing group at its N-terminus, its C-terminus, or at both termini. In a bioactive peptide stabilized at only one terminus (i.e., at either the N- or the C-terminus) the stabilizing group is preferably either a four-helix bundle protein, such as Rop protein, a proline (Pro), or a proline dipeptide (Pro-Pro). It should be understood that in any synthetic peptide having a stabilizing group that includes one or more prolines according to the present invention, the proline is preferably a naturally occurring amino acid; alternatively, it can be a synthetic derivative of proline, for example a hydroxyproline or a methyl- or ethyl-proline derivative. Accordingly, where the abbreviation "Pro" is used herein in connection with a stabilizing group that is part of a synthetic peptide, it is meant to include proline derivatives in addition to a naturally occurring proline.

A peptide stabilized at both termini includes a first stabilizing group comprising the N-terminus, and a second stabilizing group stabilizing the C-terminus, where the first and second stabilizing groups are as defined previously in connection with the method for identifying bioactive peptides. The stabilizing group is obviously attached to the peptide. The bioactive peptide of the invention includes a bioactive peptide that has been detectably labeled, derivatized, or modified in any manner desired prior to use, provided it contains one or more terminal stabilizing groups as provided herein. In one preferred embodiment of the bioactive peptide of the invention, the first stabilizing group, comprising the N-terminus, is Xaa-Pro-Pro-, Xaa-Pro-, Pro- or Pro-Pro-; and second stabilizing group, comprising the C-terminus, is Pro-Pro-Xaa, -Pro-Xaa, -Pro or -Pro-Pro; preferably -Pro-Pro. In another preferred embodiment, the first (N-terminal) stabilzing group is a small stable protein, preferably a four-helix bundle protein such as Rop protein; and the second (C-terminal) stabilizing group is Pro-Pro-Xaa, -Pro-Xaa, -Pro or -Pro-Pro; preferably -Pro-Pro. In yet another preferred embodiment, the second (C-terminal) stabilizing group is a small stable protein, preferably a four-helix bundle protein such as Rop protein, and the first (N-terminal) stabilizing group is Pro-, Pro-Pro-, Xaa-Pro- or Xaa-Pro-Pro-.

The invention further provides a peptide stabilized by flanking the amino acid sequence of a bioactive peptide with an opposite charge ending motif, as described herein. Preferably, the resulting stabilized peptide retains at least a portion of the biological activity of the bioactive protein. The stabilized peptide includes a peptide that has been detectably labeled, derivatized, or modified in any manner desired prior to use.

It should be understood that any bioactive peptide, without limitation, can be stabilized according to the invention by attaching a stabilizing group to either or both of the N- and C-termini, or by attaching oppositively charged groups to the N- and C-termini to form an opposite charge ending motif. Included in the present invention are any and various antimicrobial peptides, inhibitory peptides, therapeutic peptide drugs, and the like as, for example and with limitation, those listed in Tables 1 and 2, that have been modified at one or both peptide termini to include a stabilizing group, for example a four-helix bundle protein such as Rop protein, proline (Pro-), a proline-proline dipeptide (Pro-Pro-), an Xaa-Pro- dipeptide, or an Xaa-Pro-Pro-tripeptide at the N-terminus, and/or a four-helix bundle protein such as Rop protein, proline (-Pro), or a proline-proline dipeptide (-Pro-Pro), a Pro-Xaa dipeptide, or a Pro-Pro-X tripeptide at the C-terminus; or that have been modified to contain an opposite charge ending motif according to the invention. In this aspect the invention is exemplified by peptides such as Pro-Pro-Asp-Arg-Val-Tyr-Ile-His-Pro-Phe-His-Ile-Pro-Pro (SEQ ID NO: 3) and Glu-Asp-Glu-Asp-Asp-Arg-Val-Tyr-Ile-His-Pro-Phe-His-Ile-Arg-Lys-Arg-Lys (SEQ ID NO: 4), wherein the middle nine amino acids (Asp-Arg-Val-Tyr-Ile-His-Pro-Phe-His-Ile-; SEQ ID NO: 5) constitute the sequence of angiotensin.

Modification of a bioactive peptide to yield a stabilized bioactive peptide according to the invention can be achieved by standard techniques well-known in the arts of genetics and peptide synthesis. For example, where the peptide is synthesized de novo, as in solid state peptide synthesis, one or more prolines can be added at the beginning and the end of the peptide chain during the synthetic reaction. In recombinant synthesis, for example as described in Example III herein, one or more codons encoding proline can be inserted into the peptide coding sequence at the beginning and or the end of the sequence, as desired. Preferably, codons encoding N-terminal prolines are inserted after (i.e., 3' to) the initiation site ATG (which encodes methionine). Analogous techniques are used to synthesize bioactive peptides having an opposite charge ending motif. When a known bioactive peptide is modified to yield a stabilized bioactive peptide according to the invention, the unmodified peptide can conveniently be used as a control in a protease- or peptidase-resistance assay as described hereinabove to confirm, if desired, that the modified peptide exhibits increased stability.

The present invention also provides a cleavable polypeptide comprising a stabilized, bioactive peptide either immediately preceded by (i.e., adjacent to the N-terminus of the bioactive peptide) a cleavage site, or immediately followed by (i.e., adjacent to the C-terminus of the bioactive peptide) a cleavage site. Thus, a bioactive peptide as contemplated by the invention can be part of a cleavable polypeptide. The cleavable polypeptide is cleavable, either chemically, as with cyanogen bromide, or enzymatically, to yield the bioactive peptide. The resulting bioactive peptide either includes a first stabilizing group comprising its N-terminus and a second stabilizing group positioned at its C-terminus, or it includes an opposite charge ending motif, both as described hereinabove. The cleavage site immediately precedes the N-terminal stabilizing group or immediately follows the C-terminal stabilizing group. In the case of a bioactive peptide having an opposite charge ending motif, the cleavage site immediately precedes the first charged region or immediately follows the second charged region. The cleavage site makes it possible to administer a bioactive peptide in a form that could allow intracellular targeting and/or activation.

Alternatively, a bioactive peptide of the invention can be fused to a noncleavable N-terminal or C-terminal targeting sequence wherein the targeting sequence allows targeted delivery of the bioactive peptide, e.g., intracellular targeting or tissue-specific targeting of the bioactive peptide. In one embodiment of this aspect of the invention, the free terminus of the bioactive peptide as described a stabilizing group as described hereinabove in connection with the screening method for identifying bioactive peptides, for example one or more prolines. The targeting sequence forming the other peptide terminus can, but need not, contain a small stable protein such as Rop or one or more proline comprising its terminus, as long as the targeting function of the targeting sequence is preserved. In another embodiment of this aspect of the invention, the bioactive peptide comprises a charge ending motif as described hereinabove, wherein one charged region occupies the free terminus of the bioactive peptide, and the other charged region is disposed between the targeting sequence and the active sequence of the bioactive peptide.

The invention further includes a method for using an antimicrobial peptide that includes covalently linking a stabilizing group, as described above, to the N-terminus, the C-terminus, or to both termini, to yield a stabilized antimicrobial peptide, then contacting a microbe with the stabilized antimicrobial peptide. Alternatively, the stabilized antimicrobial peptide used in this aspect of the invention is made by covalently linking oppositely charged regions, as described hereinabove, to each end of the antimicrobial peptide to form an opposite charge ending motif. An antimicrobial peptide is to be broadly understood as including any bioactive peptide that adversely affects a microbe such as a bacterium, virus, protozoan, or the like, as described in more detail hereinabove. An example of an antimicrobial peptide is an inhibitory peptide that inhibits the growth of a microbe. When the antimicrobial peptide is covalently linked to a stabilizing group at only one peptide terminus, any of the stabilizing groups described hereinabove can be utilized. When the antimicrobial peptide is covalently linked to a stabilizing group at both peptide termini, the method includes covalently linking a first stabilizing group to the N-terminus of the antimicrobial peptide and a second stabilizing group to the C-terminus of the antimicrobial peptide, where the first and second stabilizing groups are as defined previously in connection with the method for identifying bioactive peptides. In a preferred embodiment of the method for using an antimicrobial peptide, one or more prolines, more preferably a proline-proline dipeptide, is attached to at least one, preferably both, termini of the antimicrobial peptide. Alternatively, or in addition, an Xaa-Pro- or an Xaa-Pro-Pro sequence, can be attached to the N-terminus of a microbial peptide, and/or a Pro-Xaa or a Pro-Pro-Xaa sequence can be attached to the C-terminus, to yield a stabilized antimicrobial peptide.

The antimicrobial peptide thus modified in accordance with the invention has enhanced stability in the intracellular environment relative to an unmodified antimicrobial peptide. As noted earlier, the unmodified peptide can conveniently be used as a control in a protease- or peptidase-resistance assay as described hereinabove to confirm, if desired, that the modified peptide exhibits increased stability. Further, the antimicrobial activity of the antimicrobial peptide is preferably preserved or enhanced in the modified antimicrobial peptide; modifications that reduce or eliminate the antimicrobial activity of the antimicrobial peptide are easily detected and are to be avoided.

The invention further provides a method for inhibiting the growth of a microbe comprising contacting the microbe with a stabilized inhibitory peptide. In one embodiment of this aspect of the invention, the stabilized inhibitory peptide has a stabilizing group at the N-terminus, the C-terminus, or to both. Preferably, the inhibitory peptide has a first stabilizing group comprising the N-terminus of the inhibitory peptide, and a second stabilizing group comprising the C-terminus of the inhibitory peptide; the first and second stabilizing groups are as defined previously in connection with the method for identifying bioactive peptides. In another embodiment of this aspect of the invention, the inhibitory peptide is stabilized by the addition of oppositely charged regions to each end to form an opposite charge ending motif, as described hereinabove.

Also included in the present invention is a method for treating a patient having a condition treatable with a peptide drug, comprising administering to the patient a peptide drug that has been stabilized as described herein. Peptide drugs for use in therapeutic treatments are well known (see, e.g., Table 1). However, they are often easily degraded in biological systems, which affects their efficacy. In one embodiment of the present method, the patient is treated with a stabilized drug comprising the peptide drug of choice and a stabilizing group attached to either the N-terminus, the C-terminus of, or to both termini of the peptide drug. In another embodiment of the present method, the patient is treated with a stabilized drug comprising the peptide drug of choice and stabilized by attachment of oppositely charged regions to both termini of the peptide drug. Because the peptide drug is thereby stabilized against proteolytic degradation, greater amounts of the drug should reach the intended target in the patient.

In embodiments of the method involving administration of a peptide drug that is covalently linked to a stabilizing group at only one peptide terminus, the stabilizing group is preferably an four-helix bundle protein such as a Rop protein, provided that attachment of the four-helix bundle protein to the peptide terminus preserves a sufficient amount of efficacy for the drug. It is to be nonetheless understood that the group or groups used to stabilize the peptide drug are as defined hereinabove, without limitation. In embodiments involving administration of a peptide drug covalently linked to a stabilizing group at both peptide termini, the peptide drug includes a first stabilizing group comprising the N-terminus of the peptide drug and a second stabilizing group linked to the C-terminus of the peptide drug. Thus, in another preferred embodiment of the treatment method of the invention, the stabilized peptide drug includes one or more prolines, more preferably a proline-proline dipeptide, attached to one or both termini of the peptide drug. For example, the peptide drug can be stabilized by covalent attachment of a Rop protein at one terminus, and by a proline or proline dipeptide at the other terminus; in another preferred embodiment, the peptide drug can be stabilized by proline dipeptides at each of the N-terminus and C-terminus. Alternatively, or in addition, the stabilized peptide drug used in the treatment method can include an Xaa-Pro- or an Xaa-Pro-Pro- sequence at the N-terminus of the peptide drug, and/or a -Pro-Xaa or a -Pro-Pro-Xaa sequence at the C-terminus. Optionally, prior to administering the stabilized peptide drug, the treatment method can include a step comprising covalently linking a stabilizing group to one or both termini of the peptide drug to yield the stabilized peptide drug.

If desired, the unmodified peptide drug can conveniently be used as a control in a protease- or peptidase-resistance assay as described hereinabove to confirm that the stabilized peptide drug exhibits increased stability. Further, the therapeutic efficacy of the peptide drug is preferably preserved or enhanced in the stabilized peptide drug; modifications that reduce or eliminate the therapeutic efficacy of the peptide drug are easily detected and are to be avoided.

The present invention further includes a fusion protein comprising a four-helix bundle protein, preferably Rop protein, and a polypeptide. Preferably the polypeptide is bioactive; more preferably it is a bioactive peptide. The fusion protein of the invention can be used in any convenient expression vector known in the art for expression or overexpression of a peptide or protein of interest. Optionally, a cleavage site is present between the four helix bundle protein and the polypeptide to allow cleavage, isolation and purification of the polypeptide. In one embodiment of the fusion protein, the four-helix bundle protein is covalently linked at its C-terminus to the N-terminus of the polypeptide; in an alternative embodiment, the four-helix bundle protein is covalently linked at its N-terminus to the C-terminus of the polypeptide. Fusion proteins of the invention, and expression vectors comprising nucleic acid sequences encoding fusion proteins wherein the nucleic acid sequences are operably linked to a regulatory control element such as a promoter, are useful for producing or overproducing any peptide or protein of interest.

EXAMPLES

The present invention is illustrated by the following examples. It is to be understood that the particular examples, materials, amounts, and procedures are to be interpreted broadly in accordance with the scope and spirit of the invention as set forth herein.

Example I
Construction and Characterization of a Highly Regulable Expression Vector, pLAC11, and its Multipurpose Derivatives, pLAC22 and pLAC33

A number of different expression vectors have been developed over the years to facilitate the production of proteins in *E. coli* and related bacteria. Most of the routinely employed expression vectors rely on lac control in order to overproduce a gene of choice. While these vectors allow for overexpression of the gene product of interest, they are leaky due to changes that have been introduced into the lac control region and gene expression can never be shut off under repressed conditions, as described in more detail below. Numerous researchers have noticed this problem with the more popular expression vectors pKK223-3 (G. Posfai et al. Gene. 50: 63–67 (1986); N. Scrutton et al., Biochem J. 245: 875–880 (1987)), pKK233-2 (P. Beremand et al., Arch Biochem Biophys. 256: 90–100 (1987); K. Ooki et al., Biochemie. 76: 398–403 (1994)), pTrc99A (S. Ghosh, Protein Expr. Purif. 10: 100–106 (1997); J. Ranie et al., Mol. Biochem. Parasitol. 61: 159–169 (1993)), as well as the PET series (M. Eren et al., J. Biol. Chem. 264: 14874–14879 (1989); G. Godson, Gene 100: 59–64 (1991)).

The expression vector described in this example, pLAC11, was designed to be more regulable and thus more tightly repressible when grown under repressed conditions. This allows better regulation of cloned genes in order to conduct physiological experiments. pLAC11 can be used to conduct physiologically relevant studies in which the cloned gene is expressed at levels equal to that obtainable from the chromosomal copy of the gene in question. The expression vectors described here were designed utilizing the wild-type lac promoter/operator in order to accomplish this purpose and include all of the lac control region, without modification, that is contained between the start of the O3 auxiliary operator through the end of the O0 operator. As with all lac based vectors, the pLAC11 expression vector described herein can be turned on or off by the presence or absence of the gratuitous inducer IPTG. In experiments in which a bacterial cell contained both a null allele in the chromosome and a second copy of the wild-type allele on pLAC11 cells grown under repressed conditions exhibited the null phenotype while cells grown under induced conditions exhibited the wild-type phenotype. Thus the pLAC11 vector truly allows for the gene of interest to be grown under either completely repressed or fully induced conditions. Two multipurpose derivatives of pLAC11, pLAC22 and pLAC33 were also constructed to fulfill different experimental needs.

The vectors pLAC11, pLAC22 and pLAC33 were deposited with the American Type Culture Collection (ATCC), 10801 University Blvd., Manassas, Va., 20110-2209, USA, on Feb. 16, 1999, and assigned ATCC deposit numbers ATCC 207108, ATCC 207110 and ATCC 207109, respectively. It is nonetheless to be understood that the written description herein is considered sufficient to enable one skilled in the art to fully practice the present invention. Moreover, the deposited embodiment is intended as a single illustration of one aspect of the invention and is not to be construed as limiting the scope of the claims in any way.

MATERIALS AND METHODS

Media. Minimal M9 media (6 g disodium phosphate, 3 g potassium phosphate, 1 g ammonium chloride, 0.5 g sodium chloride, distilled water to 1 L; autoclave; add 1 mL m magnesium sulfate (1M) and 0.1 mL calcium chloride (1M); a sugar added to a final concentration of 0.2%; vitamins and amino acids as required for non-prototrophic strains) and rich LB media (10 g tryptone, 5 g yeast extract, 10 g sodium chloride, distilled water to 1 L; autoclave) were prepared as described by Miller (J. Miller, "Experiments in molecular genetics" Cold Spring Harbor Laboratory, Cold Spring Harbor, N.Y. (1972). The antibiotics ampicillin, kanamycin, streptomycin, and tetracycline (Sigma Chemical Company, St. Louis, Mo.) were used in rich media at a final concentration of 100, 40, 200, and 20 ug/ml, respectively. When used in minimal media, tetracycline was added at a final concentration of 10 ug/ml. 5-bromo-4-chloro-3-indoyl β-D-galactopyranoside (Xgal) was added to media at a final concentration of 40 ug/ml unless otherwise noted. IPTG was added to media at a final concentration of 1 mM.

Chemicals and Reagents. When amplified DNA was used to construct the plasmids that were generated in this study, the PCR reaction was carried out using native Pfu polymerase from Stratagene (Cat. No. 600135). Xgal and IPTG were purchased from Diagnostic Chemicals Limited.

Bacterial Strains and Plasmids. Bacterial strains and plasmids are listed in Table 4. To construct ALS225, ALS224 was mated with ALS216 and streptomycin resistant, blue recombinants were selected on a Rich LB plat that contained streptomycin, Xgal, and IPTG. To construct ALS226, ALS224 was mated with ALS217 and streptomycin resistant, kanomycin resistant recombinants were selected on a Rich LB plate that contained streptomycin and kanamycin. To construct ALS535, ALS534 was mated with ALS498 and tetracycline resistant recombinants recombinants were selected on a Minimal M9 Glucose plate that contained tetracycline, leucine and thiamine ($B_1$) (Sigma Chemical Company). To construct ALS533, a P1 lysate prepared from *E. coli* strain K5076 (H. Miller et al., Cell 20: 711–719 (1980)) was used to transduce ALS224 and tetracycline resistant transductants were selected.

TABLE 4

Bacterial strains and plasmids used in Example 1

E. coli Strains

| Laboratory Name | Original Name | Genotype | Source |
|---|---|---|---|
| ALS216 | SE9100 | araD139 Δ(lac)U169 thi flbB5301 deoC7 ptsF25 rpsE/F'lacI$^q$ Z$^+$Y$^+$A$^+$ | E. Altman et al. J Biol Chem. 265:18148–18153 (1998) |
| ALS217 | SE9100.1 | araD139 Δ(lac)U169 thi flbB5301 deoC7 ptsF25 rpsE/F'lacI$^q$ Z::Tn5 Y$^+$A$^+$ | S. Emr (Univ. of California, San Diego) |
| ALS221 | BL21(DE3) | ompT hsd5(b)(R-M-) gal dem | F. Studier et al. J Mol Biol. 189:113–130 (1986) |
| ALS224 | MC1061 | araD139 Δ(araABOIC-leu)7679 Δ(lac)X74 galU galK rpsL hsr– hsm+ | M. Casadaban et al. J Mol Biol 138:179–207 (1980) |
| ALS225 |  | MC1061/F'lacI$^q$ Z$^+$Y$^+$A$^+$ | This example |
| ALS226 |  | MC1061/F'lacI$^q$ Z::Tn5 Y$^+$A$^+$ | This example |
| ALS269 | CSH27 | F-trpA33 thi | J. Miller, "Experiments in molecular genetics" Cold Spring Harbor Laboratory, Cold Spring Harbor, N.Y. (1972) |
| ALS413 | MG1655 | E. coli wild-type F-γ- | M. Guyer et al., Cold Spring Syrup Quant Biol 45:135–140 (1980) |
| ALS498 | JM101 | supE thi Δ(lac-proAB)/F'traD36 proA$^+$B$^+$ lacI$^q$ Δ(lacZ)M15 | C. Yanisch-Perron et al., Gene 33:103–119 (1985) |
| ALS514 | NM554 | MC1061 recA13 | E. Raleigh et al., Nucl. Acids Res. 16:1563–1575 (1988). |
| ALS515 |  | MC1061 recA13/F'lacI$^q$ Z$^+$Y$^+$A$^+$ | This example |
| ALS524 | XL1-Blue | recA1 endA1 gyrA96 thi-1 hsdR17 supE44 relA1lac/F'proAB lacI$^q$ Δ(lacZ)M15 Tn10 | Stratagene (Cat. No. 200268) |
| ALS527 |  | MC1061/F'proAB lacI$^q$ Δ(lacZ)M15 Tn10 | This example |
| ALS533 |  | MC1061 proAB::Tn10 | This example |
| ALS535 |  | MC1061 proAB::Tn10/F'lacI$^q$ Δ(lacZ)M15 proA$^+$B$^+$ | This example |
| ALS598 | CAG18615 | zjb-3179::Tn10dKan lambda-rph-1 | M. Singer et al., Microbiol. Rev. 53:1–24 (1989) |

Plasmids

| Plasmid Name | Relevant Characteristics | Source |
|---|---|---|
| pBH20 | wild-type lac promoter/operator, Amp$^R$,Tet$^R$, colE1 replicon | K. Itakura et al., Science, 198: 1056–1063 (1977) |
| pBR322 | Amp$^R$, Tet$^R$, colE1 replicon | F. Bolivar et al., Gene. 2:95–113 (1977) |
| pET-21(1) | T7 promoter/lac operator, lacI$^q$,Amp$^R$, colE1 replicon | Novagen (Cat No. 69770-1) |
| pGE226 | wild-type recA gene, Amp$^R$ | J. Weisemann, et al., J. Bacteriol. 163:748–755 (1985) |
| pKK223-3 | lac promoter/operator, Amp$^R$, colE1 replicon | J. Brosius et al., Proc. Natl. Acad. Sci. USA. 81:6929–6933 (1984) |
| pKK233-2 | trc promoter/operator, Amp$^R$, colE1 replicon | E. Amann et al., Gene. 40:183–190 (1985) |
| pLysE | T7 lysozyme, Cam$^R$, P15A replicon | F. Studier, J. Mol. Biol. 219:37–44 (1991) |
| pLysS | T7 lysozyme, Cam$^R$, P15A replicon | F. Studier, J. Mol. Biol. 219:37–44 (1991) |
| pMS421 | wild-type lac promoter/operator, lacI$^q$, Strep$^R$, Spec$^R$, SC101 replicon | D. Graha et al., Genetics. 120:319–327 (1988) |
| pTer7 | wild-type lacZ coding region. Amp$^R$ | R. Young (Texas A&M University) |
| pTre$^{99}$A | trc promoter/operator, lacI$^q$, Amp$^R$, colE1 replicon | E. Amann et al., Gene. 69:301–315 (1988) |
| pUC8 | lac promoter/operator, Amp$^R$, colE1 replicon | J. Vieira et al., Gene. 19:259–268 (1982) |
| pXE60 | wild-type TOL pWWO xylE gene. Amp$^R$ | J. Westpheling (Univ. of Georgia) |

Construction of the pLAC11, pLAC22, and pLAC33 expression vectors. To construct pLAC11, primers #1 and #2 (see Table 5) were used to polymerase chain reaction (PCR) amplify a 952 base pair (bp fragment from the plasmid pBH20 which contains the wild-type lac operon. Primer #2 introduced two different base pair mutations into the seven base spacer region between the Shine Dalgarno site and the ATG start site of the lacZ which converted it from AA<u>CA</u> <u>GC</u>T to AA<u>GA</u><u>T</u>CT thus placing a Bgl II site in between the Shine Dalgarno and the start codon of the lacZ gene. The resulting fragment was gel isolated, digested with Pst I and EcoR I, and then ligated into the 3614 bp fragment from the plasmid pBR322-AvaI which had been digested with the same two restriction enzymes. To construct pBR322-AvaI, pBR322 was digested with AvaI, filled in using Klenow, and then religated. To construct pLAC22, a 1291 bp Nco I. EcoR I fragment was gel isolated from pLAC21 and ligated to a 4361 bp Nco I. EcoR I fragment which was gel isolated from pBR322/NcoI. To construct pLAC21, primers #2 and #3 (see Table 5) were used to PCR amplify a 1310 bp fragment from the plasmid pMS421 which contains the wild-type lac operon as well as the lacI$^q$ repressor. The resulting fragment was gel isolated, digested with EcoR I, and then ligated into pBR322 which had also been digested with EcoR I. To construct pBR322/Nco I, primers #4 and #5 (see Table 5) were used to PCR amplify a 788 bp fragment from the plasmid pBR322. The resulting fragment was gel isolated, digested with Pst I and EcoR l, and then ligated into the 3606 bp fragment from the plasmid pBR322 which had been digested with the same two restriction enzymes. The pBR322/Nco I vector also contains added Kpn I and Sma I sites in addition to the new Nco I site. To construct pLAC33, a 2778 bp fragment was gel isolated from pLAC12 which had been digested with BsaB I and Bsa I and ligated to a 960 bp fragment from pUC8 which had been digested with Afl III, filled in with Klenow, and then digested with Bsa I. To construct pLAC12, a 1310 bp Pst I, BamH I fragment was gel isolated from pLAC11 and ligated to a 3232 bp Pst I, BamH I fragment which was gel isolated from pBR322.

from pBR322/Nco I; and bp 4377–5652 are bp 2–1277 from the wild-type *E. coli* lac operon (GenBank Accession #J01636), except that bp #4391 of the pLAC22 sequence or bp#16 from the wild-type *E. coli* lac operon sequence has been changed from a "C" to a "T" to reflect the presence of the lacI$^q$ mutation (J. Brosius et al., Proc. Natl. Acad. Sci. USA. 81:6929–6933 (1984)).

The sequence for the pLAC33 vector which is 3742 bp can be compiled as follows: bp 1–15 is AGATCTTAT-

TABLE 5

Primers employed to PCR amplify DNA fragments that were used in the construction of the various plasmids described in Example 1

```
pLAC11 and pLAC22
2 (for)    GTT GCC ATT GCT GCA GGC AT                            (SEQ ID NO: 6)
2 (rev)    ATT GAA TTC ATA AGA TTT TTC CTG TGT GAA ATT GTT ATC   (SEQ ID NO: 7)
CGT
3 (for)    ATT GAA TTC ACC ATG GAT ACC ATT GAA TGG TGC AAA A     (SEQ ID NO: 8)

pBR322/Nco I
4 (for)    GTT GTT GCC ATT GTT GCA 3                             (SEQ ID NO: 9)
5 (rev)    TGT ATG AAT TCC CGG GTA CCA TGG TTG AAG ACG AAA GGG   (SEQ ID NO: 10)
CCT C Bgl II - lacZ - Hind III
6 (for)    TAC TAT AGA TCT ATG ACC ATG ATT ACG GAT TCA CTG       (SEQ ID NO: 11)
7 (rev)    TAC ATA AAG CTT GGC CTG CCC GGT TAT TAT TAT TTT       (SEQ ID NO: 12)

Pst I - lacZ - Hind III
8 (for)    TAT CAT CTG CAG AGG AAA CAG CTA TGA CCA TGA TTA CGG   (SEQ ID NO: 13)
ATT CAC TG
9 (rev)    TAC ATA CTC GAG CAG GAA AGC TTG GCC TGC CCG GTT ATT   (SEQ ID NO: 14)
ATT ATT TT BamH 1 - lacZ - Hind III (also uses primer #9)
10 (for)   TAT CAT GGA TCC AGG AAA CAG CTA TGA CCA TGA TTA CGG   (SEQ ID NO: 15)
ATT CAC TG Bgl II - recA - Hind III
11 (for)   TAC TAT AGA TCT ATG GCT ATC GAC GAA AAC AAA CAG       (SEQ ID NO: 16)
12 (rev)   ATA TAT AAG CTT TTA AAA ATC TTC GTT AGT TTC TGC TAC   (SEQ ID NO: 17)
G Bam 1 - xylE - EcoR I
13 (for)   TAC TAT AGA TCT ATG AAC AAA GGT GTA ATG CGA CC        (SEQ ID NO: 18)
14 (rev)   ATT AGT GAA TTC GCA CAA TCT CTG CAA TAA GTC GT        (SEQ ID NO: 19)
```

In Table 5 the regions of the primers that are homologous to the DNA target template are indicated with a dotted underline, while the relevant restriction sites are indicated with a solid underline. All primers are listed in the 5'→3' orientation.

Compilation of the DNA sequences for the pLAC11, pLAC22, and pLAC33 expression vectors. All of the DNA that is contained in the pLAC11, pLAC22, and, pLAC33 vectors has been sequenced.

The sequence for the pLAC11 vector, which is 4547 bp, can be compiled as follows: bp 1–15 are AGATCTTAT-GAATTC (SEQ ID NO:20) from primer #2 (Table 5); bp 16–1434 are bp 4–1422 from pBR322 (GenBank Accession #J01749); bp 1435–1442 are TCGGTCGG, caused by filling in the Ava I site in pBR322ΔAvaI; bp 1443–4375 is bp 1427–4359 from pBR322 (GenBank Accession #J01749); and bp 4376–4547 are bp 1106–1277 from the wild-type *E. coli* lac operon (GenBank Accession #J01636).

The sequence for the pLAC22 vector which is 5652 bp can be compiled as follows: bp 1–15 are AGATCTTAT-GAATTC (SEQ ID NO:21) from primer #2 (Table 5); bp 16–4370 are bp 4–4358 from pBR322 (GenBank Accession #J01749); bp 4371–4376 is CCATGG which is the Nco I site GAATTC (SEQ.ID NO:22) from primer #2 (Table 5); bp 16–1684 are bp 4–1672 from pBR322 (GenBank Accession #J01749); bp 1685–2638 are bp 786–1739 from pUC8 (GenBank Accession #L09132); bp 2639–3570 are bp 3428–4359 from pBR322 (GenBank Accession #J01749); and bp 3571–3742 are bp 1106–1277 from the wild-type *E. coli* lac operon (GenBank Accession #J01636). In the maps for these vectors, the ori is identified as per Balbás (P. Balbás et al., Gene. 50:3–40 (1986)), while the lacPO is indicated starting with the O3 auxiliary operatic and ending with the O1 operator as per Müller-Hill (B. Müller-Hill, *The lac Operon: A Short History of a Genetic Paradigm*. Walter de Gruyter, Berlin, Germany (1996)).

Construction of the pLAC11-, pLAC22-, pLAC33-, pKK223-3-, pKK233-2-, pTrc99A-, and pET-21(+)-lacZ constructs. To construct pLAC11-lacZ, pLAC22-lacZ, and pLAC33-lacZ, primers #6 and #7 (see Table 5) were used to PCR amplify a 3115 bp fragment from the plasmid pTer7 which contains the wild-type lacZ gene. The resulting fragment was gel isolated, digested with Bgl II and Hind III, and then ligated into the pLAC11, pLAC22 or pLAC33 vectors which had been digested with the same two restriction enzymes. To construct pKK223-3-lacZ and pKK233-2-lacZ, primers #8 and #9 (see Table 5) were used to PCR amplify a 3137 bp fragment from the plasmid pTer7. The resulting fragment was gel isolated, digested with Pst I and Hind III, and then ligated into the pKK223-3 or pKK233-2 vectors which had been digested with the same two restriction enzymes. To construct pTrc99A-lacZ and pET-21(+)-lacZ, primers #9 and #10 (see Table 5) were used to PCR amplify a 3137 bp fragment from the plasmid pTer7. The resulting fragment was gel isolated, digested with BamH I and Hind III, and then ligated into the pTrc99A or pET-21(+) vectors which had been digested with the same two restriction enzymes.

Construction of the pLAC11-recA and xylE constructs. To construct pLAC11-recA, primers #11 and #12 (see Table 5) were used to PCR amplify a 1085 bp fragment from the plasmid pGE226 which contains the wild-type recA gene. The resulting fragment was gel isolated, digested with Bgl II and Hind III, and then ligated into the pLAC11 vector which had been digested with the same two restriction enzymes. To construct pLAC11-xylE, primers #13 and #14 (see Table 5) were used to PCR amplify a 979 bp fragment from the plasmid pXE60 which contains the wild-type *Pseudomonas putida* xylE gene isolated from the TOL pWWO plasmid. The resulting fragment was gel isolated, digested with Bgl II and EcoR I, and then ligated into the pLAC11 vector which had been digested with the same two restriction enzymes.

Assays. β-galactosidase assays were performed as described by Miller (J. Miller, "Experiments in molecular genetics," Cold Spring Harbor Laboratory, Cold Spring Harbor, N.Y. (1972)), while catechol 2,3-dioxygenase (catO2ase) assays were performed as described by Zukowski, et. al. (M. Zukowski et al., Proc. Natl. Acad. Sci. U.S.A. 80:1101–1105 (1983)).

RESULTS

Figure 3:
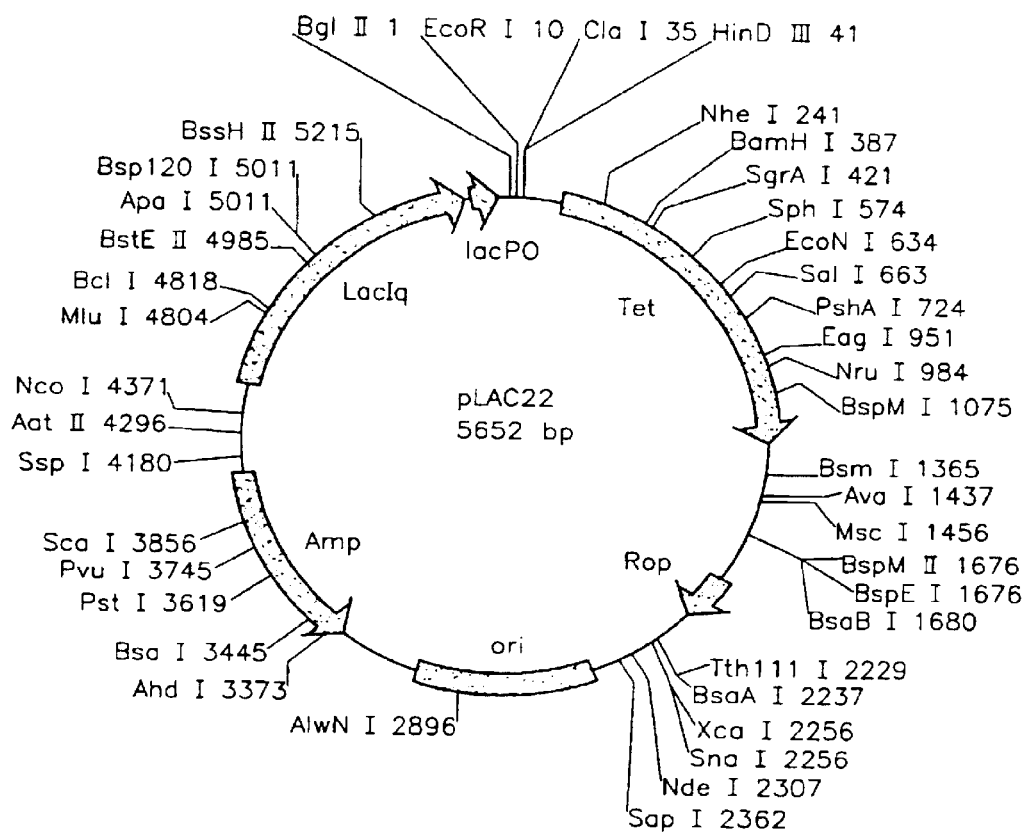
FIG. 3 is a map of plasmid pLAC22. The unique restriction sites and the base pair at which they cut are indicated. Other sites of interest are also shown, including Tet (98-1288), Rop (1927-2118), ori (2547-3134), Amp (3305-4165), lacI$^q$ (4452-5536), and lacPO (5529-5641).
Figure 4:
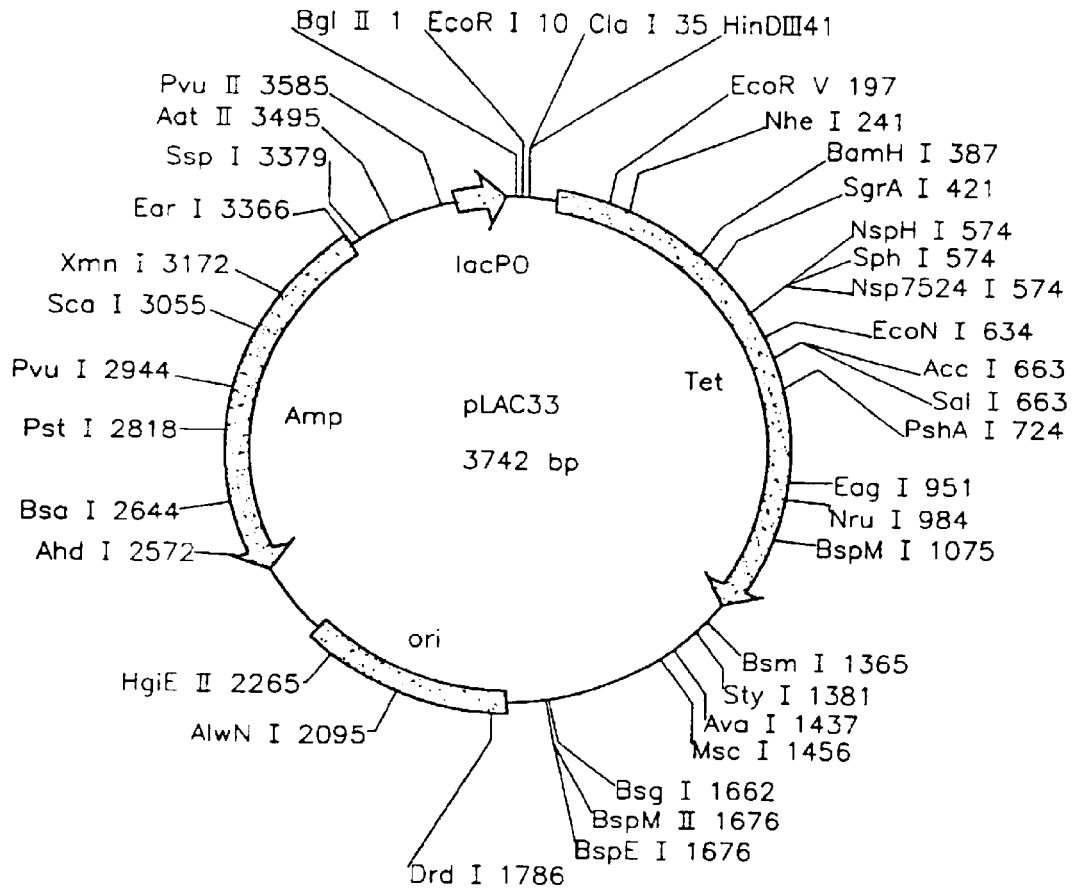
FIG. 4 is a map of plasmid pLAC33. The unique restriction sites and the base pair at which they cut are indicated. Other sites of interest are also shown, including Tet (98-1288), ori (1746-2333), Amp (2504-3364), and lacPO (3619-3731).

Construction and features of pLAC11, pLAC22, and pLAC33. Plasmid maps that indicate the unique restriction sites, drug resistances, origin of replication, and other relevant regions that are contained in pLAC11, pLAC22, and pLAC33 are shown in FIGS. 2, 3 and 4, respectively. pLAC11 was designed to be the most tightly regulable of these vectors. It utilizes the ColE1 origin of replication from pBR322 and LacI repressor is provided in trans from either an episome or another compatible plasmid. pLAC22 is very similar to pLAC11, however, it also contains lacI$^q$, thus a source of LacI does not have to be provided in trans. pLAC33 is a derivative of pLAC11 which utilizes the mutated ColE1 origin of replication from pUC8 (S. Lin-Chao et al., Mol. Micro. 6:3385–3393 (1992))and thus pLAC33's copy number is significantly higher than pLAC11 and is comparable to that of other pUC vectors. Because the cloning regions of these three vectors are identical, cloned genes can be trivially shuffled between and among them depending on the expression demands of the experiment in question.

To clone into pLAC11, pLAC22, or pLAC33, PCR amplification is performed with primers that are designed to introduce unique restriction sites just upstream and downstream of the gene of interest. Usually a Bgl II site is introduced immediately in front of the ATG start codon and an EcoR I site is introduced immediately following the stop codon. An additional 6 bases is added to both ends of the oligonucleotide in order to ensure that complete digestion of the amplified PCR product will occur. After amplification the double-stranded (ds) DNA is restricted with Bgl II and EcoR I, and cloned into the vector which has also been restricted with the same two enzymes. If the gene of interest contains a BlgII site, then BamH I or Bcl I can be used instead since they generate overhangs which are compatible with Bgl II. If the gene of interest contains an EcoR I site, then a site downstream of EcoR I in the vector (such as Hind III) can be substituted.

Comparison of pLAC11, pLAC22, and pLAC33, to other expression vectors. In order to demonstrate how regulable the pLAC11, pLAC22, and pLAC33 expression vectors were, the wild-type lacZ gene was cloned into pLAC11, pLAC22, pLAC33, pKK223-3, pKK233-2, pTrc99A, and pET-21(+). Constructs which required an extraneous source of LacI for their repression were transformed into ALS225, while constructs which contained a source of LacI on the vector were transformed into ALS224. pET-21(+) constructs were transformed into BL21 because they require T7 RNA polymerase for their expression. Four clones were chosen for each of these seven constructs and β-galactosidase assays were performed under repressed and induced conditions. Rich Amp overnights were diluted 1 to 200 in either Rich Amp Glucose or Rich Amp IPTG media and grown until they reached mid-log ($OD_{550}$=0.5). In the case of PET-21(+) the pLysE and pLysS plasmids, which make T7 lysozyme and thus lower the amount of available T7 polymerase, were also transformed into each of the constructs. Table 6 shows the results of these studies and also lists the induction ratio that was determined for each of the expression vectors. As the data clearly indicate, pLAC11 is the most regulable of these expression vectors and its induction ratio is close to that which can be achieved with the wild-type lac operon. The vector which yielded the lowest level of expression under repressed conditions was pLAC11, while the vector which yielded the highest level of expression under induced conditions was pLAC33.

TABLE 6

β-galactosidase levels obtained in diferent expression vectors grown under either repressed or induced conditions

| | | # of Miller Units Observed | | |
|---|---|---|---|---|
| Vector | Source | Repressed Conditions | Induced Conditions | Fold Induction |
| pLAC11 | F' | 19 | 11209 | 590X |
| pLAC22 | Plasmid | 152 | 13315 | 88X |
| pLAC33 | F' | 322 | 23443 | 73X |
| pKK223-3 | F' | 92 | 11037 | 120X |
| pKK233-2 | F' | 85 | 10371 | 122X |
| pTrc99A | Plasmid | 261 | 21381 | 82X |
| pET-21(−) | Plasmid | 2929 | 16803 | 6X |
| pET-21(−)/pLysE | Plasmid | 4085 | 19558 | 5X |
| pET-21(−)/pLysS | Plasmid | 1598 | 20268 | 13X |

The average values obtained for the four clones that were tested from each vector are listed in the table. Standard deviation is not shown but was less than 5% in each case. Induction ratios are expressed as the ratio of enzymatic activity observed at fully induced conditions versus fully repressed conditions. The plasmid pLysE yielded unexpected results; it was expected to cause lower amounts of lacZ to be expressed from pET-21(+) under repressed conditions and, instead, higher amounts were observed. As a result, both pLysE and pLysS were restriction mapped to make sure that they were correct.

Figure 5:
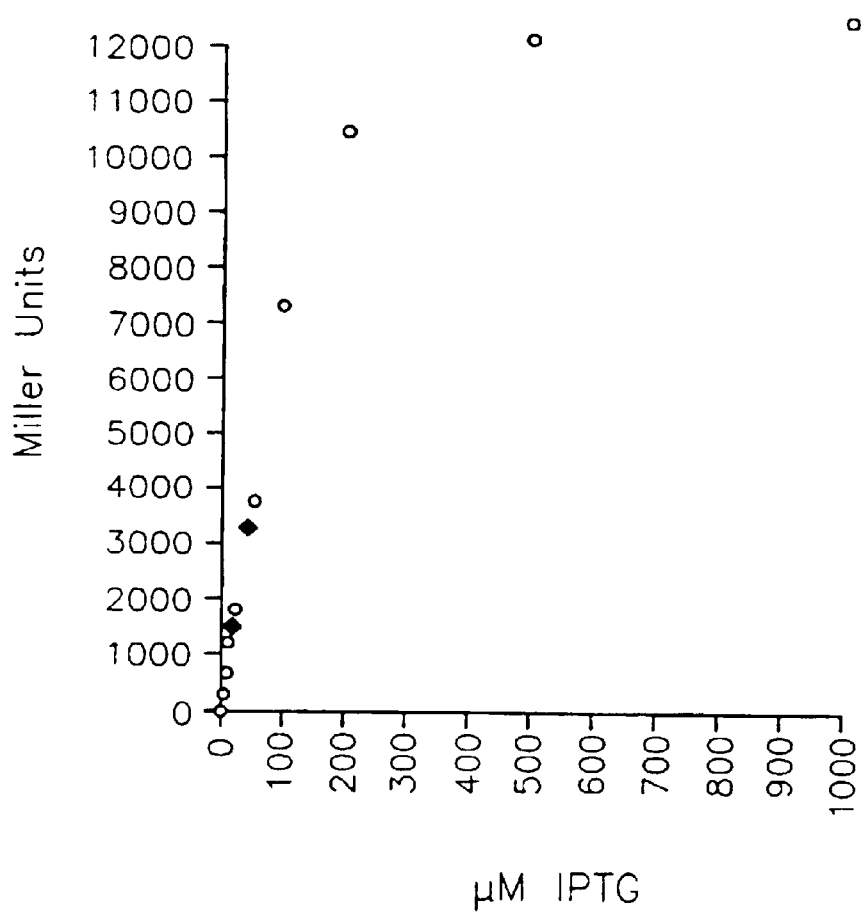
FIG. 5 shows the response of the pLAC11-lacZ construct (open circles) to varying amounts of isopropyl β-D-thiogalactoside (IPTG). A filled square indicates the β-galactosidase activity that was obtained when MG1655 or CSH27 cells were grown in rich media induced with 1 mM IPTG, while a filled diamond indicates the β-galactosidase activity that was obtained when MG1655 or CSH27 cells were grown in M9 minimal lactose media.

Demonstrating that pLAC11 constructs can be tightly regulated. pLAC11 was designed to provide researchers with an expression vector that could be utilized to conduct physiological experiments in which a cloned gene is studied under completely repressed conditions where it is off or partially induced conditions where it is expressed at physiologically relevant levels. FIG. 5 demonstrates how a pLAC11-lacZ construct can be utilized to mimic chromosomally expressed lacZ that occurs under various physiological conditions by varying the amount of IPTG inducer that is added. ALS226 cells containing pLAC11-lacZ were grown to mid-log in rich media that contained varying amounts of IPTG and then β-galactosidase activity was assayed. Also indicated in the graph are the average β-galactosidase activities obtained for strains with a single chromosomal copy of the wild-type lacZ gene that were grown under different conditions.

To demonstrate just how regulable pLAC11 is, the recA gene was cloned into the pLAC11 vector and transformed into cells which contained a null recA allele in the chromosome. As the results in Table 7 clearly shows, recombination cannot occur in a host strain which contains a nonfunctional RecA protein and thus P1 lysates which provide a Tn10dKan transposon can not be used to transduce the strain to $Kan^R$ a high frequency. $recA^-$ cells which also contain the pLAC11-recA construct can be transduced to $Kan^R$ at a high frequency when grown under induced conditions but cannot be transduced to $Kan^R$ when grown under repressed conditions.

TABLE 7

The recombination (–) phenotype of a recA null mutant strain can be preserved with a pLAC11-recA (wild-type) construct under repressed conditions

| Strain | Repressed Conditions Number of $Kan^R$ transductants | Induced Conditions Number of $Kan^R$ transductants |
|---|---|---|
| ALS225 ($recA^+$) | 178,000 | 152,000 |
| ALS514 ($recA^-$) | 5 | 4 |
| ALS515 ($recA^-$pCyt-3-recA) | 4 | 174,000 |

The data presented in Table 7 are the number of $Kan^R$ transductants that were obtained from the different MC1061 derivative strains when they were transduced with a P1 lysate prepared from strain ALS598 which harbored a Tn10dKan transposon insertion. Overnights were prepared from each of these strains using either rich medium to which glucose was added at a final concentration of 0.2% (repressed conditions) or rich medium to which IPTG was added at a final concentration of 1 mM (induced conditions). The overnights were then diluted 1 to 10 into the same medium which contained $CaCl_2$ added to a final concentration of 10 mM and aerated for two hours to make them competent for transduction with P1 phage. Cells were then spectrophotometrically normalized and 0.1 ml aliquots of cells at an $OD_{50}$ of 5 were transduced with 0.1 ml of concentrated P1 lysate as well as 0.1 ml of P1 lysates that had been diluted to $10^{-1}$, $10^{-2}$, or $10^{-3}$. 0.2 ml of 0.1 M Sodium Citrate was added to the cell/phage mixtures and 0.2 ml of the final mixtures were plated onto Rich Kanamycin plates and incubated overnight at 37° C. The total number of $Kan^R$ colonies were then counted. ALS225 $recA^+$ data points were taken from the transductions which used the $10^{-3}$ diluted phage, while ALS514 $recA^-$ data points were taken from the transductions which used the concentrated phage. The data points for ALS515 $recA^-$ pCyt-3-recA grown under repressed conditions were taken from the transductions which used the concentrated phage, while the data points for ALS515 $recA^-$ pCyt-3-recA grown under induced conditions were taken from the transductions which used the $10^{-3}$ diluted phage.

Testing various sources of LacI for trans repression of pLAC11. Because pLAC11 was designed to be used with an extraneous source of LacI repressor, different episomal or plasmid sources of LacI which are routinely employed by researchers were tested. Since one of the LacI sources also contained the lacZ gene, a reporter construct other than pLAC11-lacZ was required and thus a pLAC11-xylE construct was engineered. Table 8 shows the results of this study.

All of the LacI sources that were tested proved to be adequate to repress expression from pLAC11, however, some were better than others. The basal level of expression that was observed with F's which provided $lacI^{q_1}$ or with the plasmid pMS421 which provided $lacI^q$ at approximately six copies per cell was lower than the basal level of expression that was observed with F's which provided $lacI^q$ all three times that the assay was run. Unfortunately, however, the xylE gene could not be induced as high when $lacI^{q_1}$ on a F' or $lacI^q$ on a plasmid was used as the source of Lac repressor.

TABLE 8

Catechol 2,3-dioxygenase levels obtained for a pLAC11-xylE construct when Lac repressor is provided by various sources

| | | Catechol 2,3-dioxygenase activity in milliunits/mg | |
|---|---|---|---|
| Strain | Source of LacI | Repressed Conditions | Repressed Conditions |
| ALS224 | None | 32.7 | 432.8 |
| ALS535 | F'$lacI^q$ Δ(lacZ)M15 $proA^+B^+$ Tn10 | .3 | 204.4 |
| ALS527 | F'$lacI^q$ Δ(lacZ)M15 $proA^+B^+$ | .3 | 243.3 |
| ALS227 | pMS421 $lacI^q$ | .2 | 90.9 |
| ALS225 | F'$lacI^{q_1}$ $Z^+$ $Y^+$ $A^+$ | .2 | 107.4 |
| ALS226 | F'$lacI^{q_1}$ Z::Tn5 $Y^+$ $A^+$ | .2 | 85.1 |

The wild-type xylE gene was cloned into the pLAC11 vector and the resulting pLAC11-xylE construct was then transformed into each of the MC1061 derivative strains listed in the table. Rich overnights were diluted 1 to 200 in either Rich Glucose or Rich IPTG media and grown until they reached mid-log ($OD_{550}$=0.5). Cell extracts were then prepared and catechol 2,3-dioxygenase assays were performed as described by Zukowski, et. al. (Proc. Natl. Acad. Sci. U.S.A. 80:1101–1105 (1983)). The average values obtained in three different experiments are listed in the table. Standard deviation is not shown but was less than 10% in each case.

DISCUSSION

Most of the routinely employed expression vectors rely on lac control in order to overproduce a gene of choice. The lac promoter/operator functions as it does due to the interplay of three main components. First, the wild-type lac –10 region (TATGTT) is very weak. c-AMP activated CAP protein is able to bind to the CAP site just upstream of the –35 region which stimulates binding of RNA polymerase to the weak –10 site. Repression of the lac promoter is observed when glucose is the main carbon source because very little c-AMP is present which results in low amounts of available c-AMP activated CAP protein. When poor carbon sources such as lactose or glycerol are used, c-AMP levels rise and large amounts of c-AMP activated CAP protein become available. Thus induction of the lac promoter can occur. Second, Lac repressor binds to the lac operator. Lac repressor can be overcome by allolactose which is a natural byproduct of lactose utilization in the cell, or by the gratuitous inducer, IPTG. Third, the lac operator can form stable loop structures which prevents the initiation of transcription due to the interaction of the Lac repressor with the lac operator (O1) and one of two auxiliary operators, O2 which is located downstream in the coding region of the lacZ gene, or O3 which is located just upstream of the CAP binding site.

While binding of Lac repressor to the lac operator is the major effector of lac regulation, the other two components are not dispensable. However, most of the routinely used lac regulable vectors either contain mutations or deletions which alter the affect of the other two components. The pKK223-3 (J. Brosius et al., Proc. Natl. Acad. Sci. USA. 81:6929–6933 (1984)), pKK233-2 (E. Amann et al., Gene. 40:183–190 (1985)), pTrc99A (E. Amann et al., Gene. 69:301–315 (1988)), and pET family of vectors (F. Studier, Method Enzymol. 185:60–89 (1990)) contain only the lac operator (O1) and lack both the CAP binding site as well as the O3 auxiliary operator. pKK223-3, pKK233-2, and pTrc99 use a trp-lac hybrid promoter that contains the trp −35 region and the lacUV5-10 region which contains a strong TATAAT site instead of the weak TATGTT site. The pET family of vectors use the strong T7 promoter. Given this information, perhaps it is not so surprising researchers have found it is not possible to tightly shut off genes that are cloned into these vectors.

The purpose of the studies described in Example I was to design a vector which would allow researchers to better regulate their cloned genes in order to conduct physiological experiments. The expression vectors described herein were designed utilizing the wild-type lac promoter/operator in order to accomplish this purpose and include all of the lac control region, without modification, that is contained between the start of the O3 auxiliary operator through the end of the O1 operator. As with all lac based vectors, the pLAC11, pLAC22, and pLAC33 expression vectors can be turned on or off by the presence or absence of the gratuitous inducer IPTG.

Because the new vector, pLAC11, relies on the wild-type lac control region from the auxiliary lac O3 operator through the lac O1 operator, it can be more tightly regulated than the other available expression vectors. In direct comparison studies with pKK223-3, pKK233-2, pTrc99A, and pET-21 (+), the lowest level of expression under repressed conditions was achievable with the pLAC11 expression vector. Under fully induced conditions, pLAC11 expressed lacZ protein that was comparable to the levels achievable with the other expression vectors. Induction ratios of 1000× have been observed with the wild-type lac operon. Of all the expression vectors that were tested, only pLAC11 yielded induction ratios which were comparable to what has been observed with the wild-type lac operon. It should be noted that the regulation achievable by pLAC11 may be even better than the data in Table 6 indicates. Because lacZ was used in this test, the auxiliary lac $O_2$ operator which resides in the coding region of the lacZ gene was provided to the pKK223-3, pKK233-2, pTrc99A, and pET-21(+) vectors which do not normally contain either the O2 or O3 auxiliary operators. Thus the repressed states that were observed in the study in Table 6 are probably lower than one would normally observe with the pKK223-3, pKK233-2, pTrc99A, and pET-21(+) vectors.

To meet the expression needs required under different experimental circumstances, two additional expression vectors which are derivatives of pLAC11 were designed. pLAC22 provides $lacI^q$ on the vector and thus unlike pLAC11 does not require an extraneous source of LacI for its repression. pLAC33 contains the mutated ColE1 replicon from pUC8 and thus allows proteins to be expressed at much higher levels due to the increase in the copy number of the vector. Of all the expressions that were evaluated in direct comparison studies, the highest level of protein expression under fully induced conditions was achieved using the pLAC33 vector. Because the cloning regions are identical in pLAC11, pLAC22, and pLAC33, genes that are cloned into one of these vectors can be trivially subcloned into either of the other two vectors depending on experimental circumstances. For physiological studies, pLAC11 is the best suited of the three vectors. If, however, the bacterial strain of choice can not be modified to introduce elevated levels of Lac repressor protein which can be achieved by F's or compatible plasmids that provide $lacI^{q1}$ or $lacI^{q1}$, the pLAC22 vector can be utilized. If maximal overexpression of a gene product is the goal, then the pLAC33 vector can be utilized.

Numerous experiments call for expression of a cloned gene product at physiological levels; i.e., at expression levels that are equivalent to the expression levels observed for the chromosomal copy of the gene. While this is not easily achievable with any of the commonly utilized expression vectors, these kinds of experiments can be done with the pLAC11 expression vector. By varying the IPTG concentrations, expression from the pLAC11 vector can be adjusted to match the expression levels that occur under different physiological conditions for the chromosomal copy of the gene. In fact, strains which contain both a chromosomal null mutation of the gene in question and a pLAC11 construct of the gene preserve the physiological phenotype of the null mutation under repressed conditions.

Because the use of Lac repressor is an essential component of any expression vector that utilizes the lac operon for its regulation, the ability of different source of LacI to repress the pLAC11 vector was also investigated. Researchers have historically utilized either $lacI^q$ constructs which make 10 fold more Lac repressor than wild-type lacI or $lacI^{q1}$ constructs which make 100 fold more Lac repressor than wild-type lacI (B. Müller-Hill, Prog. Biophys. Mol. Biol. 30:227–252 (1975)). The greatest level of repression of pLAC11 constructs could be achieved using F's which provided approximately one copy of the $lacI^{q1}$ gene or a multicopy compatible plasmid which provided approximately six copies of the $lacI^q$ gene. However, the induction that was achievable using these lacI sources was significantly lower than what could be achieved when F's which provided approximately one copy of the $lacI^q$ gene were used to repress the pLAC11 construct. Thus if physiological studies are the goal of an investigation, then F's which provide approximately one copy of the $lacI^{q1}$ gene or a multicopy compatible plasmid which provides approximately six copies of the $lacI^q$ gene can be used to regulate the pLAC11 vector. However, if maximal expression is desired, then F's which provide approximately one copy of the $lacI^q$ gene can be utilized. Alternatively, if a bacterial strain can tolerate prolonged overexpression of an expressed gene, and overexpression of a gene product is the desired goal, then maximal expression under induced conditions is obtained when a bacteria strain lacks any source of Lac repressor.

Example II

An in Vivo Approach for Generating Novel Bioactive Peptides that Inhibit the Growth of *E. coli*

A randomized oligonucleotide library containing sequences capable of encoding peptides containing up to 20 amino acids was cloned into pLAC11 (Example I) which allowed the peptides to either be tightly turned off or overproduced in the cytoplasm of E. coli. The randomized library was prepared using a [NNN] codon design instead of either the [NN(G,T)] or [NN(G,C)] codon design used by most fusion-phage technology researchers. [NN(G,T)] or [NN(G,C)] codons have been widely used instead of [NNN] codons to eliminate two out of the three stop codons, thus increasing the amount of full-length peptides that can be synthesized without a stop codon (J. Scott et al., Science 249:386–390 (1990); J. Delvin et al., Science 249:404–406 (1990); S. Cwirla et al., Proc. Nat'l. Acad. Sci. U.S.A. 87:6378–6382 (1990)). However, the [NN(G,T)] and [NN(G,C)] oligonucleotide codon schemes eliminate half of the otherwise available codons and, as a direct result, biases the distribution of amino acids that are generated. Moreover, the [NN(G,T)] and [NN(G,C)] codon schemes drastically affect the preferential codon usage of highly expressed genes and removes a number of the codons which are utilized by the abundant tRNAs that are present in E. coli (H. Grosjean et al., Gene. 18: 199–209 (1982); T. Ikemura, J. Mol. Biol. 151:389–409 (1981)).

Of the 20,000 peptides screened in this Example, 21 inhibitors of cell growth were found which could prevent the growth of E. coli on minimal media. The top twenty inhibitor peptides were evaluated for strength of inhibition, and the putative amino acid sequences of the top 10 "anchorless" inhibitor peptides were examined for commonly shared features or motifs.

MATERIALS AND METHODS

Media. Rich LB and minimal M9 media used in this study was prepared as in Example I. Ampicillin was used in rich media at a final concentration of 100 ug/ml and in minimal media at a final concentration of 50 ug/ml. WPTG was added to media at a final concentration of 1 mM.

Chemicals and Reagents. Extension reactions were carried out using Klenow from New England Biolabs while ligation reactions were performed using T4 DNA Ligase from Life Sciences. IPTG was obtained from Diagnostic Chemicals Limited.

Bacterial Strains and Plasmids. ALS225, which is MC1061/F'lacI$^{q1}$Z+Y+A+ (see Example I), was the E. coli bacterial strain used in this Example. The genotype for MC1061 is araD139 Δ(araABOIC-leu)7679 Δ(lac)X74 galU galK rpsL hsr– hsm+ (M. Casadaban et al., J. Mol. Biol. 138:179–207 (1980)). pLAC11, a highly regulable expression vector, is described in Example I.

Generation of the Randomized Peptide Library. The 93 base oligonucleotide 5'TAC TAT AGA TCT ATG (NNN)$_{20}$ TAA TAA GAA TTC TCG ACA 3' (SEQ ID NO: 23), where N denotes an equimolar mixture of the nucleotides A, C, G, or T, was synthesized with the trityl group and subsequently purified with an OPC cartridge using standard procedures. The complementary strand of the 93 base oligonucleotide was generated by an extension/fill-in reaction with Klenow using an equimolar amount of the 18 base oligonucleotide primer 5' TGT CGA GAA TTC TTA TTA 3' (SEQ ID NO: 24). After extension, the resulting ds-DNA was purified using a Promega DNA clean-up kit and restricted with EcoR I and Bgl II (Promega, Madison, Wisc.). The digested DNA was again purified using a Promega DNA clean-up kit and ligated to pLAC11 vector which had been digested with the same two restriction enzymes. The resulting library was transformed into electrocompetent ALS225 E. coli cells under repressed conditions (LB, ampicillin, plus glucose added to 0.2%).

Screening of Transformants to Identify Inhibitor Clones. Transformants were screened to identify any that could not grow on minimal media when the peptides were overproduced. Using this scheme, any transformant bacterial colony that overproduces a peptide that inhibits the production or function of a protein necessary for growth of that transformant on minimal media will be identified. Screening on minimal media, which imposes more stringent growth demands on the cell, will facilitate the isolation of potential inhibitors from the library. It is well known that growth in minimal media puts more demands on a bacterial cell than growth in rich media as evidenced by the drastically reduced growth rate; thus a peptide that adversely affects cell growth is more likely to be detected on minimal media. Screening was carried out using a grid-patching technique. Fifty clones at a time were patched onto both a rich repressing plate (LB Amp glucose) and a minimal inducing plate (M9 glycerol Amp IPTG) using an ordered grid. Patches that do not grow are sought because presumably these represent bacteria that are being inhibited by the expressed bioactive peptide. To verify that all of the inhibitors were legitimate, plasmid DNA was made from each inhibitory clone (QIA Prep Spin Miniprep kit; Qiagen Cat. No. 27104) and transformed into a fresh background (ALS225 cells), then checked to confirm that they were still inhibitory on plates and that their inhibition was dependent on the presence of the inducer, IPTG.

Growth Rate Analysis in Liquid Media. Inhibition strength of the peptides was assessed by subjecting the inhibitory clones to a growth rate analysis in liquid media. To determine the growth rate inhibition, starting cultures of both the peptides to be tested and a control strain which contains pLAC11 were diluted from a saturated overnight culture to an initial $OD_{550}$ of ~0.01. All cultures were then induced with 1 mM IPTG and $OD_{550}$ readings were taken until the control culture reached an $OD_{550}$ of ~0.5. The hypothetical data in Table 9 shows that when the control strain reaches an $OD_{550}$ of about 0.64 (at about 15 hours), a strain which contains a peptide that inhibits the growth rate at 50% will only have reached an $OD_{550}$ of only about 0.08. Thus, the growth of a 50% inhibited culture at 15 hours (i.e., the $OD_{550}$ at 15 hours, which is proportional to the number of cells in a given volume of culture) is only about 12.5% (that is, 0.08/0.64×100) of that of a control strain after the same amount of time, and the inhibitor peptide would thus have effectively inhibited the growth of the culture (as measured by the $OD_{550}$ at the endpoint) by 87.5% (=100%–12.5%).

TABLE 9

Hypotheical data from a peptide that inhibits growth rate at 30%, 50% and 70%

| Time in hours | OD550 readings on a control culture which contains pLAC11 | OD550 readings on a culture which contains a peptide that inhibits the growth rate at . . . | | |
|---|---|---|---|---|
| | | 25% | 50% | 75% |
| 0 | .010 | .010 | .010 | .010 |
| 2.5 | .020 | .017 | .015 | .012 |
| 5 | .040 | .028 | .020 | .014 |
| 7.5 | .080 | .047 | .030 | .017 |
| 10 | .160 | .079 | .040 | .020 |
| 12.5 | .320 | .133 | .060 | .024 |
| 5 | .640 | .226 | .080 | .028 |

Figure 6:
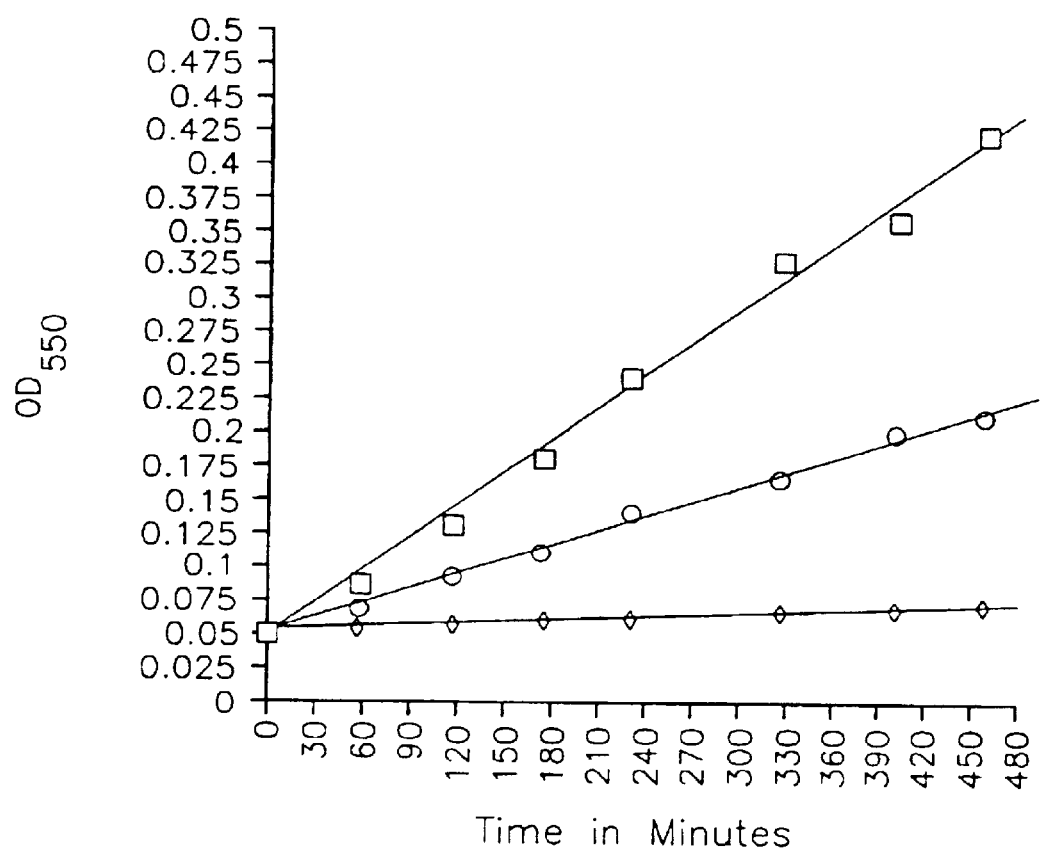
FIG. 6 shows growth curves depicting the inhibitory effects of a two day inhibitor (pPep12) versus a one day inhibitor (pPep1). Data points for the control, pLAC11, for pPep1, and for pPep12, are indicated by squares, circles, and triangles, respectively.

An example is shown in FIG. 6, wherein ALS225 cells containing the pLAC11 vector (control), and either the one day inhibitor pPep1 or the two day inhibitor pPep12 (see below), were grown in minimal M9 glycerol media with IPTG added to 1 mM. $OD_{550}$ readings were then taken hourly until the cultures had passed log phase. Growth rates were determined by measuring the spectrophotometric change in $OD_{550}$ per unit time within the log phase of growth. The inhibition of the growth rate was then calculated for the inhibitors using pLAC11 as a control.

Sequencing the Coding Regions of the Inhibitor Peptide Clones. The forward primer 5' TCA TTA ATG CAG CTG GCA CG 3' (SEQ ID NO: 25) and the reverse primer 5' TTC ATA CAC GGT GCC TGA CT 3' (SEQ ID NO: 26) were used to sequence both strands of the top ten "anchorless" inhibitor peptide clones identified by the grid-patching technique. If an error-free consensus sequence could not be deduced from these two sequencing runs, both strands of the inhibitor peptide clones in question were resequenced using the forward primer 5' TAG CTC ACT CAT TAG GCA CC 3' (SEQ ID NO: 27) and the reverse primer 5' GAT GAC GAT GAG CGC ATT GT 3' (SEQ ID NO: 28). The second set of primers were designed to anneal downstream of the first set of primers in the pLAC11 vector.

Generating Antisense Derivatives of the Top Five "Anchorless" Inhibitor Clones. Oligonucleotides were synthesized which duplicated the DNA insert contained between the Bgl II and EcoR I restriction sites for the top five "anchorless" inhibitor peptides as shown in Table 12 with one major nucleotide change. The "T" of the ATG start codon was changed to a "C" which resulted in an ACG which can not be used as a start codon. The oligonucleotides were extended using the same 18 base oligonucleotide primer that was used to build the original peptide library. The resulting ds-DNA was then restricted, and cloned into pLAC11 exactly as described in the preceding section "Generating the randomized peptide library." The antisense oligonucleotides that were used are as follows:

pPep1(antisense): 5' TAC TAT AGA TCT ACG GTC ACT GAA TTT TGT GGC TTG TTG GAC CAA CTG CCT TAG TAA TAG TGG AAG GCT GAA ATT AAT AAG AAT TCT CGA CA 3' (SEQ ID NO: 29);

pPep5(antisense): 5' TAC TAT AGA TCT ACG TGG CGG GAC TCA TGG ATT AAG GGT AGG GAC GTG GGG TTT ATG GGT TAA AAT AGT TTG ATA ATA AGA ATT CTC GAC A 3' (SEQ ID NO: 30)

pPep12(antisense): 5' TAC TAT AGA TCT ACG AAC GGC CGA ACC AAA CGA ATC CGG GAC CCA CCA GCC GCC TAA ACA GCT ACC AGC TGT GGT AAT AAG AAT TCT CGA CA 3' (SEQ ID NO: 31)

pPep13(antisense): 5' TAC TAT AGA TCT ACG GAC CGT GAA GTG ATG TGT GCG GCA AAA CAG GAA TGG AAG GAA CGA ACG CCA TAG GCC GCG TAA TAA GAA TTC TCG ACA 3' (SEQ ID NO: 32)

pPep19(antisense): 5' TAC TAT AGA TCT ACG AGG GGC GCC AAC TAA GGG GGG GGG AAG GTA TTT GTC CCG TGC ATA ATC TCG GGT GTT GTC TAA TAA GAA TTC TCG ACA 3' (SEQ ID NO: 33)

RESULTS

Identifying and Characterizing Inhibitor Peptides from the Library. Approximately 20,000 potential candidates were screened as described hereinabove, and 21 IPTG-dependent growth inhibitors were isolated. All the inhibitors so identified were able to prevent the growth of the E. coli bacteria at 24 hours, and three of the 21 inhibitors were able to prevent the growth of the E. coli bacteria at 48 hours, using the grid patching technique. These three inhibitors were classified as "two day" inhibitors; the other 18 were classified as "one-day" inhibitors.

Results from the growth rate analysis for candidate peptide inhibitors are shown in Table 10. The % inhibition of the growth rate was calculated by comparing the growth rates of cells that contained induced peptides with the growth rate of cells that contained the induced pLAC11 vector. Averaged values of three independent determinations are shown.

TABLE 10

Ability of the Inhibitor Peptides to Inhibit Cell Growth

| Inhibitor | Type | % Inhibition | Inhibitor | Type | % Inhibition |
|---|---|---|---|---|---|
| pLAC11 (control) | — | 0 | Ppep11 | 1 Day | 22 |
| pPep1 | 1 Day | 25 | Ppep12 | 2 Day | 82 |
| pPep2 | 1 Day | 23 | Ppep13 | 1 Day | 28 |
| pPep3 | 2 Day | 80 | Ppep14 | 2 Day | 71 |
| pPep4 | 1 Day | 21 | Ppep15 | 1 Day | 23 |
| pPep5 | 1 Day | 24 | Ppep16 | 1 Day | 24 |
| pPep6 | 1 Day | 27 | Ppep17 | 1 Day | 28 |
| pPep7 | 1 Day | 26 | PPep18 | 1 Day | 24 |
| pPep8 | 1 Day | 29 | pPep19 | 1 Day | 29 |
| pPep9 | 1 Day | 22 | pPep20 | 1 Day | 19 |
| pPep10 | 1 Day | 24 | pPep21 | 1 Day | 23 |

Of the 21 peptides that were tested, the one-day inhibitor peptides inhibited the bacterial growth rate at a level of approximately 25%, while the two-day inhibitor peptides inhibited the bacterial growth rate at levels greater than 75%. As can be seen from the hypothetical data in Table 9, a one-day inhibitor which inhibited the growth rate at 25% would have only reached an $OD_{550}$ of 0.226 when the control strain reached an $OD_{550}$ of 0.64. At that point in time, the growth of the culture that is inhibited by a one-day inhibitor (as measured by the end-point $OD_{550}$) only be only 35.3% of that of a control strain at that point; thus the inhibitor peptide would have effectively inhibited the growth of the culture by 64.7%. A two-day inhibitor which inhibited the growth rate at 75% would have only reached an $OD_{550}$ of 0.028 when the control strain reached an $OD_{550}$ of 0.64. Thus the growth of the culture that is being inhibited by a two-day inhibitor will only be 4.4% of that of the control strain at this point, and the inhibitor peptide would have effectively inhibited the growth of the culture by 95.6%. These calculations are consistent with the observation that two-day inhibitors prevent the growth of bacteria on plates for a full 48 hours while the one-day inhibitors only prevent the growth of bacteria on plates for 24 hours.

All 21 candidates were examined using restriction analysis to determine whether they contained 66 bp inserts as expected. While most of them did, the two-day inhibitors pPep3 and pPep14 were found to contain a huge deletion. Sequence analysis of these clones revealed that the deletion had caused the carboxy-terminal end of the inhibitor peptides to become fused to the amino-terminal end of the short 63 amino acid Rop protein. The rop gene, which is part of the ColE1 replicon, is located downstream from where the oligonucleotide library is inserted into the pLAC11 vector. Sequence Analysis of the Top 10 "Anchorless" Inhibitor Peptides. The DNA fragments comprising the sequences encoding the top 10 "anchorless" inhibitor peptides (i.e., excluding the two Rop fusion peptides) were sequenced, and their coding regions are shown in Table 11. Stop codons are represented by stars, and the landmark Bgl II and EcoR I restriction sites for the insert region are underlined. Since the ends of the oligonucleotide from which these inhibitors were constructed contained these restriction sites, the oligonucleotide was not gel isolated when the libraries were prepared in order to maximize the oligonucleotide yields. Because of this, several of the inhibitory clones were found to contain one (n−1) or two (n−2) base deletions in the randomized portion of the oligonucleotide.

TABLE 11

Sequence analysis of the insert region from the top 10
inhibitory clones and the peptides that they are predicted to
encode

```
pPep1 - 13 aa
CAG GAA AGA TCT ATG GTC ACT GAA TTT TGT GGC TTG TTG GAC CAA CTG CCT TAG TAA TAG TGG AAG GCT
            M   V   T   E   F   C   G   L   L   D   Q   L   P   *   *   *   (SEQ ID NO: 34)
GAA ATT AAT AAG AAT TC (SEQ ID NO: 35)

pPep5 - 16 aa
CAG GAA AGA TCT ATG TGG CGG GAC TCA TGG ATT AAG GGT AGG GAC GTG GGG TTT ATG GGT TAA AAT AGT
            M   W   R   D   S   W   I   K   G   R   D   V   G   F   M   G   *   (SEQ ID NO: 36)
TTG ATA ATA AGA ATT C (SEQ ID NO: 37)

pPep6 - 42 aa - last 25 aa could form a hydrophobic membrane-
spanning domain
CAG GAA AGA TCT ATG TCA GGG GGA CAT GTG ACG AGG GAG TGC AAG TCG GCG ATG TCC AAT CGT TGG ATC
            M   S   G   G   H   V   T   R   E   C   K   S   A   M   S   N   R   W   I
TAC GTA ATA AGA ATT CTC ATG TTT GAC AGC TTA TCA TCG ATA AGC TTT AAT GCG GTA GTT TAT CAC AGT
 Y   V   I   R   I   L   M   F   D   S   L   S   S   I   S   F   N   A   V   V   Y   R   S
TAA (SEQ ID NO: 38)
 *  (SEQ ID MO: 39)

pPep7 - 6 aa
CAG GAA AGA TCT ATG TAT TTG TTC ATC GGA TAA TAC TTA ATG GTC CGC TGG AGA ACT TCA GTT TAA TAA
            M   Y   L   F   I   G   *   (SEQ ID NO: 40)
GAA TTC (SEQ ID NO: 41)

pPep8 - 21 aa
CAG GAA AGA TCT ATG CTT CTA TTT GGG GGG GAC TGC GGG CAG AAA GCC GGA TAC TTT ACT GTG CTA CCG
            M   L   L   F   G   G   D   C   G   Q   K   A   G   Y   F   T   V   L   P
TCA AGG TAA TAA GAA TTC (SEQ ID NO: 42)
 S   R   *   *  (SEQ ID NO: 43)

pPep10 - 20 aa - predicted to be 45% β-sheet -amino acids 6-14
CAG GAA AGA TCT ATG ATT GGG GGA TCG TTG AGC TTC GCC TGG GCA ATA GTT TGT AAT AAG AAT TCT CAT
            M   I   G   G   S   L   S   F   A   W   A   I   V   C   N   K   N   S   H
GTT TGA (SEQ ID NO: 44)
 V   *  (SEQ ID NO: 45)

pPep12 - 14 aa
CAG GAA AGA TCT ATG AAC GGC CGA ACC AAA CGA ATC CGG GAC CCA CCA GCC GCC TAA ACA GCT ACC AGC
            M   N   G   R   T   K   R   I   R   D   P   P   A   A   *  (SEQ ID NO: 46)
TGT GGT AAT AAG AAT TC (SEQ ID NO: 47)

pPep13 -18 aa - predicted to be 72% α-helical - amino acids 3-15
CAG GAA AGA TCT ATG GAC CGT GAA GTG ATG TGT GCG GCA AAA CAG GAA TGG AAG GAA CGA ACG CCA TAG
            M   D   R   E   V   M   C   A   A   K   Q   E   W   K   E   R   T   P   *
(SEQ ID NO: 48)
GCC GCG TAA TAA GAA TTC (SEQ ID NO: 49)

pPep17 - 12 aa
CAG GAA AGA TCT ATG TAG CCC AAT GCA CTG GGA GCA CGC GTG TTA GGT CTA GAA GCC ACG TAC CCA TTT
            M   *                       M   L   G   L   E   A   T   Y   P   F
AAT CCA TAA TAA GAA TTC (SEQ ID NO: 50)
 N   P   *   *  (SEQ ID NO: 51)

pPep19 - 5 aa
CAG GAA AGA TCT ATG AGG GGC GCC AAC TAA GGG GGG GGG AAG GTA TTT GTC CCG TGC ATA ATC TCG GGT
            M   R   G   A   N   *  (SEQ TD NO: 52)
GTT GTC TAA TAA GAA TTC (SEQ ID NO: 53)
```

Eight out of the top 10 inhibitors were predicted to encode peptides that terminate before the double TAA TAA termination site, which was engineered into the oligonucleotide. Two of the inhibitors, pPep6 and pPep10, which contain deletions within the randomized portion of the oligonucleotide, are terminated beyond the EcoR I site. One of the inhibitors, pPep17, contains a termination signal just after the ATG start codon. However, just downstream from this is a Shine Dalgarno site and a GTG codon, which should function as the start codon. Interestingly, the start sites of several proteins such as Rop are identical to that proposed for the pPep17 peptide (G. Cesareni et al., Proc. Natl. Acad. Sci. USA. 79:6313–6317 (1982)). The average and median length for the 8 peptides whose termination signals occurred before or at the double TAA TAA termination site was 13 amino acids.

The characteristics of the predicted coding regions of the inhibitor peptides proved to be quite interesting. Three out of the top 10 peptides, pPep1, pPep13, and pPep17, contained a proline residue as their last (C-terminal) amino acid. Additionally, one of the peptides, pPep12, contained 2 proline residues near the C-terminus, at the n−2 and n−3 positions. Thus there appears to be a bias for the placement of proline residues at or near the end of several of the inhibitory peptides. Secondary structure analysis predicted that 3 out of the 10 peptides contained a known motif that could potentially form a very stable structure. pPep13, a peptide containing a C-terminal proline, is predicted to be 72% α-helical, pPep10 is predicted to be 45% β-sheet, and pPep6 is predicted to form a hydrophobic membrane spanning domain.

Verifying that the Inhibitory Clones do not Function as Antisense. To rule out the possibility that the bioactivity of the inhibitory clones resulted from their functioning as antisense RNA or DNA (thus hybridizing to host DNA or RNA) rather than by way of the encoded peptides, the insert regions between the Bgl II and EcoR I sites for the top five inhibitors from Table 10 were recloned into the pLAC11 vector using oligonucleotides which converted the ATG start codon to an ACG codon thus abolishing the start site. In all five cases the new constructs were no longer inhibitory (see Table 12), thus confirming that it is the encoded peptides that causes the inhibition and not the DNA or transcribed mRNA.

TABLE 12

Antisense test of the top 5 "anchorless" inhibitory peptides from

| Inhibitory peptide | % inhibition versus pLAC11 control | Antisense construct | % inhibition versus pLAC11 control |
|---|---|---|---|
| pPep1 | 26 | pPep1-anti | 0 |
| pPep5 | 23 | pPep5-anti | 0 |
| pPep12 | 80 | pPep12-anti | 0 |
| pPep13 | 28 | pPep13-anti | 0 |
| pPep19 | 29 | pPep19-anti | 0 |

Growth rates for cells containing the induced inhibitors or antisense constructs were determined and then the % inhibition was calculated by comparing these values to the growth rate of cells that contained the induced pCyt-3 vector.

DISCUSSION

Use of the tightly regulable pLAC11 expression vector made possible the identification of novel bioactive peptides. The bioactive peptides identified using the system described in this Example inhibit the growth of the host organism (*E. coli*) on minimal media. Moreover, bioactive peptides thus identified are, by reason of the selection process itself, stable in the host's cellular environment. Peptides that are unstable in the host cell, whether or not bioactive, will be degraded; those that have short half-lives are, as a result, not part of the selectable pool. The selection system thus makes it possible to identify and characterize novel, stable, degradation-resistant bioactive peptides in essentially a single experiment.

The stability of the inhibitory peptides identified in this Example may be related to the presence of certain shared structural features. For example, three out of the top 10 inhibitory "anchorless" (i.e., non-Rop fusion) peptides contained a proline residue as their last amino acid. According to the genetic code, a randomly generated oligonucleotide such as the one used in this Example has only a 6% chance of encoding a proline at a given position, yet the frequency of a C-terminal proline among the top ten inhibitory peptides is a full 30%. This 5-fold bias in favor of a C-terminal proline is quite surprising, because although the presence of proline in a polypeptide chain generally protects biologically active proteins against nonspecific enzymatic degradation, a group of enzymes exists that specifically recognize proline at or near the N- and C-termini of peptide substrates. Indeed, proline-specific peptidases have been discovered that cover practically all situations where a proline residue might occur in a potential substrate (D. F. Cunningham et al., Biochimica et Biophysics Acta 1343:160–186 (1997)). For example, although the N-terminal sequences Xaa-Pro-Yaa- and Xaa-Pro-Pro-Yaa (SEQ ID NO: 54) have been identified as being protective against nonspecific N-terminal degradation, the former sequence is cleaved by aminopeptidase P (at the Xaa-Pro bond) and dipeptidyl peptidases IV and II (at the -Pro-Yaa-bond)) (Table 5, G. Vanhoof et al., FASEB J. 9:736–44 (1995); D. F. Cunningham et al., Biochimica et Biophysics Acta 1343:160–186 (1997)); and the latter sequence, present in bradykinin, interleukin 6, factor XII and erythropoietin, is possibly cleaved by consecutive action of aminopeptidase P and dipeptidyl peptidase IV (DPPIV), or by prolyl oligopeptidase (post Pro-Pro bond) (Table 5, G. Vanhoof et al., FASEB J. 9:736–44 (1995)). Prolyl oligopeptidase is also known to cleave Pro-Xaa bonds in peptides that contain an N-terminal acyl-Yaa-Pro-Xaa sequence (D. F. Cunningham et al., Biochimica et Biophysics Acta 1343:160–186 (1997)). Other proline specific peptidases acting on the N-terminus of substrates include prolidase, proline iminopeptidase and prolinase. Prolyl carboxypeptidase and carboxypeptidase P, on the other hand, cleave C-terminal residues from peptides with proline being the preferred $P_1$ residue (D. F. Cunningham et al., Biochimica et Biophysics Acta 1343:160–186 (1997).

Also of interest with respect to the stability of the inhibitory peptides, three of the top ten (30%) contained motifs that were predicted, using standard protein structure prediction algorithms, to form stable secondary structures. One of the peptides (which also has a C-terminal proline) was predicted to be 72% α-helical. Another was predicted to be 45% β-sheet; this peptide may dimerize in order to effect the hydrogen bonding necessary to form the β-sheet. A third was predicted to possess a hydrophobic membrane spanning domain. According to these algorithms (see, e.g., P. Chou et al., Adv. Enzymol. 47:45–148 (1978); J. Garnier et al., J. Mol. Biol. 120:97–120 (1978); P. Chou, "Prediction of protein structural classes from amino acid composition." In Prediction of Protein Structure and the Principles of Protein Conformation (Fasman, G. D. ed.). Plenum Press, New York, N.Y. 549–586 (1990); P. Klein et al., Biochim. Biophys. Acta 815:468–476 (1985)), a randomly generated oligonucleotide such as the one used in our studies would have had no better than a 1 in a 1000 chance of generating the motifs that occurred in these peptides.

Finally, two of the three two-day inhibitors proved to be fusion peptides in which the carboxyl terminus of the peptides was fused to the amino terminus of the Rop protein. Rop is a small 63 amino acid protein that consists of two antiparallel α-helices connected by a sharp hairpin loop. It is a dispensable part of the ColE1 replicon which is used by plasmids such as pBr322, and it can be deleted without causing any ill-effects on the replication, partitioning, or copy numbers of plasmids that contain a ColE1 ori (X. Soberon, Gene. 9: 287–305 (1980). Rop is known to possess a highly stable structure (W. Eberle et al., Biochem. 29:7402–7407 (1990); S. Betz et al., Biochemistry 36:2450–2458 (1997)), and thus it could be serving as a stable protein anchor for these two peptides.

Table 13 lists naturally occurring bioactive peptides whose structures have been determined. Most of these peptides contain ordered structures, further highlighting the importance of structural stabilization. Research on developing novel synthetic inhibitory peptides for use as potential therapeutic agents over the last few years has shown that peptide stability is a major problem that must be solved if designer synthetic peptides are to become a mainstay in the pharmaceutical industry (J. Bai et al., Crit. Rev. Ther. Drug.

12:339–371 (1995); R. Egleton Peptides. 18:1431–1439 (1997); L. Wearley, Crit Rev Ther Drug Carrier Syst. 8: 331–394 (1991). The system described in this Example represents a major advance in the art of peptide drug development by biasing the selection process in favor of bioactive peptides that exhibit a high degree of stability in an intracellular environment.

TABLE 13

Structural motifs observed in naturally occurring bioactive peptides

| Bioactive Peptide | Size in Amino acids | Structural Motif | Reference |
|---|---|---|---|
| Dermaseptin | 34 | α-helix | 34 |
| Endorphin | 30 | α-helix | 7 |
| Glucagon | 29 | α-helix | 6 |
| Magainins[a] | 23 | α-helix | 5 |
| Mastoparan | 14 | α-helix | 11 |
| Melittin | 26 | α-helix | 44 |
| Motilin | 22 | α-helix | 25 |
| PK1 (5-24) | 20 | α-helix | 38 |
| Secretin | 27 | α-helix | 8 |
| Atrial Natriuretic Peptide | 28 | disulfide bonds | 33 |
| Calcitonin | 32 | disulfide bonds | 4 |
| Conotoxins[a] | 10–30 | disulfide bonds | 37 |
| Defensins[a] | 29–34 | disulfide bonds | 30 |
| EET1 II | 29 | disulfide bonds | 23 |
| Oxytocin | 9 | disulfide bonds | 45 |
| Somatostatin | 14 | disulfide bonds | 35 |
| Vasopressin | 9 | disulfide bonds | 20 |
| Bombesin | 14 | disordered | 12 |
| Histatin | 24 | disordered | 51 |
| Substance P | 11 | disordered | 50 |

[a]These peptides belong to multi-member families.

Example III

Directed Synthesis of Stable Synthetically Engineered Inhibitor Peptides

These experiments were directed toward increasing the number of bioactive peptides produced by the selection method described in Example II. In, the initial experiment, randomized peptides fused to the Rop protein, at either the N- or C-terminus, were evaluated. In the second experiment, nucleic acid sequences encoding peptides containing a randomized internal amino acid sequence flanked by terminal prolines were evaluated. Other experiments included engineering into the peptides an α-helical structural motif, and engineering in a cluster of opposite charges at the N- and C-termini of the peptide.

MATERIALS AND METHODS

Media. Rich LB and minimal M9 media used in this study was prepared as described by Miller (see Example I). Ampicillin was used in rich media at a final concentration of 100 ug/ml and in minimal media at a final concentration of 50 ug/ml. IPTG was added to media at a final concentration of 1 mM.

Chemicals and Reagents. Extension reactions were carried out using Klenow from New England Biolabs (Bedford, Mass.) while ligation reactions were performed using T4 DNA ligase from Life Sciences (Gaithersburg, Md.) Alkaline phosphatase (calf intestinal mucosa) from Pharmacia (Piscataway, N.J.) was used for dephosphorylation. IPTG was obtained from Diagnostic Chemicals Limited (Oxford, Conn.).

Bacterial Strains and Plasmids. ALS225, which is MC1061/ F'lacI$^{q1}$Z+Y+A+, was the E. coli bacterial strain used in this study (see Example I). The genotype for MC1061 is araD139 Δ(araABOIC-leu)7679 Δ(lac)X74 galU galK rpsL hsr-hsm+ as previously described. pLAC11 (Example I), a highly regulable expression vector, was used to make p-Rop (C) and p(N)Rop-fusion vectors as well as the other randomized peptide libraries which are described below.

Figure 7:
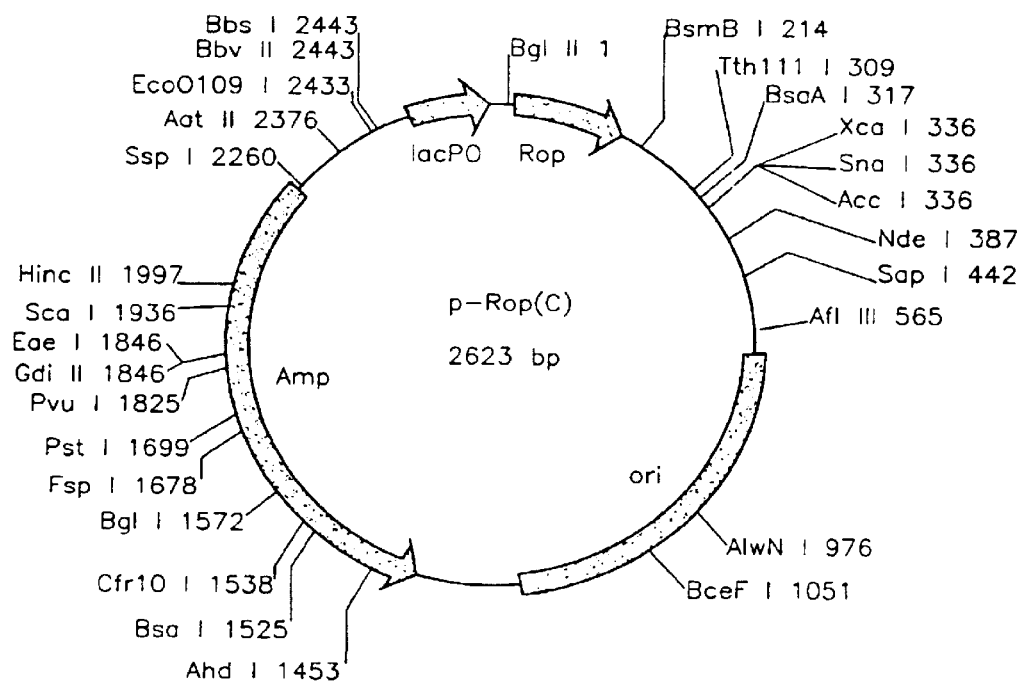
FIG. 7 is a map of the p-Rop(C) fusion vector. The unique restriction sites and the base pair at which they cut are indicated. Other sites of interest are also shown, including Rop (7-198), ori (627-1214), Amp (2245-1385), lacPO (2500-2612).

Construction of the p-Rop(C) Fusion Vector. The forward primer 5' TAC TAT AGA TCT ATG ACC AAA CAG GAA AAA ACC GCC 3' (SEQ ID NO: 55) and the reverse primer 5' TAT ACG TAT TCA GTT GCT CAC ATG TTC TTT CCT GCG 3' (SEQ ID NO: 56) were used to PCR amplify a 558 bp DNA fragment using pBR322 as a template. This fragment contained a Bgl II restriction site which was incorporated into the forward primer followed by an ATG start codon and the Rop coding region. The fragment extended beyond the Rop stop codon through the Afl III restriction site in pBR322. The amplified dsDNA was gel isolated, restricted with Bgl II and Afl III, and then ligated into the pLAC expression vector which had been digested with the same two restriction enzymes. The resulting p-Rop(C) fusion vector is 2623 bp in size (FIG. 7).

Figure 8:
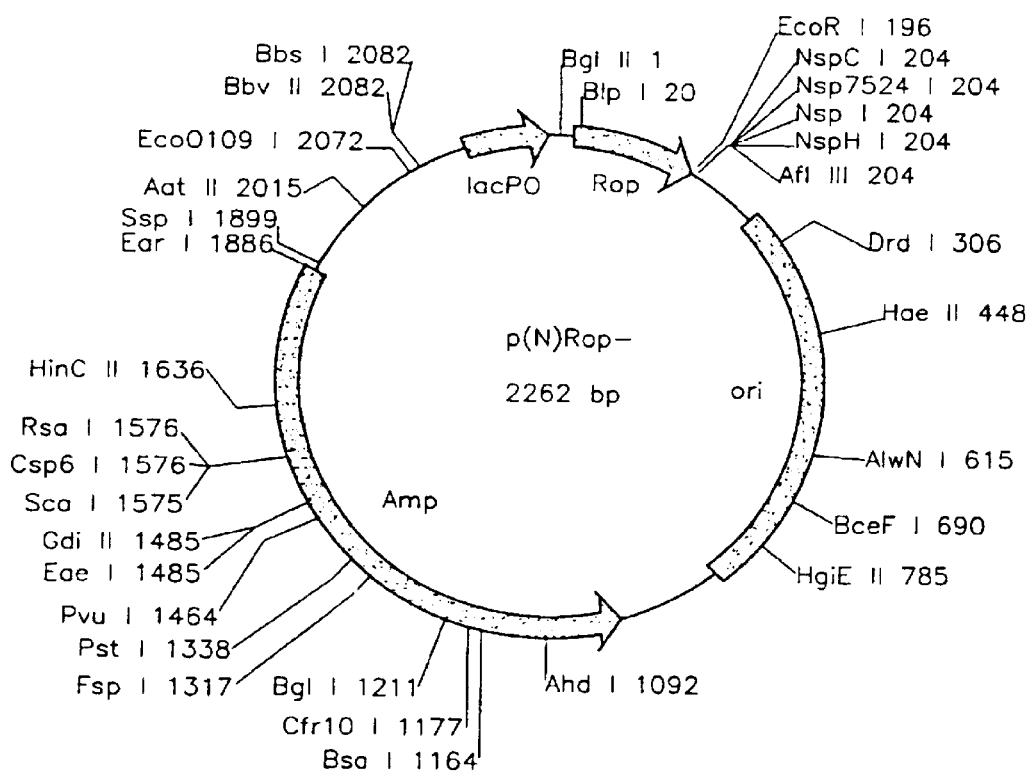
FIG. 8 is a map of the p(N)Rop-fusion vector. The unique restriction sites and the base pair at which they cut are indicated. Other sites of interest are also shown: Rop (7-204), ori (266-853), Amp (1024-1884), lacPO (2139-2251).

Construction of the p(N)Rop-Fusion Vector. The forward primer 5' AAT TCA TAC TAT AGA TCT ATG ACC AAA CAG GAA AAA ACC GC 3' (SEQ ID NO: 57) and the reverse primer 5' TAT ATA ATA CAT GTC AGA ATT CGA GGT TTT CAC CGT CAT CAC 3' (SEQ ID NO: 58) were used to PCR amplify a 201 bp DNA fragment using pBR322 as a template. This fragment contained a Bgl II restriction site which was incorporated into the forward primer followed by an ATG start codon and the Rop coding region. The reverse primer placed an EcoR I restriction site just before the Rop TGA stop codon and an Afl III restriction site immediately after the Rop TGA stop codon. The amplified dsDNA was gel isolated, restricted with Bgl II and Afl III, and then ligated into the pLAC11 expression vector which had been digested with the same two restriction enzymes. The resulting p(N)Rop-fusion vector is 2262 bp in size (FIG. 8).

Generation of Rop Fusion Randomized Peptide Libraries. Peptide libraries were constructed as described in Example II. The synthetic oligonucleotide 5' TAC TAT AGA TCT ATG (NNN)$_{20}$ CAT AGA TCT GCG TGC TGT GAT 3' (SEQ ID NO: 59) was used to construct the randomized peptide libraries for use with the p-Rop(C) fusion vector, substantially as described in Example II. The complementary strand of this oligonucleotide was generated by a fill-in reaction with Klenow using an equimolar amount of the oligonucleotide primer 5' ATC ACA GCA CGC AGA TCT ATG 3' were used (SEQ ID NO: 60). After extension, the resulting dsDNA was digested with Bgl II and ligated into the pLAC11 expression vector which had been digested with the same restriction enzyme and subsequently dephosphorylated using alkaline phosphatase. Because of the way the oligonucleotide library has been engineered, either orientation of the incoming digested double-stranded DNA fragment results in a fusion product.

To construct the randomized peptide libraries for use with the p(N)Rop-fusion vector, the randomized oligonucleotide 5' TAC TAT GAA TTC (NNN)$_{20}$ GAA TTC TGC CAC CAC TAC TAT 3' (SEQ ID NO: 61), and the primer 5' ATA GTA GTG GTG GCA GAA TTC 3' (SEQ ID NO: 62) were used. After extension, the resulting dsDNA was digested with EcoRI and ligated into the pLAC11 expression vector which had been digested with the same restriction enzyme and subsequently dephosphorylated using alkaline phosphatase. Because of the way the oligonucleotide library has been engineered, either orientation of the incoming digested double-stranded DNA fragment results in a fusion product.

Generation of a Randomized Peptide Library Containing Terminal Prolines. Randomized amino acid peptide libraries containing two proline residues at both the amino and the carboxy terminal ends of the peptides were constructed using the synthetic oligonucleotide 5' TAC TAT AGA TCT ATG CCG CCG (NNN)$_{16}$ CCG CCG TAA TAA GAA TTC GTA CAT 3' (SEQ ID NO: 63). The complementary strand of the 93 base randomized oligonucleotide was generated by filling in with Klenow using the oligonucleotide primer 5' ATG TAC GAA TTC TTA TTA CGG CGG 3' (SEQ ID NO: 64). After extension, the resulting dsDNA was digested with Bgl II and EcoR I and ligated into the pLAC11 expression vector which had been digested with the same two restriction enzymes. Because the initiating methionine of the peptides coded by this library is followed by a proline residue, the initiating methionine will be removed (F. Sherman et al, Bioessays 3:27–31 (1985)). Thus the peptide libraries encoded by this scheme are 20 amino acids in length.

Generation of a Randomized Hydrophilic α-Helical Peptide Library. Table 14 shows the genetic code highlighted to indicate certain amino acid properties.

asparagine would be expected to occur in about 17% of the positions, which is acceptable in an α-helical structure according to the secondary structure prediction rules of either Chou and Fasman (P. Chou et al., Adv. Enzymol. 47:45–148 (1978); P. Chou, "Prediction of protein structural classes from amino acid compositions," in *Prediction of protein structure and the principles of protein conformation* (G. Fasman, G. D. ed.). Plenum Press, New York, N.Y. 549–586 (1990)) or Garnier, Osguthorpe, and Robson (J. Garnier et al., J. Mol. Biol. 120:97–120 (1978)). Additionally, several well-characterized proteins have been observed to contain up to three $b_a$ breaker amino acids within a similarly sized α-helical region of the protein (T. Creighton, "Conformational properties of polypeptide chains," in *Proteins: structures and molecular properties,* W. H. Freeman and Company, N.Y., 182–186 (1993)). Since in most α-helices there are 3.6 amino acids per complete turn, the 18 amino acid length was chosen in order to generate α-helical peptides which contained 5 complete turns. Moreover, the use of hydrophilic amino acids would be expected to yield peptides which are soluble in the cellular cytosol.

TABLE 14

Genetic Code Highlighted to Indicate Amino Acid Properties

| | | | | | | | | | | | | | | |
|---|---|---|---|---|---|---|---|---|---|---|---|---|---|---|
| TTT | phe | $h_a$ | TCT | ser | | TAT | tyr | $b_a$ | | TGT | cys | | | |
| TTC | phe | $h_a$ | TCC | ser | | TAC | tyr | $b_a$ | | TGC | cys | | | |
| TTA | leu | $H_a$ | TCA | ser | | TAA | OCH | | | TGA | OPA | | | |
| TTG | leu | $H_a$ | TCG | ser | | TAG | AMB | | | TGG | trp | | | |
| CTT | leu | $H_a$ | CCT | pro | $B_a$ | CAT | *his* | $h_a$ | | CGT | *arg* | | | |
| CTC | leu | $H_a$ | CCC | pro | $B_a$ | CAC | *his* | $h_a$ | | CGC | *arg* | | | |
| CTA | leu | $H_a$ | CCA | pro | $B_a$ | CAA | *gln* | $h_a$ | | CGA | *arg* | | | |
| CTG | leu | $H_a$ | CCG | pro | $B_a$ | CAG | *gln* | $h_a$ | | CGG | *arg* | | | |
| ATT | ile | $h_a$ | ACT | thr | | AAT | *asn* | $b_a$ | | AGT | ser | | | |
| ATC | ile | $h_a$ | ACC | thr | | AAC | *asn* | $b_a$ | | AGC | ser | | | |
| ATA | ile | $h_a$ | ACA | thr | | AAA | *lys* | $h_a$ | | AGA | *arg* | | | |
| ATG | met | $H_a$ | ACG | thr | | AAG | *lys* | $h_a$ | | AGG | *arg* | | | |
| GTT | val | $h_a$ | GCT | ala | $H_a$ | GAT | *asp* | $h_a$ | | GGT | gly | $B_a$ | | |
| GTC | val | $h_a$ | GCC | ala | $H_a$ | GAC | *asp* | $h_a$ | | GGC | gly | $B_a$ | | |
| GTA | val | $h_a$ | GCA | ala | $H_a$ | GAA | *glu* | $H_a$ | | GGA | gly | $B_a$ | | |
| GTG | val | $h_a$ | GCG | ala | $H_a$ | GAG | *glu* | $H_a$ | | GGG | gly | $B_a$ | | |

Boldface amino acids are hydrophobic while italicized amino acids are hydrophilic. The propensity for various amino acids to form α-helical structures is also indicated in this table using the conventions first described by Chou and Fasman (P. Chou et al., Adv. Enzymol 47:45–148 (1978)). $H_a$ = strong α-helix former, $h_a$ = α-helix former. $B_a$ = strong α-helix breaker, $b_a$ = α-helix breaker. The assignments given in this table are the consensus agreement from several different sources. Hydrophilic versus hydrophobic assignments for the amino acids were made from data found in Wolfenden et. al. (Biochemistry 20:849–55 (1981)): Miller et. al. (J. Mol. Biol. 196:641–656 (1987)): and Roseman (J. Mol. Biol. 200:513–22 (1988)). The propensity for amino acids to form α-helical structures were obtained from consensus agreements of the Chou and Fasman (P. Chou et. al., Adv. Enzymol. 47:45–148 (1978): P. Chou, "Prediction of protein structural classes from amino acid compositions," in Prediction of protein structure and the principles of protein conformation (G. Fasman, G.D. ed.). Plenum Press, New York, N.Y. 549–586 (1990)): Garnier, Osguthorpe, and Robson (J. Mol. Biol. 120:97–120 (1978)): and O'Neill and DeGrado (Science, 250:646–651 (1990)) methods for predicting secondary structure.

By analyzing the distribution pattern of single nucleotides in the genetic code relative to the properties of the amino acids encoded by each nucleotide triplet, a novel synthetic approach was identified that would yield randomized 18 amino acid hydrophilic peptide libraries with a propensity to form α-helices. According to Table 14, the use of a [(CAG)A(TCAG)] codon mixture yields the hydrophilic amino acids His, Gln, Asn, Lys, Asp, and Glu. These amino acids are most often associated with α-helical motifs except for asparagine, which is classified as a weak α-helical breaker. If this codon mixture was used to build an α-helical peptide, Randomized 18 amino acid hydrophilic α-helical peptide libraries were synthesized using the synthetic oligonucleotide 5' TAC TAT AGA TCT ATG (VAN)$_{17}$ TAA TAA GAA TTC TGC CAG CAC TAT 3' (SEQ ID NO: 65). The complementary strand of the 90 base randomized oligonucleotide was generated by filling in with Klenow using the oligonucleotide primer 5' ATA GTG CTG GCA GAA TTC TTA TTA 3' (SEQ ID NO: 66). After extension the resulting dsDNA was digested with Bgl II and EcoR I and ligated into the pLAC11 expression vector which had been digested with the same two restriction enzymes.

Generating a Randomized Peptide Library Containing the +/− Charge Ending Motif. Randomized peptide libraries stabilized by the interaction of oppositely charge amino acids at the amino and carboxy termini were generated according to the scheme shown in FIG. 9. To maximize the potential interactions of the charged amino acids, the larger acidic amino acid glutamate was paired with the smaller basic amino acid lysine, while the smaller acidic amino acid aspartate was paired with the larger basic amino acid arginine. To construct the randomized peptide libraries, the synthetic oligonucleotide 5' TAC TAT AGA TCT ATG GAA GAC GAA GAC (NNN)$_{16}$ CGT AAA CGT AAA TAA TAA GAA TTC GTA CAT 3' (SEQ ID NO: 67) and the oligonucleotide primer 5' ATG TAC GAA TTC TTA TTA TTT ACG TTT ACG 3' (SEQ ID NO: 68) were used. After extension, the resulting dsDNA was digested with Bgl II and EcoR I and ligated into the pLAC11 expression vector which had been digested with the same two restriction enzymes.

For all libraries of randomized oligonucleotides, N denotes that an equimolar mixture of the four nucleotides A, C, G, and T was used, and V denotes that an equimolar mixture of the three nucleotides A, C and G was used. The resulting libraries were transformed into electrocompetent ALS225 E. coli cells (Example I) under repressed conditions as described in Example II.

Screening of Transformants to Identify Inhibitor Clones. Transformants were initially screened using the grid-patching technique to identify any that could not grow on minimal media as described in Example II when the peptides were overproduced. To verify that all the inhibitors were legitimate, plasmid DNA was made from each inhibitory clone, transformed into a fresh background, then checked to make sure that they were still inhibitory on plates and that their inhibition was dependent on the presence of the inducer, IPTG, as in Example II.

Growth Rate Analysis in Liquid Media. Inhibition strength of the peptides was assessed by subjecting the inhibitory clones to a growth rate analysis in liquid media. Minimal or rich cultures containing either the inhibitor to be tested or the relevant vector as a control were diluted to an initial OD$_{550}$ of approximately 0.01 using new media and induced with 1 mM IPTG. OD$_{550}$ readings were then taken hourly until the cultures had passed log phase. Growth rates were determined as the spectrophotometric change in OD$_{550}$ per unit time within the log phase of growth, and inhibition of the growth rate was calculated for the inhibitors using the appropriate vector as a control.

RESULTS

Isolation and Characterization of Inhibitor Peptides that are Fused at Their Carboxy Terminal End to the Amino Terminal End of the Rop Protein. Approximately 10,000 peptides protected by the Rop protein at their carboxy terminal end were screened using the grid-patching technique described in Example II, and 16 two day inhibitors were isolated. The inhibitory effects were determined as described in the Example II, using pRop(C) as a control. Unlike the anchorless inhibitors identified in Example II that were only inhibitory on minimal media, many of the Rop fusion inhibitors were also inhibitory on rich media as well, which reflects increased potency. As indicated in Table 15, the inhibitors inhibited the bacterial growth rate at levels that averaged 90% in minimal media and at levels that averaged 50% in rich media. The data in Table 15 is the average of duplicate experiments.

TABLE 15

Inhibitory effects of peptide inhibitors stabilized by fusing the carboxy terminal end of the peptide to the amino terminal end of the Rop protein (Rop(C) fusion peptide inhibitors

| Inhibitor | % inhibition in minimal media | % inhibition in rich media |
|---|---|---|
| PRop(C)1 | 87 | 47 |
| PRop(C)2 | 99 | 58 |
| PRop(C)3 | 85 | 54 |
| PRop(C)4 | 98 | 49 |
| PRop(C)5 | 95 | 54 |
| PRop(C)6 | 99 | 46 |
| PRop(C)7 | 91 | 59 |
| PRop(C)8 | 86 | 51 |
| PRop(C)9 | 93 | 57 |
| PRop(C)10 | 91 | 35 |

Isolation and Characterization of Inhibitor Peptides that are Fused at Their Amino Terminal End to the Carboxy Terminal End of the Rop Protein. Approximately 6000 peptides protected at their amino terminal end by Rop protein were screened using the grid-patching technique described in Example II, and 14 two day inhibitors were isolated. As observed for the Rop fusion peptides isolated using the p-Rop(C) vector, most of the inhibitor peptides isolated using the p(N)Rop-vector were inhibitory on rich media as well as minimal media. The inhibitors were verified as described hereinabove and subjected to growth rate analysis using p(N)Rop- as a control in order to determine their potency. As indicated in Table 16, the inhibitors inhibited the bacterial growth rate at levels that averaged 90% in minimal media and at levels that averaged 40% in rich media. The data in Table 16 is the average of duplicate experiments.

TABLE 16

Inhibitory effects of peptide inhibitors stabilized by fusing the amino terminal end of the peptide to the carboxy terminal end of the Rop protein (Rop(N) fusion peptide inhibitors)

| Inhibitor | % inhibition in minimal media | % inhibition in rich media |
|---|---|---|
| pRop(N)1 | 81 | 30 |
| pRop(N)2 | 96 | 53 |
| pRop(N)3 | 95 | 43 |
| pRop(N)4 | 92 | 38 |
| pRop(N)5 | 99 | 33 |
| pRop(N)6 | 93 | 38 |
| pRop(N)7 | 87 | 34 |
| pRop(N)8 | 91 | 44 |
| pRop(N)9 | 95 | 37 |
| pRop(N)10 | 96 | 40 |

Isolation and Characterization of Anchorless Inhibitor Peptides Containing Two Prolines at Both Their Amino Terminal and Carboxy Terminal Ends. Approximately 7500 peptides were screened using the grid-patching technique described in Example II, and 12 two day inhibitors were isolated. As indicated in Table 17, the top ten inhibitors inhibited the bacterial growth rate at levels that averaged 50% in minimal media. The inhibitory effects were determined as described in the text using pLAC11 as a control. The data in Table 17 is the average of duplicate experiments.

TABLE 17

Inhibitory effects of peptide inhibitors stabilized by two proline residues at both the amino and carboxy terminal ends of the peptide

| Inhibitor | % inhibition in minimal media |
|---|---|
| pPro1 | 50 |
| pPro2 | 49 |
| pPro3 | 50 |
| pPro4 | 59 |
| pPro5 | 52 |
| pPro6 | 93 |
| pPro7 | 54 |
| pPro8 | 42 |
| pPro9 | 41 |
| pPro10 | 42 |

Sequence analysis of the coding regions for the top ten inhibitors is shown in Table 19. The landmark Bgl II and EcoR I restriction sites for the insert region are underlined, as are the proline residues.

Since the ends of the oligonucleotide from which these inhibitors were constructed contained Bgl II and EcoRI I restriction sites, the oligonucleotide was not gel isolated when the libraries were prepared in order to maximize the oligonucleotide yields. Because of this, three of the inhibitory clones, pPro2, Ppro5, and pPro6 were found to contain deletions in the randomized portion of the oligonucleotide.

TABLE 18

Sequence analysis of the insert region from the proline peptides

```
pPro1 - 21aa
AGA TCT ATG CCG CCG ATT CTA TGG GGC GAA GCG AGA AAG CGC TTG TGG GGT GGG GAT CAT ACA CCG CCG TAA TAA
     M   P   P   I   L   W   G   E   A   R   K   R   L   W   G   G   D   H   T   P   P   *   *
(SEQ ID NO: 70)
GAA TTC (SEQ ID NO: 69)

pPro2 - 27aa
AGA TCT ATG CCG CCG CCG TTG GAT ATT GTG TCG GGT ATT GAG GTA GGG GGG CAT TTG TGG TGC CGC CGT ATT AAG
     M   P   P   P   L   D   I   V   S   G   I   E   V   G   G   H   L   W   C   R   R   I   K
AAT TCT CAT GTT TGA (SEQ ID NO: 71)
 N   S   H   V   * (SEQ ID NO: 72)

pPro3 - 8aa
AGA TCT ATG CCG CCG GAC AAT CCG GTC CTG TGA TGA AGC GGA GGT CGA CCA AGG GGA TAT CAG CCG CCG TAA TAA
     M   P   P   D   N   P   V   L   *   *   (SEQ ID NO: 74)
GAA TTC (SEQ ID NO: 73)

pPro4 - 9aa
AGA TCT ATG CCG CCG CTA TTG GAC GGA GAT GAC AAA TAG ATA TAT GCG TGG TTG TTT TTC TGT CCG CCG TAA TAA
     M   P   P   L   L   D   G   D   D   K   *   (SEQ ID NO: 76)
GAA TTC (SEQ ID NO: 75)

pPro5 - 10aa
AGA TCT ATG CCG CCG AGG TGG AAG ATG TTG ATA AGA CAG TGA CAG ATG CGT TCC ATT ACT CCC GCC GTA ATA AGA
     M   P   P   R   W   K   M   L   I   R   Q   *   (SEQ ID NO: 78)
ATT C (SEQ ID NO: 77)

pPro6 - 7aa
AGA TCT ATG ATG AGA GTA GCG CCG CCG TAA TAA GAA TTC (SEQ ID NO: 79)
     M   M   R   V   A   P   P   *   *   (SEQ ID NO: 80)

pPro7 - 14aa
AGA TCT ATG CCG CCG TTG CGC GGG GCA TGC GAT GTA TAT GGG GTA AAT TGA ATG TCT TGT GGG CCG CCG TAA TAA
     M   P   P   L   R   G   A   C   D   V   Y   G   V   N   *   (SEQ ID NO: 82)
GAA TTC (SEQ ID NO: 81)

pPro8 - 21aa
AGA TCT ATG CCG CCG GGG AGA GGG GAA GCG GTG GGA GTG ACA TGC TTG AGC GCG AAC GTG TAC CCG CCG TAA TAA
     M   P   P   G   R   G   E   A   V   G   V   T   C   L   S   A   N   V   Y   P   P   *   *
(SEQ ID NO: 84)
GAA TTC (SEQ ID NO: 83)

pPro9 - 21aa
AGA TCT ATG CCG CCG GGA AGG GTA GTG TTC TTT GTC GCT ATC TTT GTT TCC GCA ATA TGC CTC CCG CCG TAA TAA
     M   P   P   G   R   V   V   F   F   V   A   I   F   V   S   A   I   C   L   P   P   *   *
(SEQ ID NO: 86)
GAA TTC (SEQ ID NO: 85)

pPro10 - 21aa
AGA TCT ATG CCG CCG AGG TTC GCT CAT GAG AGT GTT AAA GGG CTG GGG GAC GTT ACA AAA GCT CCG CCG TAA TAA
     M   P   P   R   F   A   H   E   S   V   K   G   L   G   D   V   T   K   A   P   P   *   *
(SEQ ID NO: 88)
GAA TTC (SEQ ID NO: 87)
```

All the inhibitors were found to contain two proline residues at either their amino or carboxy termini as expected. Four inhibitors contained two proline residues at both their amino and carboxy termini, five inhibitors contained two proline residues at only their amino termini, and one inhibitor contained two proline residues at only its carboxy terminus.

found to contain deletions in the randomized portion of the oligonucleotide. The predicted α-helical content of these peptides is indicated in Table 20 according to the secondary structure prediction rules of Garnier, Osguthorpe, and Robson (J. Garnier et al., J. Mol. Biol. 120:97–120 (1978)) prediction rules.

TABLE 20

Sequence analysis of the insert region from the hydrophilic α-helical peptides

```
pHelix1 - 18aa, 83% α-helical
AGA TCT ATG CAT GAC GAA CAA GAG GAG GAG CAC AAT AAA AAG GAT AAC GAA AAA GAA CAC TAA TAA GAA
        M   H   D   E   Q   E   E   H   N   K   K   D   N   E   K   E   H   *   *   (SEQ ID NO: 90)
TTC  (SEQ ID NO: 89)

pHelix2 - 22aa, 68% α-helical
AGA TCT ATG CAG CAG GAG CAC GAG CAA GGC AGG ATG AGC AAG AGG ATG AAG AAT AAT AAG AAT TCT CAT
        M   Q   Q   E   H   E   Q   G   R   M   S   K   R   M   K   N   N   K   N   S   H
GTT TGA  (SEQ ID NO: 91)
 V   *   (SEQ ID NO: 92)

pHelix3 - 22aa, 55% α-helical
AGA TCT ATG AAC CAT CAT AAT GAG GCC ATG ATC AAC ACA ATG AAA ACG AGG AAT AAT AAG AAT TCT CAT
        M   N   H   H   N   E   A   M   I   N   T   M   K   T   R   N   N   K   N   S   H
GTT TGA  (SEQ ID NO: 93)
 V   *   (SEQ ID NO: 94)

pHelix4 - 18aa, 17% α-helical
AGA TCT ATG AAC GAC GAC AAT CAG CAA GAG GAT AAT CAT GAT CAG CAT AAG GAT AAC AAA TAA TAA GAA
        M   N   D   D   N   Q   Q   E   D   N   H   D   Q   H   K   D   N   K   *   *   (SEQ ID NO: 96)
TTC  (SEQ ID NO: 95)

pHelix5 - 18aa, 50% α-helical
AGA TCT ATG CAA GAG CAG GAT CAG CAT AAT GAT AAC CAT CAC GAG GAT AAA CAT AAG AAG TAA TAA GAA
        M   Q   E   Q   D   Q   H   N   D   N   H   H   E   D   K   H   K   K   *   *   (SEQ ID NO: 98)
TTC  (SEQ ID NO: 97)
```

Isolation and Characterization of Anchorless Hydrophilic Inhibitor Peptides Stabilized by an α-Helical Motif. Approximately 12,000 peptides were screened using the grid-patching technique and 5 two-day inhibitors were isolated. The inhibitors were verified as already described for the Rop-peptide fusion studies and subjected to growth rate analysis using pLAC11 as a control in order to determine their potency. As indicated in Table 19, the inhibitor peptides inhibited the bacterial growth rate at levels that averaged 50% in minimal media. The averaged values of two independent determinations are shown.

TABLE 19

Inhibitory effects of the hydrophilic α-helical peptides

| Inhibitor | % inhibition in minimal media |
|---|---|
| pHelix1 | 67 |
| pHelix2 | 46 |
| pHelix3 | 48 |
| pHelix4 | 45 |
| pHelix5 | 42 |

Sequence analysis of the coding regions for the 5 inhibitors is shown in Table 20. The landmark Bgl II and EcoR I restriction sites for the insert region are underlined. Since the ends of the oligonucleotide from which these inhibitors were constructed contained these restriction sites, the oligonucleotide was not gel isolated when the libraries were prepared in order to maximize the oligonucleotide yields. Because of this, two of the inhibitory clones, pHelix2 and pHelix3, were According to Garnier, Osguthorpe, and Robson secondary structure prediction, all of the encoded peptides are expected to be largely α-helical except for pHelix4. Interestingly, pHelix1, which had the highest degree of α-helical content, was also the most potent inhibitory peptide that was isolated in this study.

Isolation and Characterization of Anchorless Inhibitor Peptides Stabilized by an Opposite Charge Ending Motif. Approximately 20,000 peptides were screened using the grid-patching technique and 6 two day inhibitors were isolated. The inhibitors were verified as already described for the Rop-peptide fusion studies and subjected to growth rate analysis using pLAC11 as a control in order to determine their potency. As indicated in Table 21, the inhibitor peptides inhibited the bacterial growth rate at levels that averaged 50% in minimal media. The averaged values of two independent determinations are shown.

TABLE 21

Inhibitory effects of peptide inhibitors that are stabilized by the opposite charge ending motif

| Inhibitor | % inhibition in minimal media |
|---|---|
| p+/−1 | 41 |
| p+/−2 | 43 |
| p+/−3 | 48 |
| p+/−4 | 60 |
| p+/−5 | 54 |
| p+/−6 | 85 |

Sequence analysis of the coding regions for the six inhibitors is shown in Table 22. The landmark Bgl II and EcoR I restriction sites for the insert region are underlined. With the exception of p+/−4, which was terminated prematurely, the coding regions for the inhibitors were as expected based on the motif that was used to generate the peptide libraries.

TABLE 22

Sequence analysis of the insert region from the opposite charge ending peptides

```
p+/-1 - 25aa
AGA TCT ATG GAA GAC GAA GAC GAG GGT GCG TCA GCG TGG GGA GCA GAA CTT TGG TCG TGG CAG TCG GTG
        M   E   D   E   D   E   G   A   S   A   W   G   A   E   L   W   S   W   Q   S   V
CGT AAA CGT AAA TAA TAA GAA TTC  (SEQ ID NO: 99)
 R   K   R   K   *   *     (SEQ ID NO: 100)

p+/-2 - 25aa
AGA TCT ATG GAA GAC GAA GAC GGT CTA GGC ATG GGG CGT GGG TTG GTC AGG CTC ACT TTA TTA TTC TTC
        M   E   D   E   D   G   L   G   M   G   G   G   L   V   R   L   T   L   L   F   F
CGT AAA CGT AAA TAA TAA GAA TTC  (SEQ ID NO: 101)
 R   K   R   K   *   *     (SEQ ID NO: 102)

p+/-3 - 25aa
AGA TCT ATG GAA GAC GAA GAC GGG GAG AGG ATC CAG GGG GCC CGC TGT CCA GTA GCG CTG GTA GAT AGA
        M   E   D   E   D   G   E   R   I   Q   G   A   R   C   P   V   A   L   V   D   R
CGT AAA CGT AAA TAA TAA GAA TTC (SEQ ID NO: 103)
 R   K   R   K   *   *    (SEQ ID N0: 104)

p+/-4 - 11aa
AGA TCT ATG GAA GAC GAA GAC GAC AGG GGG CGT GGG CGG TAG CTT TAA GTT GCG CTA AGT TGC GAG ATA
        M   E   D   E   D   D   R   G   R   G   R   *   (SEQ ID NO: 105)
CGT AAA CGT AAA TAA TAA GAA TTC  (SEQ ID NO: 106)

p+/-5 - 25aa
AGA TCT ATG GAA GAC GAA GAC GGG GGG GCC GGG AGG AGG GCC TGT CTT TGT TCC GCG CTT GTT GGG GAA
        M   E   D   E   D   G   G   A   G   R   R   A   C   L   C   S   A   L   V   G   E
CGT AAA CGT AAA TAA TAA GAA TTC  (SEQ ID NO: 107)
 R   K   R   K   *   *   (SEQ ID NO: 108)

p+/-6 - 25aa
AGA TCT ATG GAA GAC GAA GAC AAG CGT CGC GAG AGG AGT GCA AAA GGG CGT CAT GTC GGT CGG TCG ATG
        M   E   D   E   D   K   R   R   E   R   S   A   K   G   R   H   V   G   R   S   M
CGT AAA CGT AAA TAA GAC TGT (SEQ ID NO: 109)
 R   K   R   K   *   (SEQ ID NO: 110)
```

DISCUSSION

In Example II, where fully randomized peptides were screened for inhibitory effect, only three peptides (one "anchorless" and two unanticipated Rop fusions resulting from deletion) were identified out of 20,000 potential candidates as a potent (i.e., two day) inhibitor of *E. coli* bacteria. Using a biased synthesis as in this Example, it was possible to significantly increase the frequency of isolating potent growth inhibitors (see Table 23).

TABLE 23

Summary of the frequency at which the different types of inhibitor peptides can be isolated

| Type of inhibitor peptide | Frequency at which a two day inhibitor peptide can be isolated | Reference |
|---|---|---|
| anchorless | 1 in 20,000 | Example II |
| protected at the C-terminal end via Rop | 1 in 625 | This example |
| protected at the N-terminal end via Rop | 1 in 429 | This example |
| protected at both the C-terminal and N-terminal end via two prolines | 1 in 625 | This example |
| protected with an α-helix structural motif | 1 in 2,400 | This example |
| protected with an opposite charge ending motif | 1 in 3,333 | This example |

Many more aminopeptidases have been identified than carboxypeptidases in both prokaryotic and eukaryotic cells (J. Bai, et al., Pharm. Res. 9:969–978 (1992); J. Brownlees et al., J. Neurochem. 60:793–803 (1993); C. Miller, In *Escherichia coli* and *Salmonella typhimurium* cellular and molecular biology, 2nd edition (Neidhardt, F. C. ed.), ASM Press, Washington, D.C. 1:938–954 (1996)). In the Rop fusion studies, it might have therefore been expected that stabilizing the amino terminal end of the peptide would have been more effective at preventing the action of exopeptidases than stabilizing the carboxy end of the peptides. Surprisingly, it was found that stabilizing either end of the peptide caused about the same effect.

Peptides could also be stabilized by the addition of two proline residues at the amino and/or carboxy termini, the incorporation pf opposite charge ending amino acids at the amino and carboxy termini, or the use of helix-generating hydrophilic amino acids. As shown in Table 23, the frequency at which potent inhibitor peptides could be isolated increased significantly over that of the anchorless peptides characterized in Example II.

These findings can be directly implemented to design more effective peptide drugs that are resistant to degradation by peptidases. In this example, several strategies were shown to stabilize peptides in a bacterial host. Because the aminopeptidases and carboxypeptidases that have been characterized in prokaryotic and eukaryotic systems appear to function quite similarly (C. Miller, In *Escherichia coli* and *Salmonella typhimurium* cellular and molecular biology, 2nd edition (Neidhardt, F. C. ed.), ASM Press, Washington, D.C. 1:938–954 (1996); N. Rawlings et al., Biochem J. 290:205–218 (1993)), the incorporation of on or more of these motifs into new or known peptide drugs should slow or prevent the action of exopeptidases in a eukaryotic host cell as well.

Sequence Listing Free Text

SEQ ID NO:2
peptide sequence having opposite charge ending motif.
SEQ ID NOs:3–4
stabilized angiotensin
SEQ ID NOs:6–19, 24–28, 55–58, 60, 62, 64, 66, 68
primer
SEQ ID NOs:20–22
primer fragment
SEQ ID NOs:23, 59, 61, 63, 65, 67
randomized oligonucleotide
SEQ ID NOs:29–33
antisense oligonucleotide
SEQ ID NOs:34, 36, 39, 40, 43, 45, 46, 48, 51, 52, 70, 72, 74, 76, 78, 80, 82, 84, 86, 88, 90, 92, 94, 96, 98, 100, 102, 104, 105, 108, 110
stabilized peptide
SEQ ID NOs:35, 37, 38, 41, 42, 44, 47, 49, 50, 53, 69, 71, 73, 75, 77, 79, 81, 83, 85, 87, 89, 91, 93, 95, 97, 99, 101, 103, 106, 107, 109
nucleic acid encoding stabilized peptide
SEQ ID NO:54
N-terminal protective sequence The foregoing detailed description and examples have been given for clarity of understanding only. No unnecessary limitations are to be understood therefrom. The invention is not limited to the exact details shown and described, for variations obvious to one skilled in the art will be included within the invention defined by the claim.

What is claimed is:

1. A non-naturally occurring polypeptide comprising a bioactive peptide, a first stabilizing group attached to the N-terminus of the bioactive peptide, and a second stabilizing group attached to the C-terminus of the bioactive peptide, wherein the first stabilizing group is selected from the group consisting of a small stable protein, Pro-, Pro-Pro-, Xaa-Pro- and Xaa-Pro-Pro-, and wherein the second stabilizing group is selected from the group consisting of a small stable protein, -Pro, -Pro-Pro, -Pro-Xaa and -Pro-Pro-Xaa.

2. The polypeptide of claim 1 wherein the bioactive peptide is a naturally occurring bioactive peptide.

3. The polypeptide of claim 1 wherein the small stable protein is selected from the group consisting of Rop protein, glutathione sulfotransferase, thioredoxin, maltose binding protein, and glutathione reductase.

4. The polypeptide of claim 1 wherein the first stabilizing group is Pro-Pro- and the second stabilizing group is -Pro-Pro.

5. The polypeptide of claim 1 wherein at least one of the first and second stabilizing groups comprises a small stable protein.

6. The polypeptide of claim 5 wherein the small stable protein is a four-helix bundle protein.

7. The polypeptide of claim 5 wherein the small stable protein is selected from the group consisting of Rop protein, glutathione sulfotransferase, thioredoxin, maltose binding protein, and glutathione reductase.

8. The polypeptide of claim 7 wherein the small stable protein is Rop protein.

9. The polypeptide of claim 1 which is an antimicrobial peptide.

10. The polypeptide of claim 1 which is a therapeutic peptide drug.

11. A non-naturally occurring polypeptide comprising:

a bioactive peptide;

a first stabilizing group attached to the N-terminus of said bioactive peptide, wherein said first stabilizing group is selected from the group consisting of a small stable protein, -Pro-, -Pro-Pro-, -Xaa-Pro- and -Xaa-Pro-Pro-;

a second stabilizing group attached to the C-terminus of said bioactive peptide, wherein said second stabilizing group is selected from the group consisting of a small stable protein, -Pro, -Pro-Pro, -Pro-Xaa and -Pro-Pro-Xaa; and a cleavage site immediately preceding the first stabilizing group.

12. The polypeptide of claim 11 wherein the bioactive peptide is a naturally occurring bioactive peptide.

13. A non-naturally occurring polypeptide comprising:

a bioactive peptide;

a first stabilizing group attached to the N-terminus of said bioactive peptide, wherein said first stabilizing group is selected from the group consisting of a small stable protein, Pro-, Pro-Pro-, Xaa-Pro- and Xaa-Pro-Pro-;

a second stabilizing group attached to the C-terminus of said bioactive peptide, wherein said second stabilizing group is selected from the group consisting of a small stable peptide, -Pro, -Pro-Pro, -Pro-Xaa and -Pro-Pro-Xaa; and a cleavage site immediately following the second stabilizing group.

14. The peptide of claim 13 wherein the bioactive peptide is a naturally occurring bioactive peptide.

15. A non-naturally occurring polypeptide comprising a bioactive peptide and a stabilizing group attached to each or both of the N-terminus or C-terminus of the bioactive peptide, wherein the stabilizing group attached to the N-terminus, comprises Xaa-Pro-Pro-, and the stabilizing group attached to the C-terminus, comprises -Pro-Pro-Xaa.

16. The polypeptide of claim 15 wherein the bioactive peptide is a naturally occurring bioactive peptide.

17. A non-naturally occurring polypeptide comprising a bioactive peptide and a stabilizing group consisting Rop protein attached to either or both of the N-terminus or C-terminus of the bioactive peptide.

18. The polypeptide of claim 17 wherein the bioactive peptide is a naturally occurring bioactive peptide.

19. A non-naturally occurring polypeptide comprising a bioactive peptide and a stabilizing group comprising a four-helix bundle protein attached to either or both of the N-terminus or C-terminus of the bioactive peptide.

20. The polypeptide of claim 19 wherein the bioactive peptide is a naturally occurring bioactive peptide.

* * * * *

UNITED STATES PATENT AND TRADEMARK OFFICE
CERTIFICATE OF CORRECTION

PATENT NO. : 6,818,611 B1
APPLICATION NO. : 09/701947
DATED : November 16, 2004
INVENTOR(S) : Elliot Altman It is certified that error appears in the above-identified patent and that said Letters Patent is hereby corrected as shown below:

Face Page, Page 2, Column 2 - (54) Publications
Delete "Blane" and insert --Blanc--

Delete "Lechrer" and insert --Lehrer--

Column 2 (Table 2 continued)
Line 13, delete "EET1 II" and insert --EETI II--

Column 2 (Table 3)
Line 51, insert --Receptor-- after "Nicotinic Acetylcholine"
Line 53, delete "EET1 II" and insert --EETI II--

Line 61, insert --Protein Kinase-- after "cAMP-Dependent"

Line 62, delete "Protein Calpain" and insert --Calpain--

Line 64, delete "$1.5 \times 10^{-9}$M" and insert --$2.5 \times 10^{-9}$ M--

Column 5
Line 49, delete "proteion" and insert --protein--

Column 19 (Table 4) *E.coli* Strains
Delete "ALS221   BL21(DE3)   ompT hsd5(b)(R-M-) gal dem" and insert --ALS221   BL21(DE3) ompT hsdS(b)(R-M-) gal dcm--

Delete "ALS224   MC1061   araD139Δ(araABOIC-leu)7679 A(lac)X74" and insert --ALS224   MC1061   araD139Δ(araABOIC-leu)7679   Δ(lac)X74--

Delete "ALS413   MG1655   *E. coli* wild-type F-γ" and insert --ALS413   MG1655 *E. coli* wild-type F-λ--

Column 19 (Table 4) Plasmids
delete "pKK223-3   lac promoter/operator, $Amp^R$, colE1 replicon" and insert --pKK223-3   tac promoter/operator, $Amp^R$, colE1 replicon-- delete "pTre$^{99}$A   trc promoter/operator, $lacI^q$, $Amp^R$, colE1 replicon" and insert --pTrc99A   trc promoter/operator, $lacI^q$, $Amp^R$, colE1 replicon-- delete "pXE60   wild-type TOL pWWO xylE gene. $Amp^R$" and insert --pXE60   wild-type TOL pWWO xylE gene, $Amp^R$--

UNITED STATES PATENT AND TRADEMARK OFFICE
CERTIFICATE OF CORRECTION

PATENT NO. : 6,818,611 B1
APPLICATION NO. : 09/701947
DATED : November 16, 2004
INVENTOR(S) : Elliot Altman It is certified that error appears in the above-identified patent and that said Letters Patent is hereby corrected as shown below:

Column 21 (Table 5)
SEQ ID NO:7 should read: -- ATT GAA TTC ATA AGA TCT TTC CTG TGT GAA ATT GTT ATC CGC --

SEQ ID NO: 8 should read: -- ATT GAA TTC ACC ATG GAC ACC ATC GAA TGG TGC AAA A --

SEQ ID NO: 9 should read: -- GTT GTT GCC ATT GCT GCA G --

Column 24 (Table 6)
The last three lines of Table 6:
delete
"pET-21(-) Plasmid  2929 16803 6X" and insert --pET-21(+) Plasmid  2929  16803  6X-- delete "pET-21(-)/pLysE Plasmid  4085  19558  5X" and insert --pET-21(+)/pLysE Plasmid  4085  19558  5X-- delete "pET-21(-)/pLysS Plasmid  1598  20268  13X" and insert --pET-21(+)/pLysS Plasmid  1598  20268  13X--

Column 25 (Table 7)
delete "ALS225 (recA$^+$)   178,000   152,000" and insert --ALS225 (recA$^+$)  178,000  182,000--

Column 25, Line 50
delete "$OD_{50}$" and insert --$OD_{550}$--

Column 29, Line 33
delete "WPTG" and insert --IPTG--

Column 37, (Table 13)
delete "EET1 II   29   disulfide bonds 23" and insert --EETI II  29 disulfide bonds  23--

Column 92, Line 63 (Claim 15)
delete "each" and insert --either--

UNITED STATES PATENT AND TRADEMARK OFFICE
CERTIFICATE OF CORRECTION

PATENT NO. : 6,818,611 B1
APPLICATION NO. : 09/701947
DATED : November 16, 2004
INVENTOR(S) : Elliot Altman It is certified that error appears in the above-identified patent and that said Letters Patent is hereby corrected as shown below:

<u>Column 93, Line 4 (Claim 17)</u>
delete "consisting" and insert --comprising--

Signed and Sealed this

Thirty-first Day of July, 2007

JON W. DUDAS
*Director of the United States Patent and Trademark Office*

UNITED STATES PATENT AND TRADEMARK OFFICE
CERTIFICATE OF CORRECTION

PATENT NO. : 6,818,611 B1
APPLICATION NO. : 09/701947
DATED : November 16, 2004
INVENTOR(S) : Elliot Altman It is certified that error appears in the above-identified patent and that said Letters Patent is hereby corrected as shown below:

Face Page, Page 2, Column 2 - (54) Publications
Delete "Blane" and insert --Blanc--

Delete "Lechrer" and insert --Lehrer--

Column 2 (Table 2 continued)
Line 13, delete "EET1 II" and insert --EETI II--

Column 2 (Table 3)
Line 51, insert --Receptor-- after "Nicotinic Acetylcholine"
Line 53, delete "EET1 II" and insert --EETI II--

Line 61, insert --Protein Kinase-- after "cAMP-Dependent"

Line 62, delete "Protein Calpain" and insert --Calpain--

Line 64, delete "$1.5 \times 10^{-9} M$" and insert --$2.5 \times 10^{-9}$ M--

Column 5
Line 49, delete "proteion" and insert --protein--

Column 19 (Table 4) *E.coli* Strains
Delete "ALS221    BL21(DE3)  ompT hsd5(b)(R-M-) gal dem" and insert --ALS221   BL21(DE3) ompT hsdS(b)(R-M-) gal dcm--

Delete "ALS224    MC1061    araD139Δ(araABOIC-leu)7679 A(lac)X74" and insert --ALS224    MC1061    araD139Δ(araABOIC-leu)7679    Δ(lac)X74--

Delete "ALS413    MG1655    *E. coli* wild-type F-γ" and insert --ALS413    MG1655 *E. coli* wild-type F-λ--

Column 19 (Table 4) Plasmids
delete "pKK223-3    lac promoter/operator, $Amp^R$, colE1 replicon" and insert --pKK223-3    tac promoter/operator, $Amp^R$, colE1 replicon-- delete "pTre$^{99}$A    trc promoter/operator, lacI$^q$, $Amp^R$, colE1 replicon" and insert --pTrc99A    trc promoter/operator, lacI$^q$, $Amp^R$, colE1 replicon-- delete "pXE60    wild-type TOL pWWO xylE gene. $Amp^R$" and insert --pXE60    wild-type TOL pWWO xylE gene, $Amp^R$--

UNITED STATES PATENT AND TRADEMARK OFFICE
CERTIFICATE OF CORRECTION

PATENT NO.        : 6,818,611 B1
APPLICATION NO. : 09/701947
DATED              : November 16, 2004
INVENTOR(S)      : Elliot Altman It is certified that error appears in the above-identified patent and that said Letters Patent is hereby corrected as shown below:

Column 21 (Table 5)
SEQ ID NO:7 should read: -- ATT GAA TTC ATA AGA TCT TTC CTG TGT GAA ATT GTT ATC CGC --

SEQ ID NO: 8 should read: -- ATT GAA TTC ACC ATG GAC ACC ATC GAA TGG TGC AAA A --

SEQ ID NO: 9 should read: -- GTT GTT GCC ATT GCT GCA G --

Column 24 (Table 6)
The last three lines of Table 6:
delete
"pET-21(-) Plasmid  2929  16803  6X" and insert --pET-21(+) Plasmid  2929  16803  6X-- delete "pET-21(-)/pLysE Plasmid  4085  19558  5X" and insert --pET-21(+)/pLysE Plasmid  4085  19558  5X-- delete "pET-21(-)/pLysS Plasmid  1598  20268  13X" and insert --pET-21(+)/pLysS Plasmid  1598  20268  13X--

Column 25 (Table 7)
delete "ALS225 (recA$^+$)  178,000  152,000" and insert --ALS225 (recA$^+$)  178,000  182,000--

Column 25, Line 50
delete "OD$_{50}$" and insert --OD$_{550}$--

Column 29, Line 33
delete "WPTG" and insert --IPTG--

Column 37, (Table 13)
delete "EET1 II  29  disulfide bonds 23" and insert --EETI II  29  disulfide bonds  23--

Column 92, Line 63 (Claim 15)
delete "each" and insert --either--

UNITED STATES PATENT AND TRADEMARK OFFICE
CERTIFICATE OF CORRECTION

PATENT NO. : 6,818,611 B1
APPLICATION NO. : 09/701947
DATED : November 16, 2004
INVENTOR(S) : Elliot Altman It is certified that error appears in the above-identified patent and that said Letters Patent is hereby corrected as shown below:

<u>Column 93, Line 4 (Claim 17)</u>
delete "consisting" and insert --comprising--

This certificate supersedes Certificate of Correction issued July 31, 2007.

Signed and Sealed this

Twenty-first Day of August, 2007

JON W. DUDAS
*Director of the United States Patent and Trademark Office*

UNITED STATES PATENT AND TRADEMARK OFFICE
CERTIFICATE OF CORRECTION

PATENT NO. : 6,818,611 B1
APPLICATION NO. : 09/701947
DATED : November 16, 2004
INVENTOR(S) : Elliot Altman It is certified that error appears in the above-identified patent and that said Letters Patent is hereby corrected as shown below:

Face Page, Page 2, Column 2 - (54) Publications
Delete "Blane" and insert --Blanc--

Delete "Lechrer" and insert --Lehrer--

Column 2 (Table 2 continued)
Line 13, delete "EET1 II" and insert --EETI II--

Column 2 (Table 3)
Line 51, insert --Receptor-- after "Nicotinic Acetylcholine"
Line 53, delete "EET1 II" and insert --EETI II--

Line 61, insert --Protein Kinase-- after "cAMP-Dependent"

Line 62, delete "Protein Calpain" and insert --Calpain--

Line 64, delete "$1.5 \times 10^{-9}$M" and insert --$2.5 \times 10^{-9}$ M--

Column 5
Line 49, delete "proteion" and insert --protein--

Column 19 (Table 4) *E.coli* Strains
Delete "ALS221   BL21(DE3)   ompT hsd5(b)(R-M-) gal dem" and insert --ALS221   BL21(DE3) ompT hsdS(b)(R-M-) gal dcm--

Delete "ALS224   MC1061   araD139Δ(araABOIC-leu)7679 A(lac)X74" and insert --ALS224   MC1061   araD139Δ(araABOIC-leu)7679   Δ(lac)X74--

Delete "ALS413   MG1655   *E. coli* wild-type F-γ" and insert --ALS413   MG1655 *E. coli* wild-type F-λ--

Column 19 (Table 4) Plasmids
delete "pKK223-3   lac promoter/operator, $Amp^R$, colE1 replicon" and insert --pKK223-3   tac promoter/operator, $Amp^R$, colE1 replicon-- delete "pTre$^{99}$A   trc promoter/operator, $lacI^q$, $Amp^R$, colE1 replicon" and insert --pTrc99A   trc promoter/operator, $lacI^q$, $Amp^R$, colE1 replicon-- delete "pXE60   wild-type TOL pWWO xylE gene. $Amp^R$" and insert --pXE60   wild-type TOL pWWO xylE gene, $Amp^R$--

UNITED STATES PATENT AND TRADEMARK OFFICE
CERTIFICATE OF CORRECTION

PATENT NO. : 6,818,611 B1
APPLICATION NO. : 09/701947
DATED : November 16, 2004
INVENTOR(S) : Elliot Altman It is certified that error appears in the above-identified patent and that said Letters Patent is hereby corrected as shown below:

Column 21 (Table 5)
SEQ ID NO:7 should read: -- ATT GAA TTC ATA AGA TCT TTC CTG TGT GAA ATT GTT ATC CGC --

SEQ ID NO: 8 should read: -- ATT GAA TTC ACC ATG GAC ACC ATC GAA TGG TGC AAA A --

SEQ ID NO: 9 should read: -- GTT GTT GCC ATT GCT GCA G --

Column 24 (Table 6)
The last three lines of Table 6:
delete "pET-21(-) Plasmid 2929 16803 6X" and insert --pET-21(+) Plasmid 2929 16803 6X-- delete "pET-21(-)/pLysE Plasmid 4085 19558 5X" and insert --pET-21(+)/pLysE Plasmid 4085 19558 5X-- delete "pET-21(-)/pLysS Plasmid 1598 20268 13X" and insert --pET-21(+)/pLysS Plasmid 1598 20268 13X--

Column 25 (Table 7)
delete "ALS225 (recA$^+$)   178,000   152,000" and insert --ALS225 (recA$^+$)   178,000   182,000--

Column 25, Line 50
delete "OD$_{50}$" and insert --OD$_{550}$--

Column 29, Line 33
delete "WPTG" and insert --IPTG--

Column 37, (Table 13)
delete "EET1 II   29   disulfide bonds 23" and insert --EETI II   29 disulfide bonds   23--

Column 92, Line 63 (Claim 15)
delete "each" and insert --either--

UNITED STATES PATENT AND TRADEMARK OFFICE
CERTIFICATE OF CORRECTION

| | |
|---|---|
| PATENT NO. | : 6,818,611 B1 |
| APPLICATION NO. | : 09/701947 |
| DATED | : November 16, 2004 |
| INVENTOR(S) | : Elliot Altman |

It is certified that error appears in the above-identified patent and that said Letters Patent is hereby corrected as shown below:

<u>Column 93, Line 4 (Claim 17)</u>
delete "consisting" and insert --comprising--

This certificate supersedes Certificates of Correction issued July 31, 2007 and August 21, 2007.

Signed and Sealed this

Eighteenth Day of September, 2007

JON W. DUDAS
*Director of the United States Patent and Trademark Office*